United States Patent [19]

Sinay

[11] 4,290,114
[45] Sep. 15, 1981

[54] MEDICAL DIAGNOSTIC COMPUTER

[76] Inventor: Hanon S. Sinay, 1601 Chestnut Ave., Manhattan Beach, Calif. 90266

[21] Appl. No.: 702,337

[22] Filed: Jul. 1, 1976

[51] Int. Cl.³ .............................................. G06F 15/42
[52] U.S. Cl. ..................................... 364/900; 364/300
[58] Field of Search ............... 364/300, 200 MS File, 364/900 MS File

[56] References Cited

U.S. PATENT DOCUMENTS

| | | | |
|---|---|---|---|
| 3,197,742 | 7/1965 | Rettig et al. | 364/900 |
| 3,735,366 | 5/1973 | Abrams et al. | 364/200 |
| 3,810,102 | 5/1974 | Parks et al. | 340/172.5 |
| 3,872,448 | 3/1975 | Mitchell, Jr. | 340/172.5 |
| 3,921,147 | 11/1975 | Fuhr et al. | 340/172.5 |
| 3,934,226 | 1/1976 | Stone et al. | 340/172.5 |

*Primary Examiner*—Raulfe B. Zache
*Attorney, Agent, or Firm*—Narvin H. Kleinberg; Seymour A. Scholnick

[57] ABSTRACT

A computer-aided health care system for use by a paramedic. Findings taken from the patient by the paramedic are assigned numerical codes by use of preprinted forms. The paramedic uses a keyboard to enter the numerical codes into a fixed purpose computer. The computer compares the findings with a number of disease definitions stored in its memory. The computer then operates a printer to list numerical codes for all treatments to be administered. The paramedic uses these codes to enter a treatment and diagnostic manual which gives the name of the disease and specific instructions for its treatment, in the language of the paramedic.

5 Claims, 30 Drawing Figures

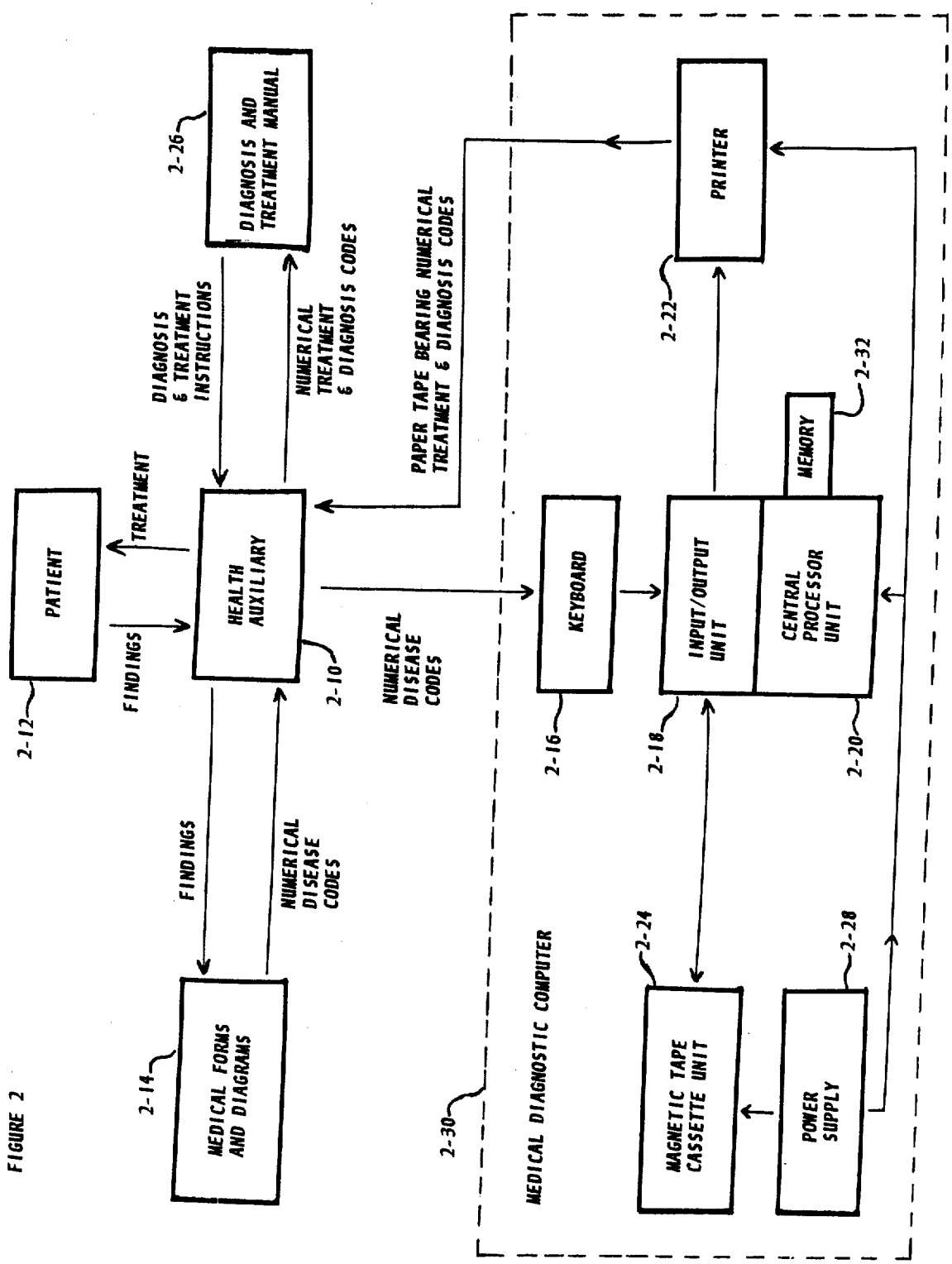

FIGURE 3

PATIENT NAME _____ PATIENT # _____ EXAM # _____ FORM 1

| SEX MALE 108 FEMALE 109 | HEIGHT | WEIGHT | BLOOD PRESSURE | |
|---|---|---|---|---|
| AGE | CM | KG | SYSTOLIC MM HG | DIASTOLIC MM HG |

| DAYS | YEARS | CM | KG | SYSTOLIC MM HG | DIASTOLIC MM HG |
|---|---|---|---|---|---|
| 1 – 100 | 1 – 103 | 30 – 104 | 1 – 105 | 0 – 106 | 0 – 107 |
| 2 – 100 | 2 – 103 | 35 – 104 | 2 – 105 | 20 – 106 | 20 – 107 |
| 3 – 100 | 3 – 103 | 40 – 104 | 3 – 105 | 30 – 106 | 30 – 107 |
| 4 – 100 | 4 – 103 | 45 – 104 | 4 – 105 | 40 – 106 | 40 – 107 |
| 5 – 100 | 5 – 103 | 50 – 104 | 5 – 105 | 50 – 106 | 50 – 107 |
| 6 – 100 | 8 – 103 | 55 – 104 | 6 – 105 | 60 – 106 | 60 – 107 |
|  | 10 – 103 | 60 – 104 | 7 – 105 | 70 – 106 | 70 – 107 |
| WEEKS | 12 – 103 | 70 – 104 | 8 – 105 | 80 – 106 | 80 – 107 |
| 1 – 101 | 14 – 103 | 80 – 104 | 9 – 105 | 90 – 106 | 90 – 107 |
| 2 – 101 | 16 – 103 | 90 – 104 | 10 – 105 | 100 – 106 | 100 – 107 |
| 3 – 101 | 20 – 103 | 100 – 104 | 20 – 105 | 110 – 106 | 110 – 107 |
|  | 30 – 103 | 120 – 104 | 30 – 105 | 120 – 106 | 120 – 107 |
|  | 40 – 103 | 140 – 104 | 40 – 105 | 130 – 106 | 130 – 107 |
| MONTHS | 50 – 103 | 160 – 104 | 50 – 105 | 140 – 106 | 140 – 107 |
| 1 – 102 | 60 – 103 | 180 – 104 | 60 – 105 | 160 – 106 | 160 – 107 |
| 2 – 102 | 70 – 103 | 200 – 104 | 70 – 105 | 180 – 106 | 180 – 107 |
| 3 – 102 | 80 – 103 |  | 80 – 105 | 200 – 106 | 200 – 107 |
| 6 – 102 | 90 – 103 |  | 90 – 105 | 220 – 106 | 220 – 107 |
| 9 – 102 |  |  | 100 – 105 | 240 – 106 | 240 – 107 |

| CONSCIOUS ☐ | SEMI-CONSCIOUS 110 | UNCONSCIOUS 111 | ANKLE TENDON PINCH: | WITHDRAWAL & SOME OTHER RESPONSE 112 | WITHDRAWAL & NO OTHER RESPONSE 113 | NO RESPONSE 114 |
|---|---|---|---|---|---|---|

| ALERT ☐ | DULL 115 | SLEEPY 116 | WHO FORGET 117 | WHO WRONG 118 | WHERE FORGET 119 | WHERE WRONG 120 | WHEN FORGET 121 | WHEN WRONG 122 |
|---|---|---|---|---|---|---|---|---|

| CALM ☐ | ANGER 123 | AGITATED 124 | DEPRESSED 125 | FEARFUL 126 |
|---|---|---|---|---|

| HALLUCINATIONS NO ☐ YES 127 | HEARING 128 | VISUAL 129 | SMELL 130 | TASTE 131 | TOUCH 132 |
|---|---|---|---|---|---|

| SPEECH YES ☐ NO 133 | MEANING MEANINGFUL ☐ SENSELESS 134 | WORDS CLEAR ☐ GARBLED 135 | PAIN NO ☐ YES 136 |
|---|---|---|---|

| RAPIDITY NORMAL ☐ FAST↑ 137 SLOW↓ 138 | LOUDNESS NORMAL ☐ LOUD↑ 139 SOFT↓ 140 | PITCH NORMAL ☐ HIGH↑ 141 LOW↓ 142 |
|---|---|---|

| 7 | 8 | 9 | CLEAR MEM / READ | ~6-18 |
|---|---|---|---|---|
| 4 | 5 | 6 | LIST / LOGIC | ~6-14 |
| 1 | 2 | 3 | DISPLAY / DELETE | ~6-16 |
| ENTER | 0 | CLEAR KEYS | RUN / WRITE | ~6-20 |

DIAGNOSIS TABLE

| DIAGNOSIS NUMBER | NAME | LOCATION IN FILE |
|---|---|---|
| 000000 | ORAL INTAKE PERMITTED | 043-0-013 |
| 999999 | ORAL INTAKE NOT PERMITTED | 051-0-013 |
| 000003 | PNEUMONIA | 062-0-013 |
| 000032 | FEVER, MODERATE | 054-0-013 |
| 000121 | DEHYDRATION, MODERATE | 105-0-013 |
| 000138 | SHOCK | 127-0-013 |

TREATMENT MANUAL

| TREATMENT NUMBER | PATIENT WEIGHT- KILOGRAM | FIRST DOSE ONLY: | | | DAILY DOSE: | | | TOTAL # DAYS |
|---|---|---|---|---|---|---|---|---|
| | | MED# | ROUTE | AMOUNT | MED# | ROUTE | AMOUNT | |
| 1 | | | | | | | | |
| 000000 | 1-10 | 1 | IM | 1 ML | 2 | ORAL | ½ TAB q 6 H | 10 |
| | 15-100 | 1 | IM | 1 ML | 2 | ORAL | 1 TAB q 6 H | 10 |
| 999999 | 1-10 | | | | *1 | IM | 1 ML q 12 H | 10 |
| | 15-100 | | | | *1 | IM | 2 ML q 12 H | 10 |
| 2 | | | | | | | | |
| 000000 | 1-10 | 1 | IM | 2 ML | 2 | ORAL | 1 TAB q 6 H | 10 |
| | 15-100 | 1 | IM | 4 ML | 2 | ORAL | 2 TAB q 6 H | 10 |
| 999999 | 1-10 | | | | *1 | IM | 2 ML q 12 H | 10 |
| | 15-100 | | | | *3 | IM | 1.25 ML/12 H | 10 |
| 3 | | | | | | | | |
| 000000 & 999999 | 1-10 | | | | 3 | IM | 1.25 ML/ 6 H | 10 |
| | 15-100 | | | | 3 | IM | 2.5 ML/ 6 H | 10 |

*EVALUATE PATIENT ONCE EVERY 24 HOURS. WHEN ORAL INTAKE IS PERMITTED, I.E., DIAGNOSIS IS 000000, STOP THE 999999 TREATMENT SCHEDULE, AND START THE 000000 TREATMENT SCHEDULE FOR THE REMAINING NUMBER OF DAYS.

| MED# | FORM | NOTES | NAME |
|---|---|---|---|
| 1 | LIQUID | | PENICILLIN G, PROCAINE WITH ALUMINUM STEARATE SUSPENSION(USP) |
| 2 | TABLET | | PENICILLIN G |
| 3 | POWDER | ADD 3 ML STERILE WATER | PENICILLIN G, BUFFERED SODIUM, (AQUEOUS) |

FIGURE 10

| PATIENT NAME | | | | PATIENT # | | EXAM # | | FORM 1 | |
|---|---|---|---|---|---|---|---|---|---|
| SEX MALE 108 FEMALE 109 | | | | HEIGHT | | WEIGHT | | BLOOD PRESSURE | |
| AGE | | | | CM | | KG | | SYSTOLIC MM HG | DIASTOLIC MM HG |
| DAYS | | YEARS | | 30 – 104 | | 1 – 105 | | 0 – 106 | 0 – 107 |
| 1 – 100 | | 1 – 103 | | 35 – 104 | | 2 – 105 | | 20 – 106 | 20 – 107 |
| 2 – 100 | | 2 – 103 | | 40 – 104 | | 3 – 105 | | 30 – 106 | 30 – 107 |
| 3 – 100 | | 3 – 103 | | 45 – 104 | | 4 – 105 | | 40 – 106 | 40 – 107 |
| 4 – 100 | | 4 – 103 | | 50 – 104 | | 5 – 105 | | 50 – 106 | (50 – 107) |
| 5 – 100 | | (5 – 103) | | 55 – 104 | | 6 – 105 | | 60 – 106 | 60 – 107 |
| 6 – 100 | | 8 – 103 | | 60 – 104 | | 7 – 105 | | 70 – 106 | 70 – 107 |
| | | 10 – 103 | | 70 – 104 | | 8 – 105 | | (80 – 106) | 80 – 107 |
| WEEKS | | 12 – 103 | | 80 – 104 | | 9 – 105 | | 90 – 106 | 90 – 107 |
| 1 – 101 | | 14 – 103 | | 90 – 104 | | 10 – 105 | | 100 – 106 | 100 – 107 |
| 2 – 101 | | 16 – 103 | | 100 – 104 | | (20 – 105) | | 110 – 106 | 110 – 107 |
| 3 – 101 | | 20 – 103 | | 120 – 104 | | 30 – 105 | | 120 – 106 | 120 – 107 |
| | | 30 – 103 | | 140 – 104 | | 40 – 105 | | 130 – 106 | 130 – 107 |
| MONTHS | | 40 – 103 | | 160 – 104 | | 50 – 105 | | 140 – 106 | 140 – 107 |
| 1 – 102 | | 50 – 103 | | 180 – 104 | | 60 – 105 | | 160 – 106 | 160 – 107 |
| 2 – 102 | | 60 – 103 | | 200 – 104 | | 70 – 105 | | 180 – 106 | 180 – 107 |
| 3 – 102 | | 70 – 103 | | | | 80 – 105 | | 200 – 106 | 200 – 107 |
| 6 – 102 | | 80 – 103 | | | | 90 – 105 | | 220 – 106 | 220 – 107 |
| 9 – 102 | | 90 – 103 | | | | 100 – 105 | | 240 – 106 | 240 – 107 |

| CONSCIOUS | SEMI-CONSCIOUS | UNCONSCIOUS | ANKLE TENDON PINCH: | WITHDRAWAL & SOME OTHER RESPONSE | WITHDRAWAL & NO OTHER RESPONSE | NO RESPONSE |
|---|---|---|---|---|---|---|
| ☐ | 110 | 111 | | 112 | 113 | 114 |

| ALERT | DULL | SLEEPY | WHO | | WHERE | | WHEN | |
|---|---|---|---|---|---|---|---|---|
| | | | FORGET | WRONG | FORGET | WRONG | FORGET | WRONG |
| ☐ | 115 | 116 | 117 | 118 | 119 | 120 | 121 | 122 |

| CALM | ANGER | AGITATED | DEPRESSED | FEARFUL |
|---|---|---|---|---|
| ☐ | 123 | 124 | 125 | 126 |

| HALLUCINATIONS NO YES | HEARING | VISUAL | SMELL | TASTE | TOUCH |
|---|---|---|---|---|---|
| ☐ 127 | 128 | 129 | 130 | 131 | 132 |

| SPEECH YES NO | MEANING MEANINGFUL SENSELESS | WORDS CLEAR GARBLED | PAIN NO YES |
|---|---|---|---|
| ☐ 133 | ☐ 134 | ☐ 135 | ☐ 136 |

| | RAPIDITY | | | LOUDNESS | | | PITCH | |
|---|---|---|---|---|---|---|---|---|
| NORMAL | FAST ↑ | SLOW ↓ | NORMAL | LOUD ↑ | SOFT ↓ | NORMAL | HIGH ↑ | LOW ↓ |
| ☐ | 137 | 138 | ☐ | 139 | 140 | ☐ | 141 | 142 |

FIGURE 11

| PATIENT NAME | | | | PATIENT # | | EXAM # | | FORM 9 |
|---|---|---|---|---|---|---|---|---|
| BREATHING 2 - ABDOMEN - EXAM | | | | | | | | |

BREATH SOUNDS  USE DIAGRAM 1 FOR LOCATION

| NORMALLY VESICULAR ☐ | BRONCHO-VESICULAR | BRONCHIAL | NONE | | NORMALLY NONE ☐ | MOIST GURGLE | MOIST BUBBLE CRACKLE | DRY SQUEAK GROAN |
|---|---|---|---|---|---|---|---|---|
| | ___-727 | ___-728 | ___-729 | RALES | | ___-730 | (348)-731 | ___-732 |
| | ___-727 | ___-728 | ___-729 | | | ___-730 | ___-731 | ___-732 |
| EXCEPT IN AREAS # | ___-727 5 & 17 | ___-728 2 & 14 | ___-729 ___-729 | | | ___-730 ___-730 | ___-731 ___-731 | ___-732 ___-732 |

| RUBS NORMALLY NONE ☐ | WHISPER '99' | | | SPEAK '99' CHEST WALL VIBRATION ABSENT | | | | | |
|---|---|---|---|---|---|---|---|---|---|
| | NORMAL FAINT ☐ | CLEAR | NONE | BACK | | FRONT | | SIDE | |
| | | | | LEFT | RIGHT | RIGHT | LEFT | RIGHT | LEFT |
| ___-733 | | ___-734 | ___-735 | AREA MID 116-736 | 118-736 | 104-736 | 106-736 | 107-736 | 108-736 |
| ___-733 | | ___-734 | ___-735 | | | | | | |
| ___-733 | | ___-734 | ___-735 | LOW 119-736 | 120-736 | 110-736 | 111-736 | 109-736 | 112-736 |

| ABDOMINAL WALL | MOVES WITH BREATHING | | ENLARGED & BULGING | | | | HARDNESS | | |
|---|---|---|---|---|---|---|---|---|---|
| | YES ☐ | NO 2-737 | NO ☐ | MILD 2-738 | MODERATE 3-738 | SEVERE 4-738 | SOFT ☐ | TENSE 2-739 | RIGID 3-739 |

INTRA ABDOMINAL MASS  DESCRIBE ONLY 1 MASS PER LOCATION; GET LOCATION FROM DIAGRAM 1

| NONE ☐ | SIZE 0-15 CM | >15 CM | MULTIPLE | CONTOUR BUMPY | SMOOTH | HARDNESS HARD | SOFT | MOBILITY MOBILE | IMMOBILE |
|---|---|---|---|---|---|---|---|---|---|
| MASS 1 | ___-740 | ___-741 | ___-742 | ___-743 | ___-744 | ___-745 | ___-746 | ___-747 | ___-748 |
| MASS 2 | ___-740 | ___-741 | ___-742 | ___-743 | ___-744 | ___-745 | ___-746 | ___-747 | ___-748 |

ABDOMINAL TENDERNESS

| NONE ☐ | UPPER | | | LOWER | | | FLANK | | BACK PUNCH PAIN |
|---|---|---|---|---|---|---|---|---|---|
| | RIGHT | MIDDLE | LEFT | RIGHT | MIDDLE | LEFT | RIGHT | LEFT | |
| PRESSURE | 121-749 | 122-749 | 123-749 | 124-749 | 125-749 | 126-749 | 127-749 | 128-749 | R 129-749 |
| REBOUND | 121-750 | 122-750 | 123-750 | 124-750 | 125-750 | 126-750 | 127-750 | 128-750 | L 130-749 |

PERCUSSION  RANGE: DULL - RESONANT - TYMPANIC

| | UPPER | | | LOWER | | | FLANK | | SHIFTING DULLNESS FLANK |
|---|---|---|---|---|---|---|---|---|---|
| | RIGHT | MIDDLE | LEFT | RIGHT | MIDDLE | LEFT | RIGHT | LEFT | |
| DULL | 121-751 | 122-751 | 123-751 | 124-751 | 125-751 | 126-751 | 127-751 | 128-751 | R 127-751 |
| TYMPANIC | 121-752 | 122-752 | 123-752 | 124-752 | 125-752 | 126-752 | 127-752 | 128-752 | L 128-752 |

BOWEL SOUNDS

| BUBBLE GURGLE | TINKLE | GROAN SQUEAK | 0/2 MIN | 0/1 MIN | FREQUENCY PER MINUTE 1-4 | 5-8 | >8 |
|---|---|---|---|---|---|---|---|
| 1-753 | 2-753 | 3-753 | 1-754 | 2-754 | 3-754 | 4-754 | 5-754 |

| SOFTEST | SOFT | LOUDNESS MIDDLE | LOUD | LOUDEST | 1-2 | LENGTH IN SECONDS 3-5 | 6-10 | >10 |
|---|---|---|---|---|---|---|---|---|
| 1-755 | 2-755 | 3-755 | 4-755 | 5-755 | 1-756 | 2-756 | 3-756 | 4-756 |

FIGURE 12

DEMONSTRATION CASE

| | COMPUTER PRINTED TAPE | | CLINICAL EXPLANATION |
|---|---|---|---|
| LINE # | | | |
| 1 | 510.3 | 000 + | 5 year old child |
| 2 | 201.05 | 003 + | 20 kilograms weight |
| 3 | 801.06 | 006 + | 80 mm systolic blood pressure |
| 4 | 501.07 | 011 + | 50 mm diastolic blood pressure |
| 5 | 204. | 014 + | 38.6 °C temperature, medium fever |
| 6 | 130.369 | 017 + | 130 heart beats per minute, wrist pulse |
| 7 | 470.1 | 022 + | 18 breaths per minute |
| 8 | 270.7 | 025 + | Difficulty with breathing observed |
| 9 | 348.731 | 030 + | Rales(bubbling sounds) heard with stethoscope in right lower front of chest |
| 10 | 221. | 033 + | Surface dryness inside mouth observed |
| 11 | 267. | 036 + | Decreased skin turgor(tenting) observed |
| ➡12 | •••••••••• | E | ➡Dots separate clinical data and results ➡ |
| 13 | 999999 | | Treatment: NOTHING BY MOUTH |
| 14 | •••• | | -Dots separate each clinical condition |
| 15 | 213 | | Treatment: ANTIPYRETIC |
| 16 | 214 | | Treatment: MODERATE EXTERNAL COOLING |
| 17 | 000032 | | Clinical Condition: Medium Fever |
| 18 | •••• | | -Dots separate each clinical condition |
| 19 | 1 | | Treatment: PENICILLIN G |
| 20 | 115 | | Treatment: EXPECTORANT |
| 21 | 400 | | Treatment: SMEAR SPUTUM ON GLASS SLIDE |
| 22 | 000003 | | Clinical Condition: Pneumonia |
| 23 | •••• | | -Dots separate each clinical condition |
| 24 | 270 | | Treatment: INTRAVENOUS (I.V.) FLUIDS |
| 25 | 000121 | | Clinical Condition: Moderate Dehydration |
| 26 | •••• | | -Dots separate each clinical condition |
| 27 | 216 | | Treatment: VASOPRESSOR ADDED TO I.V. FLUIDS |
| 28 | 217 | | Treatment: PLACE PATIENT HORIZONTAL-FEET UP |
| 29 | 218 | | Treatment: PLACE BLANKET OVER PATIENT |
| 30 | 000138 | | Clinical Condition: Shock |
| 31 | •••• | | -Dots separate each clinical condition |
| 32 | •••• | | -Dots-the following 4 rows of dots indicate that the analysis is completed |
| 33 | •••• | | |
| 34 | •••• | | |
| 35 | •••• | | |

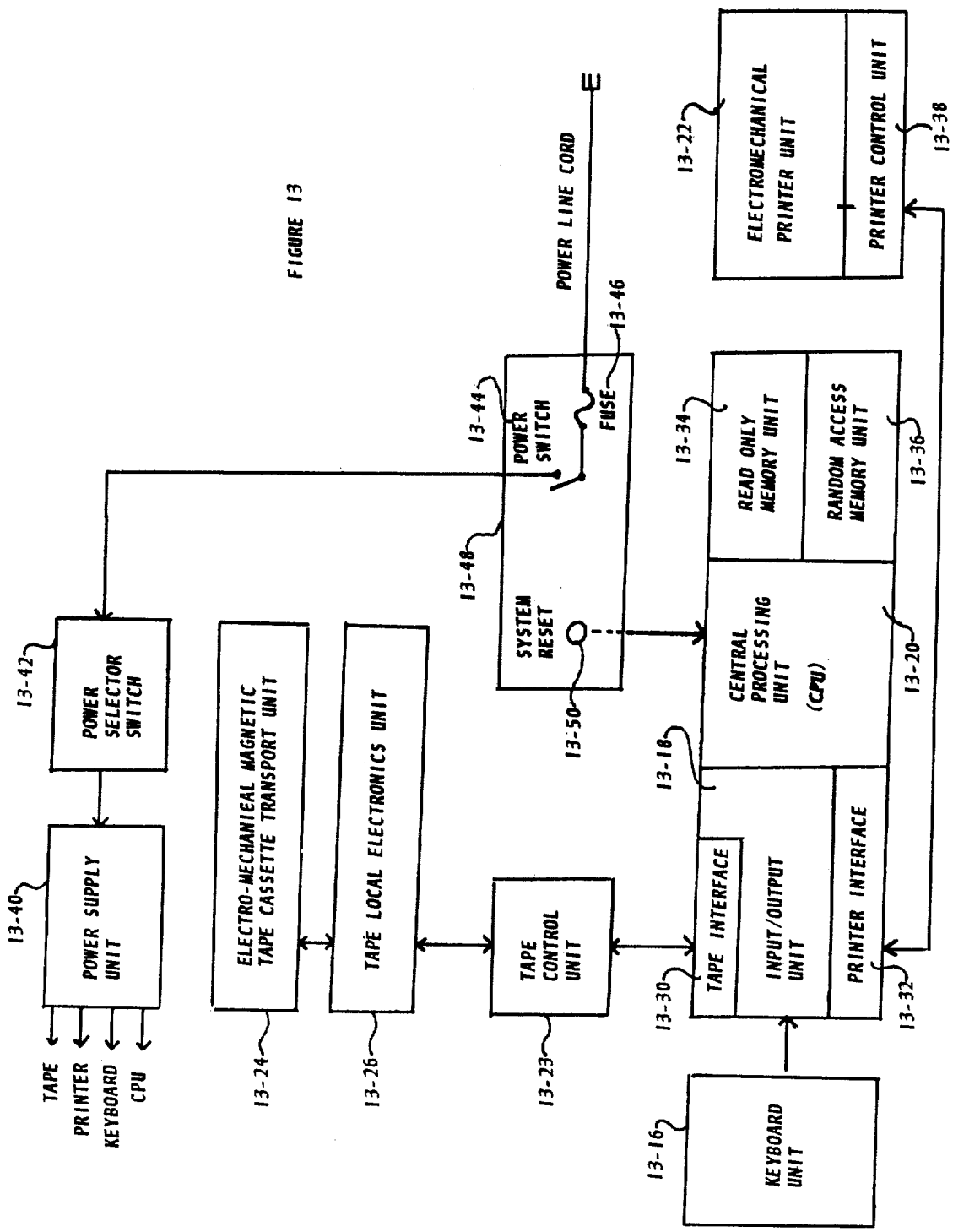

FIG. 17

MEDICAL DISEASE FILE WORKSHEET

DISEASE NAME: (PNEUMONIA) PULMONARY CONSOLIDATION-OPEN BRONCHUS-FEBRILE

DIAGNOSIS NUMBER: 000003

STORAGE LOCATION NUMBER: 062-0-013

| DESCRIPTION<br>Symptoms & Findings:<br>Logic: Treatment: Diagnosis | CODE | DESCRIPTION<br>Symptoms & Findings:<br>Logic: Treatment: Diagnosis | CODE |
|---|---|---|---|
| OR | 09 | | 347 |
| FEVER SLIGHT | 203 | | 348 |
| MEDIUM | 204 | | 349 |
| HIGH | 205 | | 350 |
| HIGHEST | 206 | THORAX-BACK | 240 |
| OR | 09 | | 242 |
| BREATH RATE/MIN 14-18 | 4701 | | 243 |
| 19-22 | 5701 | | 245 |
| 23-30 | 6701 | | 246 |
| >30 | 7701 | | 247 |
| OR | 09 | MLOF | 03 |
| DIFFICULTY BREATHING-INSP. MILD | 2707 | OR | 09 |
| MODERATE | 3707 | BREATH SOUNDS-BRONCHVESICLAR | 000 727 |
| SEVERE | 4707 | BRONCHIAL | 000 727 |
| -EXP. MILD | 5707 | WHISPER CLEAR | 000 734 |
| MODERATE | 6707 | RALES GURGLE | 000 730 |
| SEVERE | 7707 | RALES-CRACKLE | 000 731 |
| MLON | 02 | MLEN | 05 |
| THORAX-FRONT & SIDE | 340 | EOS | 11 |
| | 341 | PENICILLIN | 1 |
| | 342 | EXPECTORANT | 115 |
| | 344 | MICROSCOPIC SPUTUM-AFB | 400 |
| | 345 | PULM. CONSOL. OP. BR. FEB. | 000 003 |
| | 346 | ITS | BL |
| | | IDS | 01 |

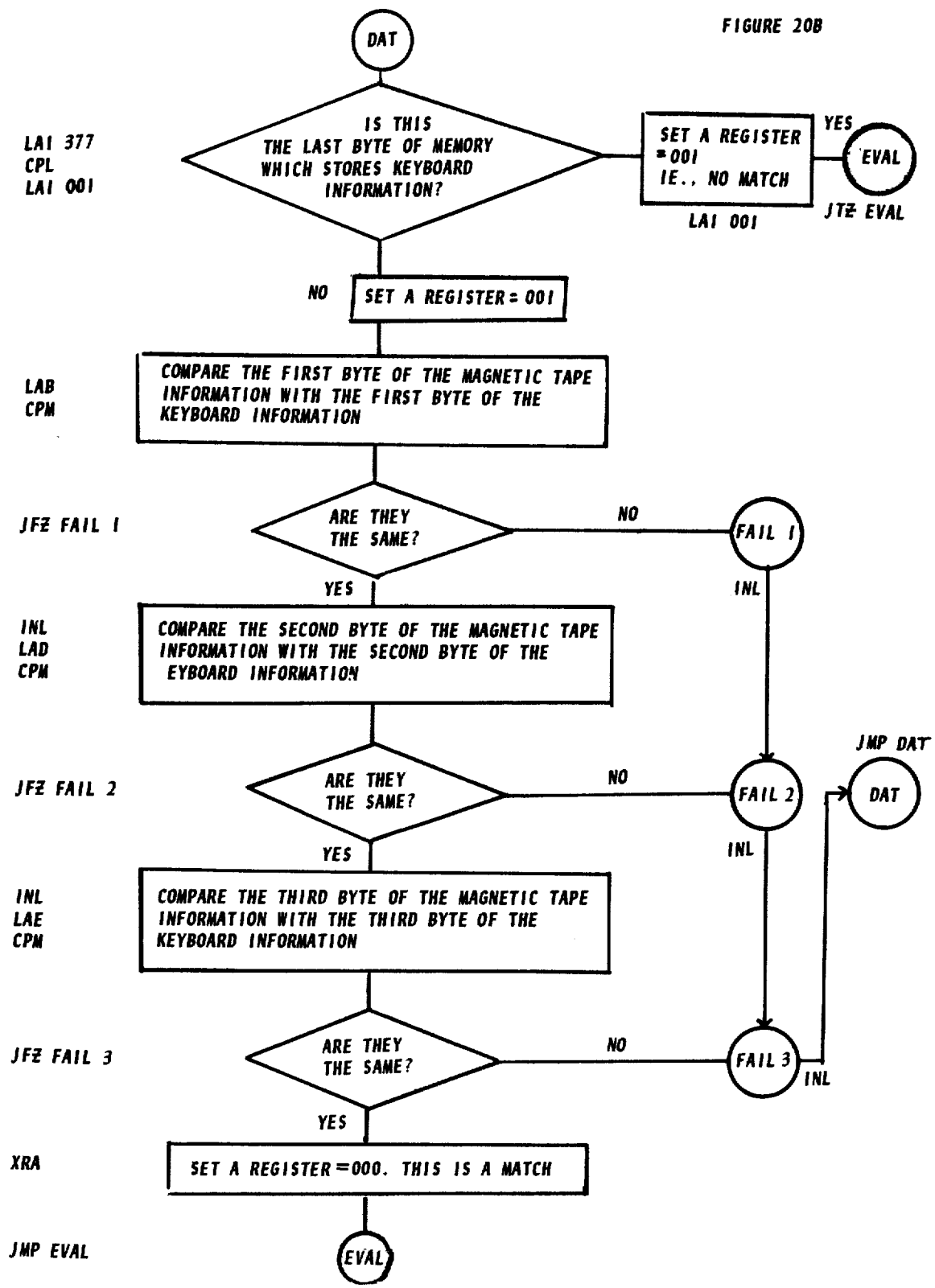

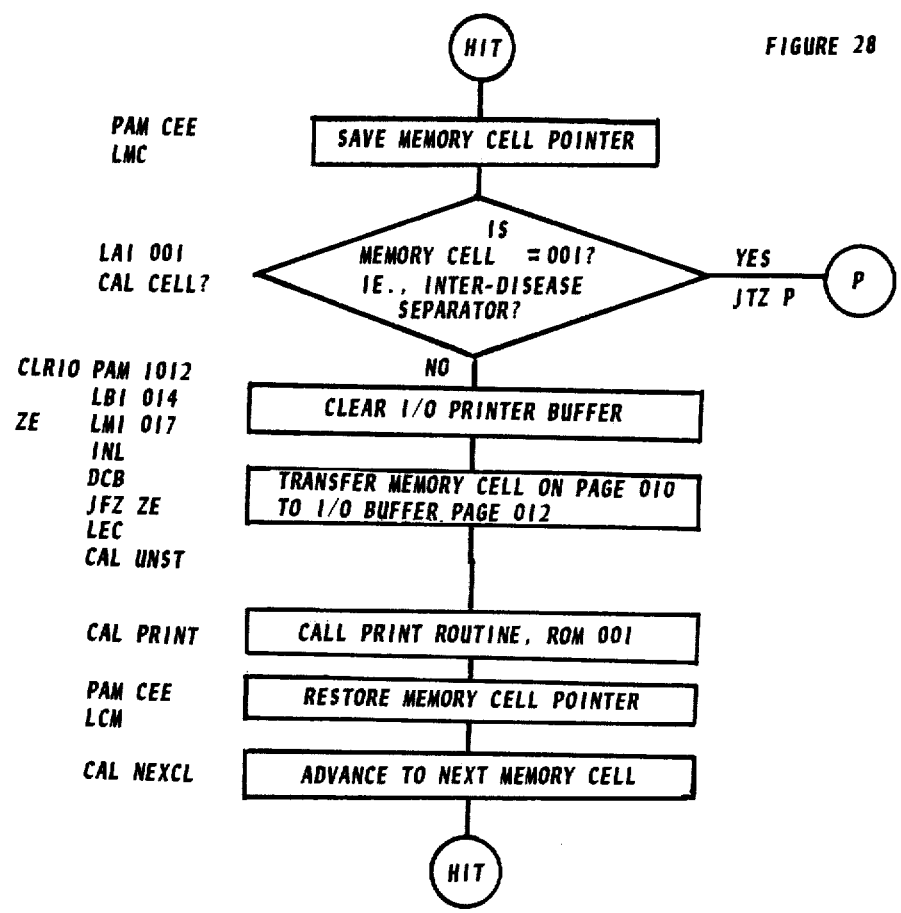

MEDICAL DIAGNOSTIC COMPUTER

BACKGROUND OF THE INVENTION

1. Field of the Invention

This invention is in the field of computers and more particularly relates to a method and apparatus for computer-aided medical care.

2. Description of the Prior Art

The use of computers to process medical data has long been known. For example, the electrical signals generated by various sensors such as electrocardiographs, electroencephalographs and other sensors may be filtered, conditioned and verified by analog or digital computers which serve as signal processing filters. Clearly, such signal conditioners prepare the medical data for use in subsequent diagnosis, but such devices do not participate in the diagnostic algorithm.

The prior art is replete with input/output terminals for accessing computer-based central medical data records from multiple remote locations. While such terminals and data storage systems are of great practical value, it is clear that they also do not perform the same function as the present invention, namely diagnosis.

As used below, diagnosis means the determination of the patient's malady based on an evaluation of a set of symptoms and findings.

In U.S. Pat. No. 3,830,228, issued Aug. 20, 1974 to Foner, a portable biophysiological information processing device is shown which may be used to make electrocardiograms and the like. The device appears to convert electrical signals from the sensors into a meaningful form which is then printed out. No details of the information processing technique are given. The device contains "deducing means for deducing an intelligent interpretation of the information". Means for detecting erroneous inputs and conveying warning messages to the operator regarding difficulties with poor contact, noise, interference, ranging error, etc. are provided. It appears that this invention falls into the category of signal processing devices mentioned above. The patents to be discussed below all deal with the generation and use of computerized medical records.

Rowland, in U.S. Pat. No. 3,737,863, issued June 5, 1973 shows a medical testing system including a computer connected to receive test results from sensors and to print out a test report of the tests performed.

A computerized file for handling and processing all of the patient records in a hospital is shown in U.S. Pat. No. 3,872,448, issued Mar. 18, 1975 to Mitchell, Jr. The computer contains a number of files, such as patient description file, transaction file, test library file and past results file. These files, in the central computer, may be easily accessed from multiple stations within the hospital.

Likewise, a complete computer-based medical record system is described in U.S. Pat. Nos. 3,566,365; 3,693,166; 3,725,866; and, 3,839,708. As pointed out above, none of these systems have the capability of examining the test results and data stored in them to determine the nature of the patient's problem.

SUMMARY OF THE INVENTION

The system of the present invention utilizes a dedicated computer to diagnose the patient's illness and to indicate a treatment for it. As distinguished from prior art systems, the present invention does not merely aid diagnosis, it performs the diagnosis and issues specific treatment instructions.

Traditionally, a diagnosis is made by a trained medical practioner, at the side of the patient and responsive not only to quantitatively determined symptoms and findings but to the qualitative and intangible aspects of the patient's overall condition. This traditional approach is preferred wherever trained medical practitioners are available. Unfortunately, trained medical practitioners are not available in many parts of the world and in the absence of such medical practitioners, many thousands of people die each year. This is the problem with which the inventor has been concerned, and his solution is based on the belief that computerized health care is better than no health care at all.

The system of the present invention is designed to be operated by a health auxiliary or paramedic to provide medical care in those areas where trained medical practitioners are not available. Alternatively, the system of the present invention permits relatively unskilled paramedics to augment the trained medical practitioners where they are in short supply.

The computer is used for the diagnosis analysis, but the system of the present invention further includes a set of medical forms and diagrams and a treatment and diagnosis manual. The medical forms and diagrams are printed with numeric codes for each disease finding. The health auxiliary or paramedic performs a physical examination of the patient and records the findings in the forms. Thereafter, he enters the numerical codes corresponding to each of the findings into the computer portion of the system through a small keyboard. The computer performs the diagnosis analysis and responds by printing a series of numbers on a paper tape. These numbers indicate in coded form the diagnosis and the specific treatments to be administered to the patient. The health auxiliary enters the treatment manual with these numbers and performs the procedures indicated therein. Hence, the health auxiliary must be literate in the language in which the medical forms and the treatment manual are written, but the inputs and outputs of the computer, being numerical in form, are independent of the language being used. Thus, the same computer program and input/output format can be used in all countries. This is a tremendous advantage in that the health auxiliary does not have to spend his training program time in learning a new language, but instead can concentrate on learning the objective skills required. These skills include the gathering of physical examination findings and the adminstration of simplified treatments. It is anticipated that these skills can be effectively taught to the auxiliary in period of six months or less. The difficult task of teaching integrated diagnostic thought is not required.

The diagnostic and treatment instruction codes printed by the computer are based on a comparative analysis between the numerically coded physical examination findings entered by the health auxiliary and the numerically coded disease definitions stored in the system by the medical authorities.

The number and kinds of disease definitions and treatment instructions stored in the system are easily edited and controlled by the medical authorities. This gives great flexibility and growth potential to the system as well as control over the treatment which the auxiliary is permitted to perform. Thus, the system can be modified, as the skill of the paramedic grows, to permit him to perform more difficult treatments. Further, the treatments themselves can be changed and updated in accordance with the latest medical thought and the availability of medicines. Likewise, the medical forms can be revised as the health auxiliary becomes more skilled.

The storage unit for the disease definitions and treatment codes is a small removable magnetic tape cassette. Implementation of changes made by the medical authorities is accomplished by the distribution of the new cassette to the health auxiliaries in the remote areas. The old cassette is reusable.

The use of the system makes it possible for the medical authorities to reliably extend a segment of the physician's diagnostic ability to the health auxiliary. This is accomplished by taking maximum advantage of the objective physical findings obtained by the auxiliary. New diseases and treatments can be added to the magnetic tape without the absolute necessity to change the basic skills of the auxiliary. Even in those special circumstances where it is important to have the auxiliary learn to gather a new piece of objective information or learn to perform a new treatment skill, the necessary changes may be accomplished without disruption to the existing system.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 2 is a block diagram of the components of the health care system of the present invention;

FIG. 3 is a facsimile of a Medical Form on which symptoms and findings are indicated in the system of the present invention and from which corresponding code numbers are obtained;

FIG. 6 is a diagram of the keyboard of the Medical Diagnostic Computer of the present invention;

FIG. 8 is a facsimile of a page of a diagnosis table in the Diagnosis and Treatment Manual used with the system of the present invention;

FIG. 9 is a facsimile of a treatment table portion of the Diagnosis and Treatment Manual used in the system of the present invention;

FIG. 10 is a facsimile of a Medical Form showing how certain findings are entered onto the form;

FIG. 11 is a Medical Form showing how a site-related symptom is entered onto the form;

FIG. 12 is a facsimile of an output tape produced by the Medical Diagnostic Computer during a sample problem;

FIG. 13 is a functional component block diagram of the Medical Diagnostic Computer used in the system of the present invention;

FIG. 17 is a facsimile of a Medical Disease File Worksheet used in the system of the present invention;

FIGS. 18A, 18B, 19, 20A, 20B, 21, 22, 23 and 24 are flow charts showing the operations performed by the Medical Diagnostic Computer during the ANAL portion of the program; and FIGS. 25, 26, 27 and 28 are flow charts showing the operations performed by the Medical Diagnostic Computer during the SONE portion of the program.

DESCRIPTION OF THE PREFERRED EMBODIMENT

SYSTEM OVERVIEW

Figure 1:
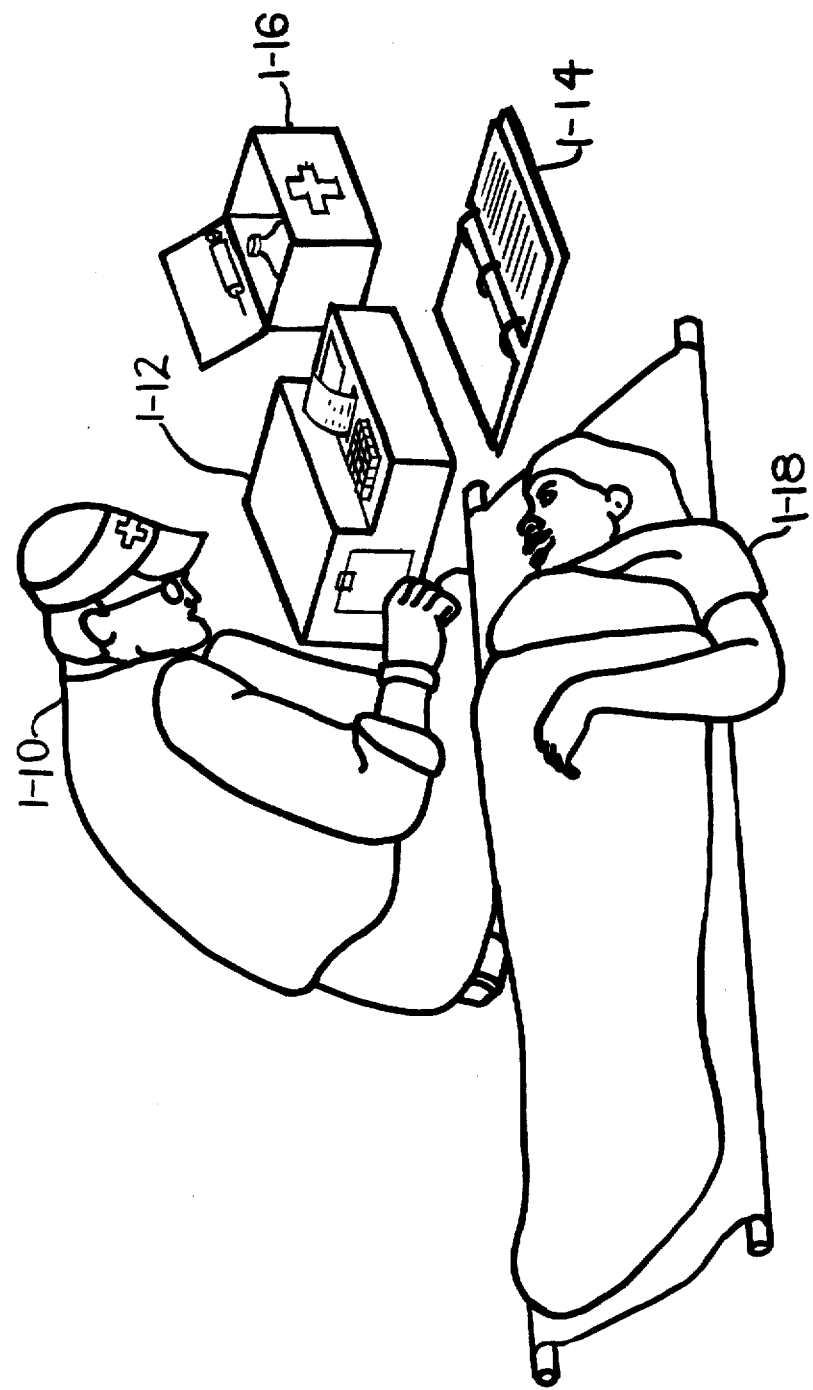
FIG. 1 is a diagram showing the major components of the health care system of the present invention and the use of the system.

Referring now to the drawings, the use of the system is shown in FIG. 1. Adequate health care is not available in the majority of the areas of the world. In many remote areas, trained medical practitioners, if available at all, may be separated from the patients by several days' journey. The system of the present invention is designed to alleviate this condition by augmenting the efforts of the trained medical practitioners through the use of health auxiliaries or paramedics. It is not contemplated that these health auxiliaries would perform complicated operations and the like, but with a relatively short training program they should be able to administer medications and a number of simple treatments.

The health auxiliary 1-10 of FIG. 1 would, according to the present invention, carry with him the Medical Diagnostic Computer 1-12, printed materials 1-14, and a kit of medical supplies 1-16, permitting the health auxiliary to diagnose and treat the patient 1-18.

The printed materials 1-14 include two categories of instructions. In the first category is a series of Medical Forms and Diagrams in which numerical codes are assigned to a rather wide variety of symptoms and findings. The second category of printed materials is collectively referred to as a Diagnosis and Treatment Manual, which tells the appropriate diagnosis and treatment corresponding to numerical codes printed out by the Medical Diagnostic Computer 1-12. All of the printed material 1-14 is in a language which the health auxiliary 1-10 can understand.

It is contemplated that the printed materials 1-14 will be translated into a number of languages for use in various parts of the world. An important feature of the present invention is that all communication to and from the Medical Diagnostic Computer 1-12 is independent of the language used in the printed materials 1-14, being in numerical form in one embodiment of the invention. As a result, a standardized Medical Diagnostic Computer 1-12 can be used throughout the world, and such computers are interchangeable on a worldwide basis.

Figure 4:
FIG. 4 is a facsimile of another Medical Form used for recording symptoms and findings in the system of the present invention and from which corresponding code numbers are obtained.

FIG. 2 is a block diagram showing the flow of information in the health care system of the present invention. The health auxiliary 2-10 obtains a number of medical items of information from the patient 2-12 and records these symptoms and findings on the Medical Forms and Diagrams 2-14. As used in this specification, medical items is a general term which includes symptoms, findings, historical facts, medical test results, and the like without limitation. FIGS. 3 and 4 show typical Medical Forms, and they can be seen to provide for the recording of a large number of possible symptoms and findings. As can be seen from FIG. 3, a different code number is associated with each possible symptom or finding. In the following description, these code numbers are referred to as "numerical disease codes", and should be distinguished from "diagnosis" and "treatment" codes described below.

Figure 5:
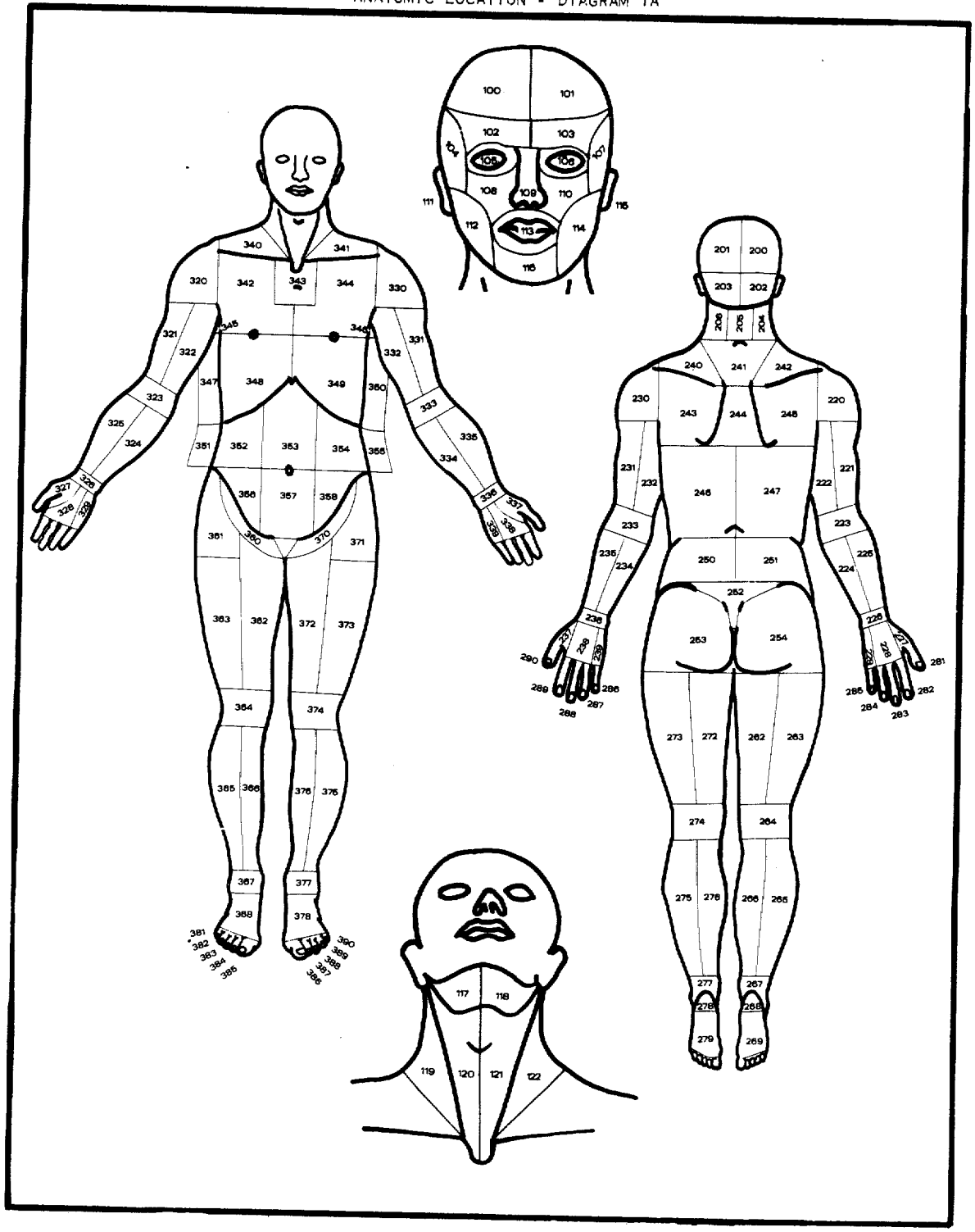
FIG. 5 is a facsimile of a Medical Diagram Form used to provide numerical codes corresponding to various bodily locations.

A number of Medical Diagrams accompany the Medical Forms. A typical Medical Diagram is shown in FIG. 5. The Medical Diagrams provide numerical codes corresponding to various areas of the surface of the human body. These codes are inserted on the Medical Forms where required to define the portion of the body in which certain symptoms or findings are observed. These portions of the body will generally be referred to as sites in the following description.

Referring to FIG. 2, it has been seen that the health auxiliary 2-10 enters the symptoms and findings onto the Medical Forms and Diagrams 2-14, from which the health auxiliary can read the numerical disease codes corresponding to the various symptoms and findings that were present. Thereafter, the health auxiliary 2-10 enters the numerical disease codes into the Medical Diagnostic Computer 2-30 by way of a keyboard 2-16. In a preferred embodiment, the keyboard 2-16 includes ten keys numbered from zero through nine along with six control keys, as shown in FIG. 6. The use of these control keys will be described in greater detail below. Electrical impulses from the keyboard 2-16 transmit the numerical disease codes entered to the input/output unit 2-18 of the computer.

Although the keyboard of FIG. 6 is used in a preferred embodiment, other embodiments employ other types of keyboard, for example: alpha-numeric-function or symbolic-matrix. In still other embodiments, the keyboard may be replaced by a cathode ray tube-light pencil input device.

After each numerical input has been entered on the keyboard, the health auxiliary depresses the "ENTER" key 6-10 of FIG. 6 which causes the printer 2-22 to print the coded information item just entered. The printer 2-22 in response to depression of the "ENTER" key 6-10 of FIG. 6 successively prints each numerical disease code on a tape of which the tape 7-10 of FIG. 7 is typical, on the left hand portion 7-12 of it.

Thus, it is seen that the purpose of the printer is to display the outputs and to display input data for verification and alteration. Although a printer is used in the preferred embodiment described here, in other embodiments a cathode ray tube or light emitting device or liquid crystal display could be used.

If it is found that an error has been made in a particular entry before the "ENTER" key has been depressed, the health auxiliary presses the "CLEAR KEYS" keys 6-12 of FIG. 6 to remove the incorrect entry, and thereafter re-enters the correct code by depressing the numerical keys again. If the error is found after the "ENTER" key has been depressed, the health auxiliary can delete the erroneous entry by entering the associated item identification number from the right hand column of the tape (7-14 of FIG. 7), then twice depressing the "DISPLAY/DELETE" key 6-16 of FIG. 6.

Figure 7:
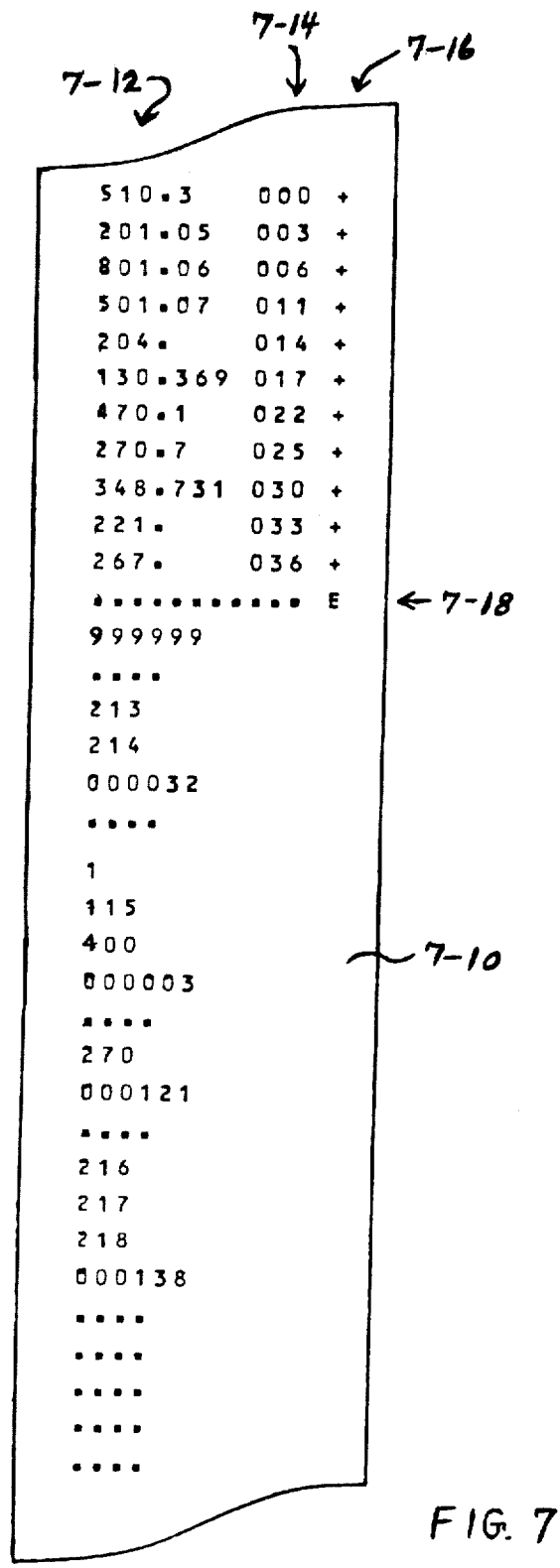
FIG. 7 is a facsimile of an output tape produced by the Medical Diagnostic Computer of the present invention.

The "ENTER" key 6-10 is depressed after the entry of each code, to obtain the printed verification on the tape 7-10 of FIG. 7. For each numerical disease code, the printer prints out in a right-hand column 7-14 of FIG. 7 a three-digit octal number indicating the location in the computer memory at which the numerical disease code was stored by the computer. Further, the printer also prints out a column 7-16 of symbols, each indicating that the accompanying numerical disease code has indeed been entered by the machine.

It is possible to cause the printer to display individual numerical disease codes by depressing the numeric keys for the three-digit octal machine location code, and then depressing the "DISPLAY" key 6-16 of FIG. 6. The entire set of numerical disease codes which have been entered can be printed by depressing the "LIST" key 6-14 of FIG. 6 immediately after any individual numerical disease code has been displayed as described in the preceding sentence.

All of the numerical disease codes can be deleted from the memory of the computer at one time by depressing the "CLEAR MEM" key 6-18 of FIG. 6.

After all of the numerical disease codes have been entered and checked for correctness, the analysis of the patient information is initiated by depressing the "RUN" key 6-20 of FIG. 6.

The first printer response is a full line of eleven dots and the symbol E, 7-18 of FIG. 7. This line of dots separates the numerical disease code and location information printed above it from the results of the analysis which are to be printed below it.

For each disease identified by the machine, the printer will show one or more numerically coded treatment instructions and a numerically coded diagnosis. The treatment code is one-to-five digits long, while each diagnosis code is six digits long. Each disease is separated from the other by a row of four dots.

When the analysis is complete, the printer prints four rows of four dots. The paper tape 7-10 of FIG. 7 is then torn from the printer and it can be used as a permanent record. The machine, upon completing the analysis automatically resets itself to accept medical information items for the next patient. A detailed example showing the interpretation of the various items on a tape similar to that of FIG. 7 will be given below.

Returning to the diagram of FIG. 2, the health auxiliary 2-10 after taking the paper tape from printer 2-22 consults the Diagnosis and Treatment Manual 2-26 to determine the name of the illness and the instructions for its treatment, which are printed therein in the language of the health auxiliary. The health auxiliary then effectuates the treatment instructions by giving the indicated treatment to the patient 2-12.

FIG. 8 shows a typical page from the Diagnosis and Treatment Manual, specifically a Table which gives the names corresponding to the six-digit diagnosis codes on the tape. FIG. 9 is a typical page of the Diagnosis and Treatment Manual, specifically a page giving treatment instructions corresponding to certain of the one-to-five digit treatment codes printed on the tape.

FIGS. 10, 11 and 12 relate to an example illustrating the use of the Medical Diagnostic Computer.

In the example, the patient is five years old and weighs 20 kilograms. His systolic blood pressure is 80 millimeters Hg. and his diastolic blood pressure is 50 millimeters Hg. The patient has a medium fever of 38.6 degrees Celsius and the mucous membranes of his mouth are dry. His peripheral pulse is 130 per minute. The patient is breathing 18 times per minute. Mild difficult in breathing is experienced by the patient and by the use of a stethoscope the health auxiliary is able to hear a moist bubbling sound (rale) at the right front bottom of the patient's rib cage.

FIG. 10 shows how the health auxiliary would note the symptoms and findings into the Medical Forms by drawing a circle around the appropriate symptoms and findings. It is not necessary for the health auxiliary to decide which symptoms and findings to enter in the Forms. The Medical Forms indicate the examinations to be made. The computer can easily cope with a surplus of information, but cannot be expected to yield the correct diagnosis and treatment unless the key symptoms and findings associated with the illness have been entered.

The order in which the examinations are performed is immaterial as is the order in which the numerical codes circled on FIG. 10 are entered into the keyboard. It is desirable to use a systematic order to prevent oversights and omissions.

FIG. 11 is another one of the ten Medical Forms. The presence of rales is noted on the Form of FIG. 11. In general, both the qualitative sound of the rales and the portion of the body in which they are heard may be of significance to a proper diagnosis. In the present example, a moist bubbling sound was heard in the right front bottom of the patient's rib cage. The Medical Forms permit the location of the symptom or finding to be input to the computer for all symptoms that are location-pertinent. Therefore, the health auxiliary consults a Medical Diagram such as that shown above in FIG. 5 to determine a code number—in this case 348—specific to the part of the body where the symptom or finding was noted. Referring to FIG. 11, the health auxiliary has inserted the numerical code 348 in front of the code 731 which is generic to moist, bubbling or crackling rales.

FIG. 12 shows the tape produced by printer 2-22 of FIG. 2 in the present example. The first line on the tape shows the entry corresponding to the age shown circled on FIG. 10. Likewise, the patient's weight (20 kilograms) is shown on the second line of the tape. The symptom on line 11 of the tape, tenting skin, has a numerical code 267, which was found from one of the forms not included herein.

The ninth item on the tape shows the entry for the rales condition circled on FIG. 11.

The numbers on the right hand side of the tape opposite the symptom and finding codes, are octal numbers identifying the storage location within the computer at which the numerical codes are stored. It is desirable to note these locations in case the health auxiliary wishes to retrieve a previously stored input for the purpose of modifying or deleting it, as described above.

After the "RUN" key 6-20 of FIG. 6 has been depressed, the computer first prints out the row of dots shown on the twelfth line of the tape shown in FIG. 12. This row of dots is used to separate the input data from the output data. Following the row of dots, the computer prints out the first diagnosis, in this case the six digits "999999" shown on line 13. It is clearly a diagnosis code number, because it includes six digits. "999999" means that oral intake of medications is not permitted for this patient. The Treatment Manual is organized in two sections, the "999999" section (oral intake not permitted) and the "000000" section (oral intake permitted).

The various diagnoses made by the machine are separated on the tape by rows of four dots, as seen at lines 14, 18, 23, and 26 of the exemplary tape shown in FIG. 12. In that example, the treatments for the second diagnosis are shown on lines 15 and 16 of the tape. Lines 15 and 16 are obviously treatment codes because they contain less than six digits. The datum on line 17 is a six digit number and by reference to the DIAGNOSIS TABLE of FIG. 8 is found to denote "fever, moderate". The treatment for the fever is indicated by the numerical treatment codes 213 and 214 found respectively on lines 15 and 16. From the TREATMENT MANUAL, the health auxiliary can determine that "213" means to give aspirin, while the treatment "214" means to apply moderate external cooling to the patient. Likewise, the treatments corresponding to the third, fourth and fifth diagnoses (pneumonia, dehydration, and shock, respectively) can also be found by the health auxiliary in the Diagnosis and Treatment Manual.

The health auxiliary gets the treatment numbers from the computer printed tape. If as in the example of FIG. 12, the computer printed tape showed a treatment number 1 (penicillin), and a diagnosis number 999999 (oral intake not permitted), the health auxiliary would find treatment number 1 in the Treatment Manual and use the 999999 section, as shown in FIG. 9.

For a patient weighing 20 kilograms, the health auxiliary would use the dosage schedule on the 15-100 kilogram line. This line gives him all the information he needs to know.

The health auxiliary uses medication number 1, and injects it into the patient's muscles using a hypodermic syringe filled with 2 ml. of medicine, every 12 hours for a period of 10 days. As soon as it is possible for the patient to take medications by mouth, the injections are stopped.

As described above, the four rows of four dots each, shown at lines 32-35 on the exemplary tape of FIG. 12, indicate that no further diagnoses are forthcoming from the computer.

Referring again to the basic system diagram shown in FIG. 2, it can be seen that the Medical Diagnostic Computer 2-30 includes in addition to the keyboard 2-16 and printer 2-22, a magnetic tape cassette unit 2-24 on which disease-defining information is stored. In other embodiments, the memory function may be performed by a "floppy disc", charge coupled diode memory, or other suitable memory device. The information on the tape and the information entered through the keyboard 2-16 is input to the central processor unit 2-20 through the input/output unit 2-18, for storage in the internal memory 2-32 of the computer.

In the central processor unit 2-20, the disease definitions stored on the magnetic tape cassette unit 2-24 and now in the memory are compared with the symptoms and findings of the patient which were entered through keyboard 2-16. The diagnosis rendered by the central processor unit 2-20 is output to the printer 2-22 through the input/output unit 2-18. The computer further includes a self-contained power supply 2-28 and, in addition, is adapted for use with available electric power sources.

In the following paragraphs, the structure and operation of the components comprising the Medical Diagnostic Computer 2-30 will be described in greater detail.

THE COMPUTER

Clearly, the Medical Diagnostic Computer described in the above section can be implemented in any number of ways. In this section the structure of the computer in a preferred embodiment will be described to provide a meaningful basis for understanding the programing of the computer, which will be described in a later section. No attempt will be made to describe the structural details of the computer in greater detail than the block diagram level. This is because the structure of the computer is not deemed to be novel, and because almost all of the components are commercially available and well known to those skilled in the art.

FIG. 13 shows the components of the Medical Diagnostic Computer 2-30 of FIG. 2 in greater detail. The keyboard unit 13-16, the printer unit 13-22, the input/output unit 13-18 and the central processor unit 13-20 are substantially the same as the components 2-16, 2-22, 2-18 and 2-20 of FIG. 2. The magnetic tape cassette unit 2-24 of FIG. 2 is seen to include the tape transport unit 13-24, the tape local electronics unit 13-23 and a tape control unit 13-28. The input/output unit 2-18 of FIG. 2 is seen to include a tape interface portion 13-30 and a printer interface portion 13-32. The memory 2-32 of FIG. 2 is seen to include a read only memory 13-34 and a random access memory 13-36. Printer unit 2-22 of FIG. 2 is seen to include a printer control portion 13-38. Finally, the power supply 2-28 of FIG. 2 is seen to include a power supply unit 13-40, a power selector switch 13-42, a power switch 13-44, and a fuse 13-46. The latter two units are mounted on a control panel 13-48 which includes a system reset switch 13-50.

Power selector switch 13-42 permits the Medical Diagnostic Computer to operate from line currents of various voltages or from an internal battery (not shown). All external power flows into the computer through the power switch 13-44 and the fuse 13-46.

The system reset switch 13-50 is used to return the computer to an initial condition, deleting all information that might be stored in the computer at the time the switch is activated.

Figure 14:
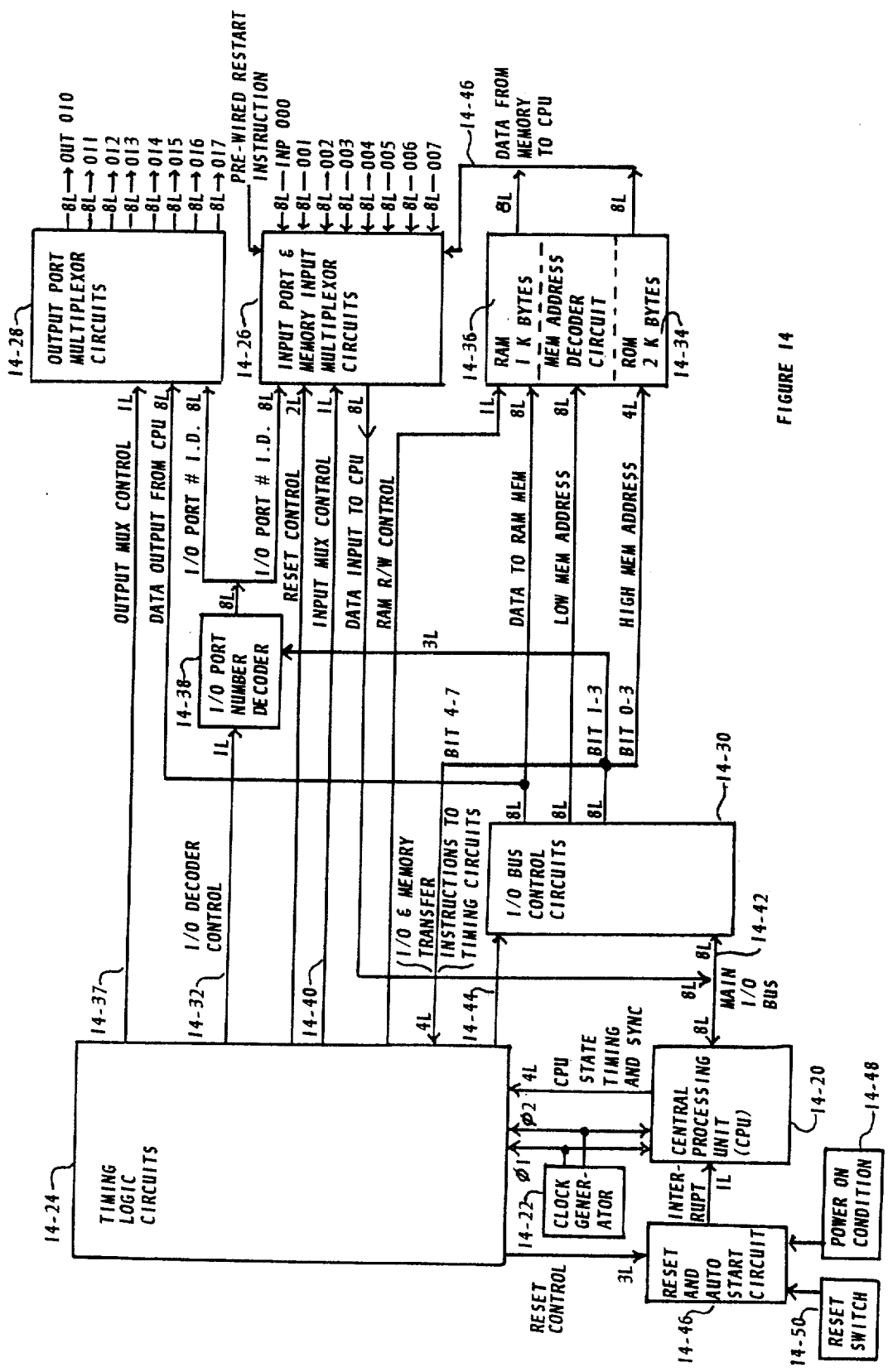
FIG. 14 is a block diagram showing the basic system control circuits of the Medical Diagnostic Computer of the present invention.
Figure 15:
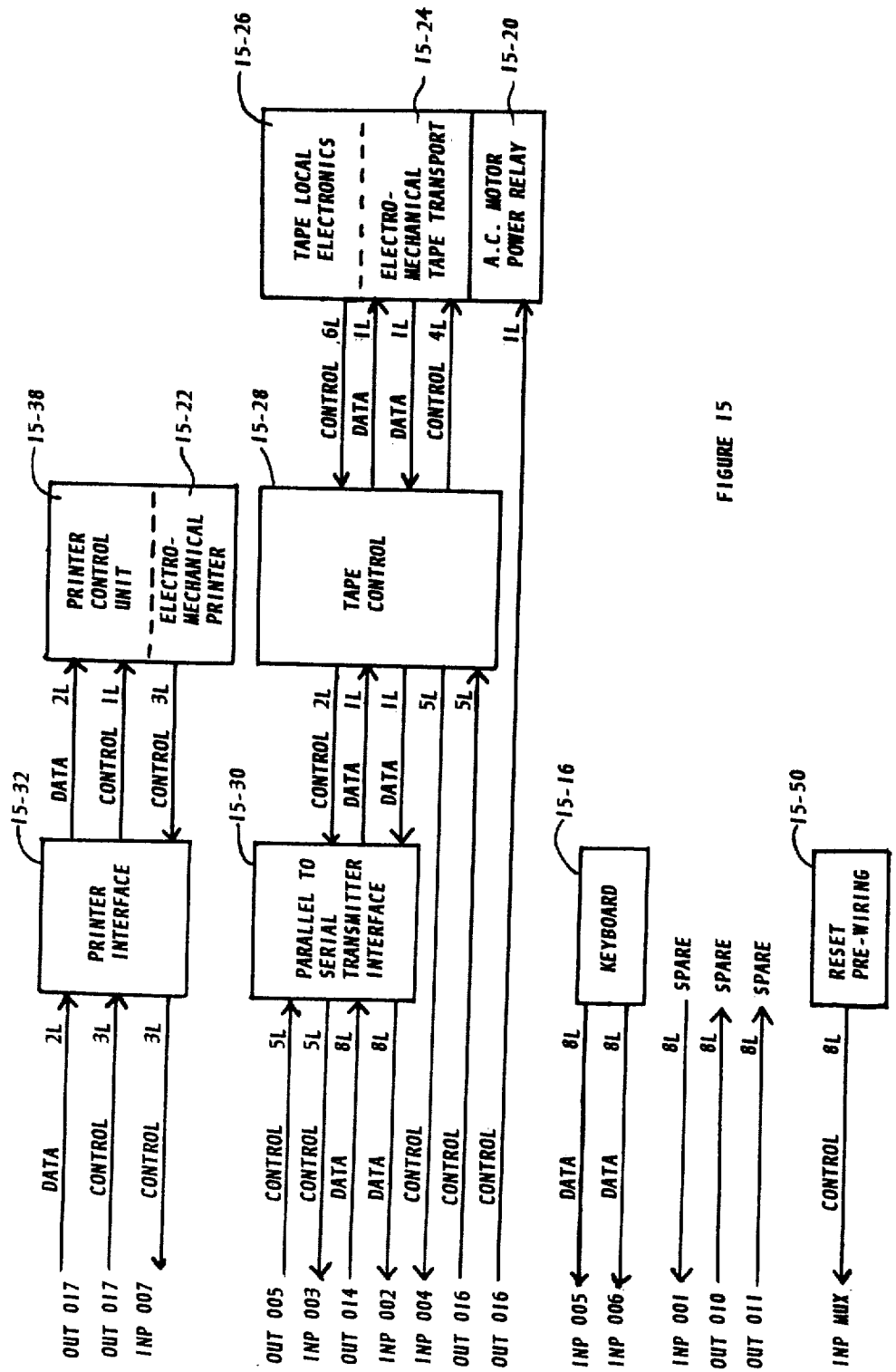
FIG. 15 is a block diagram showing the input-output and peripheral interface circuits of the Medical Diagnostic Computer.

The components shown in FIG. 13 and their detailed interconnections are shown more clearly in FIGS. 14 and 15. FIG. 14 is a system control circuit showing the interconnections required to control the computer and FIG. 15 shows how the peripheral units are interconnected to the computer.

In a preferred embodiment, the medical diagnostic computer is built around a commercially available microprocessor, the INTEL 8008. The detailed structure and operation of that unit as well as techniques for utilizing the microprocessor in a computer are contained in the publication, "MCS-8 Micro Computer Set—8008 User's Manual", published by the manufacturer INTEL in 1973. Further useful descriptive information pertaining to microcomputers and their use is given in "An Introduction to Microcomputers" (no author) published by Adam Osborne and Associates, Inc., 2950 Seventh Street, Berkeley, California 94710. These publications are incorporated by reference herein.

The 8008 is an 8-bit parallel central processor unit, very well known to those skilled in the art. The processor 14-20 of FIG. 14 communicates over an 8-bit bus which is used for both data and addresses. The CPU 14-20 is driven by a two-phase clock generator 14-22, which generates two trains of non-overlapping pulses of the same frequency. These two pulse trains control the entire operation of the computer.

The output signals $\Phi_1$ and $\Phi_2$ of the clock generator 14-22 control the timing logic circuits 14-24 to produce a variety of control signals at appropriate predetermined times, directed to the components being controlled, namely, the input port circuits 14-26, the output port circuits 14-28, the random access memory 14-36, the read only memory 14-34 and the input/output bus control circuits 14-30.

Information flows through the computer in the form of 8 parallel binary signals simultaneously present at any instant on the 8 lines of the main data bus. Signals from the timing logic circuits 14-24 determine whether the information on the main bus is data being processed or an address to which the data is being directed. The timing logic circuits 14-24 also control which of the other components are gated to the main bus for receiving or transmitting information over it. Thus, for example, a signal on line 14-32, produced by the timing logic circuits 14-24 activates the input/output port number decoder 14-38 to permit a signal on one of 8 lines indicating which input or output port is to be gated to the main bus. Other signals on lines 14-37 and 14-40 determine whether the information on the bus is to be an input or an output, and determine the time when the port is gated to the main bus.

As will be seen below in the discussion of the programing of the computer, each instruction may include 8 bits of data and 14 bits of address. Since only 8 bits of information can be present on the bus at any one time, it is clear that 3 cycles of operation may be necessary to tranmit 8 bits of data along with the accompanying 14 bits of address. Input/output bus control circuits 14-30 in effect multiplex the information present on main bus 14-42 onto buses dedicated to the 8 bits of data, the low portion of the memory address, and the high portion of the memory address in succession, in response to activating signals on line 14-44 generated by timing logic circuits 14-24. Data being read from random access memory 14-36 or read only memory 14-34 is returned to the central processor unit 14-20 through bus 14-42 and one of the input ports of the input port circuits 14-26.

As shown in FIG. 14, there are 8 input ports numbered in octal notation from 000 to 007, each connected to an 8-line bus. Likewise, there are 8 output ports each connected to an 8-line bus, and numbered in octal notation from 010 through 017. These input and output buses lead to the perihperal units: the printer, the magnetic tape memory, and the keyboard.

The computer also includes reset and automatic start circuit 14-46 to provide for synchronous starting and stopping of the central processor unit 14-20. The system may be reset by activating reset switch 14-50. Power on conditioning circuit 14-48 and reset and auto-start circuit 14-46 also reset the system when power is applied.

Turning now to FIG. 15, the electro-mechanical printer 15-22 in a preferred embodiment is a commercially available device known as a FACIT 4508. Printer control unit 15-38 is a part of the printer unit as purchased. Printer interface 15-32 conditions the output information from the computer to render it compatable with the printer.

In a preferred embodiment, keyboard 15-16 is a commercially available unit known as a MICROSWITCH 16SW3-14. It communicates with the computer by 16 dedicated lines.

In a preferred embodiment, the memory of the computer is enhanced by the provision of an external memory in the form of a magnetic tape cassette. During the operation of the computer, data is read into the computer from the tape and is read out of the computer for storage on the magnetic tape.

In a preferred embodiment, the electro mechanical magnetic tape transport unit 15-24 is a commerically available item known as a REDACTRON 100. The operation of the tape transport unit 15-24 is directed by the tape local electronics 15-26 and mechanically driven by a motor through AC motor power relay 15-20. The tape local electronics unit 15-26 is part of the tape unit purchased. Both the control and data information from the computer is conditioned by parallel-to-serial transmitter interface 15-30 and tape control 15-28 to render it usable by the tape unit. Those same units also condition the data and control signals read from the tape and used as inputs to the computer.

In a preferred embodiment, read only memory (ROM) 13-34 of FIG. 13 consists of eight 256-word chips which are erasable and reprogrammable. In a preferred embodiment the chips are of a type available commercially as an INTEL 1702A.

The random access memory (RAM) 13-36 of FIG. 13 in a preferred embodiment consists of 8 chips, each capable of storing 1024 bits, to provide a 1024 word random access memory. In a preferred embodiment, commercially available chips, known as INTEL 2102, are used.

Figure 16:
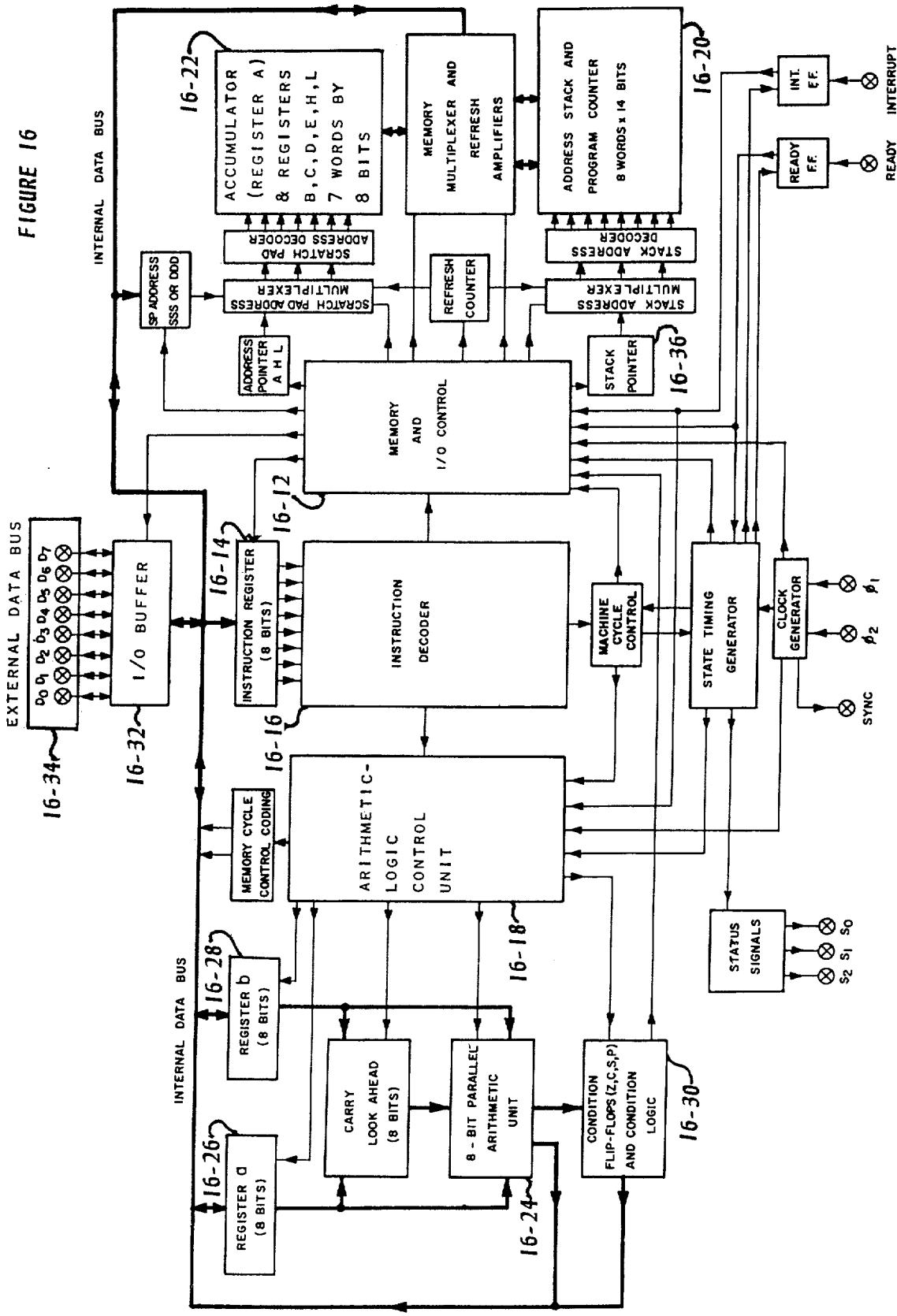
FIG. 16 is a block diagram of the microcomputer portion of the Medical Diagnostic Computer of the present invention.

FIG. 16 is a block diagram of the INTEL 8008 central processor unit. Instructions are fetched from the memory 6-12, stored in the instruction register 6-14 and decoded by the instruction decoder 16-16 for control of both the memory 6-12 and the arithmetic-logic control unit 16-18.

Two separate dynamic memories are used in the INTEL 8008: the pushdown address stack 16-20 and a scratch pad memory 16-22. The memories and registers shown in FIG. 16 are internal to the central processing unit 13-20 of FIG. 13 and must not be confused with the read only memory 13-34 and the random access memory 13-36, also of FIG. 13. The internal memories are automatically refreshed at predetermined intervals.

The address stack 16-20 contains eight 14-bit registers providing storage for 8 lower and 6 higher order address bits in each register. One register is used as the program counter (storing the effective address) and the other 7 permit address storage for nesting of subroutines up to 7 levels. A nested subroutine is a subroutine that has been called by another subroutine. The stack 16-20 automatically stores the content of the program counter at the time when a subroutine is called and automatically restores the program counter upon the execution of the last instruction in a subroutine. The addresses of the subroutines to be called may be nested and the registers of the stack are used as a last-in first-out pushdown stack.

A three bit stack pointer 16-36 is used to designate the present location of the program counter. When the capacity of the stack is exceeded the address pointer recycles and the content of the lowest level register is destroyed. The program counter is incremented immediately after the lower order address bits are sent out. The higher order address bits are sent out at a later time and are incremented if a carry resulted from operations performed on the higher order address bits. The 14-bit program counter enables direct addressing of 16 K memory locations. Through the use of bank switching, memory may be indefinitely expanded.

The scratch pad memory 16-22 contains the accumulator (A register) and six additional 8-bit registers designated B, C, D, E, H and L. All arithmetic operations use the accumulator as one of the operands. All registers are independent and may be used for temporary storage. In the case of instructions which require operations with a register in external memory, scratch pad registers H and L provide indirect addressing capability: register L contains the 8 lower-order bits of address and register H contains the 6 higher-order bits of address.

All arithmetic and logical operations (ADD, ADD with carry, SUBTRACT, SUBTRACT with borrow, AND, EXCLUSIVE OR, OR, COMPARE, INCREMENT, DECREMENT) are carried out in the 8-bit parallel arithmetic unit 16-24, which includes carry-look-ahead logic. Two temporary registers, register "a" 16-26 and register "b" 16-28 are used to store the accumulator and operand for all operations of the arithmetic-logic unit. In addition, they are used for temporary address and data storage during intraprocessor transfers.

Four control bits, zero flip-flop (z), carry flip-flop (c), sign flip-flop (s), and parity flip-flop (p) are set as the result of each aritmetic and logical operation.

These condition flip-flops and logic 16-30 provide conditional branching capability through instructions to call a subroutine, jump to another location in the program, or return to a previous location on condition. Also, the carry bit c provides the capability to do multiple-precision binary arithmetic.

The central processor unit is linked to the rest of the computer through input/output buffer 16-32, which contains 8 bidirectional buffers which connect the central processor unit to the 8 lines of the external data bus.

BASIC INSTRUCTION SET

Data in the INTEL 8008 central processor unit is stored in the form of 8-bit binary integers. All data transfers to the external data bus are in that same format.

The program instructions may be one, two, or three bytes (words) in length. Multiple-byte instructions must be stored in successive words in the program memory. The instruction formats then depend on the particular operation executed. Each memory address in the ROM or RAM memories is 14 bits in length, so that when an instruction references a memory address, two words of the instruction are used in giving the memory address reference. The various scratch pad memories within the processor, because they are fewer in number, can be addressed by a 3-binary-digit code, which forms part of some instructions. These scratch pad registers, referred to in the basic instruction set as source index registers or destination index registers are designated as follows A (accumulator, 000), B (001), C (010), D (011), E (100), H (101), L (110). As described above, registers of the external memory are addressed by the contents of scratch pad registers H and L.

In the following paragraphs, each of the instructions in the basic instruction set will be explained in detail. For each instruction, a 3-letter mnemonic assembly language instruction is given in the SIM 8 Hardware Assembler language. Next, the instruction is shown in binary form (1 or more 8-digit words) and finally, a complete functional definition is given for each instruction in the repertoire.

The following symbols are used in explaining the instructions:

| Symbols | Meaning |
|---|---|
| <B2> | Second byte of the instruction |
| <B3> | Third byte of the instruction |
| r | One of the scratch pad register references: A, B, C, D, E, H, L |
| c | One of the following flag flip-flop references: C, Z, S, P |
| $C_4C_3$ | Flag flip-flop codes    Condition for True |
|    00 | carry    Overflow, underflow |
|    01 | zero    Result is zero |
|    10 | sign    MSB of result is "1" |
|    11 | parity    Parity of result is even |
| M | Memory location indicated by the contents of registers H and L |
| ( ) | Contents of location or register |
| Λ | Logical product |
| | Exclusive "or" |

-continued

| Symbols | Meaning |
|---|---|
| V | Inclusive "or" |
| $A_m$ | Bit m of the A register |
| STACK | Instruction counter (P) pushdown register |
| P | Program Counter |
| ← | Is transferred to |
| XXX | A "don't care" |
| SSS | Source register for data |
| DDD | Destination register for data |

| Register # (SSS or DDD) | Register Name |
|---|---|
| 000 | A |
| 001 | B |
| 010 | C |
| 011 | D |
| 100 | E |
| 101 | H |
| 110 | L |

The basic set of instructions is as follows:

INDEX REGISTER INSTRUCTIONS

LOAD DATA TO INDEX REGISTERS - One Byte
Data may be loaded into or moved between any of the index registers, or memory registers.

Lr₁r₂    11    DDD    SSS    ($r_1$) ← ($r_2$) Load register $r_1$ with the content of $r_2$.
(one cycle - PCI)    The content of $r_2$ remains unchanged. If SSS = DDD the instruction is a NOP (no operation).

LrM    11    DDD    111    (r) ← (M) Load register r with the content of the
(two cycles - PCI/PCR)    memory location addressed by the contents of registers H and L. (DDD ≠ 111 - HALT instr.)

LMr    11    111    SSS    (M) ← (r) Load the memory location addressed by
(two cycles - PCI/PCW)    the contents of registers H and L with the content of register r. (SSS ≠ 111 - HALT instr.)

LOAD DATA IMMEDIATE - Two Bytes
A byte of data immediately following the instruction may be loaded into the processor or into the memory LrI    00    DDD    110    (r) ← <B2> Load byte two of the instruction into
(two cycles -    <B2>    register r.
PCI/PCR)

LMI    00    111    110    (M) ← <B2> Load byte two of the instruction into
(three cycles -    <B2>    the memory location addressed by the contents of
PCI/PCR/PCW)    registers H and L.

INCREMENT INDEX REGISTER - One Byte

INr    00    DDD    000    (r) ← (r) + 1. The content of register r is incremented by
(one cycle - PCI)    one. All of the condition flip-flops except carry are affected by the result. Note that DDD ≠ 000 (HALT instr.) and DDD ≠ 111 (content of memory may not be incremented).

DECREMENT INDEX REGISTER - One Byte

DCr    00    DDD    001    (r) ← (r) − 1. The content of register r is decremented
(one cycle - PCI)    by one. All of the condition flip flops except carry are affected by the result. Note that DDD ≠ 000 (HALT instr.) and DDD ≠ 111 (content of memory may not be decremented).

ACCUMULATOR GROUP INSTRUCTIONS

Operations are performed and the status flip-flops, C, Z, S, P, are set based on the result of the operation.
Logical operations (NDr, XRr, ORr) set the carry flip-flop to zero. Rotate operations affect only the carry flip-flop. Two's complement subtraction is used.
ALU INDEX REGISTER INSTRUCTIONS - One Byte
(one cycle - PCI)
Index Register operations are carried out between the accumulator and the content of one of the index registers (SSS = 000 thru SSS = 110). The previous content of register SSS is unchanged by the operation.

ADr    10    000    SSS    (A) ← (A) + (r) Add the content of register r to the content of register A and place the result into register A.

ACr    10    001    SSS    (A) ← (A) + (r) + (carry) Add the content of register r and the contents of the carry flip flop to the content of the A register and place the result into Register A.

SUr    10    010    SSS    (A) ← (A) − (r) Subtract the content of register r from the content of register A and place the result into register A. Two's complement subtraction is used.

SBr    10    011    SSS    (A) ← (A) − (r) − (borrow) Subtract the content of register r and the content of the carry flip-flop from the content of register A and place the result into register A.

NDr    10    100    SSS    (A) ← (A) Λ (r) Place the logical product of the register A and register r into register A.

XRr    10    101    SSS    (A) ← (A)    (r) Place the "exclusive - or" of the

-continued

| | | | | |
|---|---|---|---|---|
| ORr | 10 | 110 | SSS | content of register A and register r into register A. $(A) \leftarrow (A) \vee (r)$ Place the "inclusive - or" of the content of register A and register r into register A. |
| CPr | 10 | 111 | SSS | $(A) - (r)$ Compare the content of register A with the content of register r. The content of register A remains unchanged. The flag flip-flops are set by the result of the subtraction. Equality or inequality is indicated by the zero flip-flop. Less than or greater than is indicated by the carry flip-flop. |

ALU OPERATIONS WITH MEMORY - One Byte
(two cycles - PCI/PCR)
Arithmetic and logical operations are carried out between the accumulator and the byte of data addressed by the contents of registers H and L.

| | | | | |
|---|---|---|---|---|
| ADM | 10 | 000 | 111 | $(A) \leftarrow (A) + (M)$ ADD |
| ACM | 10 | 001 | 111 | $(A) \leftarrow (A) + (M) + $ (carry) ADD with carry |
| SUM | 10 | 010 | 111 | $(A) \leftarrow (A) - (M)$ SUBTRACT |
| SBM | 10 | 011 | 111 | $(A) \leftarrow (A) - (M) - $ (borrow) SUBTRACT with borrow |
| NDM | 10 | 100 | 111 | $(A) \leftarrow (A) \wedge (M)$ Logical AND |
| XRM | 10 | 101 | 111 | $(A) \leftarrow (A)$ (M) Exclusive OR |
| ORM | 10 | 110 | 111 | $(A) \leftarrow (A) \vee (M)$ Inclusive OR |
| CPM | 10 | 111 | 111 | $(A) - (M)$ COMPARE |

ALU IMMEDIATE INSTRUCTIONS - Two Bytes
(two cycles - PCI/PCR)
Arithmetic and logical operations are carried out between the accumulator and the byte of data immediately following the instruction.

| | | | | |
|---|---|---|---|---|
| ADI | 00 | 000 $<B_2>$ | 100 | $(A) \leftarrow (A) + <B_2>$ ADD |
| ACI | 00 | 001 $<B_2>$ | 100 | $(A) \leftarrow (A) + <B_2> + $ (carry) ADD with carry |
| SUI | 00 | 010 $<B_2>$ | 100 | $(A) \leftarrow (A) - <B_2>$ SUBTRACT |
| SBI | 00 | 011 $<B_2>$ | 100 | $(A) \leftarrow (A) - <B_2> - $ (borrow) SUBTRACT with borrow |
| NDI | 00 | 100 $<B_2>$ | 100 | $(A) \leftarrow (A) \wedge <B_2>$ Logical AND |
| XRI | 00 | 101 $<B_2>$ | 100 | $(A) \leftarrow (A)$ $<B_2>$ Exclusive OR |
| ORI | 00 | 110 $<B_2>$ | 100 | $(A) \leftarrow (A) \vee <B_2>$ Inclusive OR |
| CPI | 00 | 111 $<B_2>$ | 100 | $(A) - <B_2>$ COMPARE |

ROTATE INSTRUCTIONS - One Byte
(one cycle - PCI)
The accumulator content (register A) may be rotated either right or left, around the carry bit or through the carry bit. Only the carry flip-flop is affected by these instructions; the other flags are unchanged.

| | | | | |
|---|---|---|---|---|
| RLC | 00 | 000 | 010 | $A_{m+1} \leftarrow A_m, A_0 \leftarrow A_7,$ (carry) $\leftarrow A_7$ Rotate the content of register A left one bit. Rotate $A_7$ into $A_0$ and into the carry flip-flop. |
| RRC | 00 | 001 | 010 | $A_m \leftarrow A_{m+1}, A_7 \leftarrow A_0,$ (carry) $\leftarrow A_0$ Rotate the content of register A right one bit. Rotate $A_0$ into $A_7$ and into the carry flip-flop. |
| RAL | 00 | 010 | 010 | $A_{m+1} \leftarrow A_m, A_0 \leftarrow$ (carry), (carry) $\leftarrow A_7$ Rotate the content of Register A left one bit. Rotate the content of the carry flip-flop into $A_0$. Rotate $A_7$ into the carry flip-flop. |
| RAR | 00 | 011 | 010 | $A_m \leftarrow A_{m+1}, A_7 \leftarrow$ (carry), (carry) $\leftarrow A_0$ Rotate the content of register A right one bit. Rotate the content of the carry flip-flop into $A_7$. Rotate $A_0$ into the carry flip-flop. |

PROGRAM COUNTER AND STACK CONTROL INSTRUCTIONS

JUMP INSTRUCTIONS - Three Bytes
(three cycles - PCI/PCR/PCR)
Normal flow of the microprogram may be altered by jumping to an address specified by bytes two and three of an instruction.

| | | | | |
|---|---|---|---|---|
| JMP (Jump Unconditionally) | 01 | XXX $<B_2>$ $<B_3>$ | 100 | $(P) \leftarrow <B_3> <B_2>$ Jump unconditionally to the instruction located in memory location addressed by byte two and byte three. |
| JFc (Jump if Condition False) | 01 | 0C$_4$C$_3$ $<B_2>$ $<B_3>$ | 000 | If (c) = 0, $(P) \leftarrow <B_3> <B_2>$. Otherwise, $(P) = (P) + 3$. If the content of flip-flop c is zero, then jump to the instruction located in memory location $<B_3> <B_2>$; otherwise, execute the next instruction in sequence. |
| JTc (Jump if Condition True) | 01 | 1C$_4$C$_3$ $<B_2>$ $<B_3>$ | 000 | If (c) = 1, $(P) \leftarrow <B_3> <B_2>$. Otherwise, $(P) = (P) + 3$. If the content of flip-flop c is one, then jump to the instruction located in memory location $<B_3> <B_2>$; otherwise, execute the next instruction in sequence. |

CALL INSTRUCTIONS - Three Bytes
(three cycles - PCI/PCR/PCR)
Subroutines may be called and nested up to seven levels.

| | | | | |
|---|---|---|---|---|
| CAL (Call subroutine | 01 | XXX $<B_2>$ | 110 | (Stack) $\leftarrow$ (P), (P) $\leftarrow <B_3> <B_2>$. Shift the content of P to the pushdown stack. Jump unconditionally to the |

-continued

| | | | | |
|---|---|---|---|---|
| Unconditionally) | | $<B_3>$ | | instruction located in memory location addressed by byte two and byte three. |
| CFc (Call subroutine if Condition False) | 01 | $0C_4C_3$ $<B_2>$ $<B_3>$ | 010 | If (c) = 0, (Stack) ← (P), (P) ← $<B_3>$ $<B_2>$. Otherwise, (P) = (P) + 3. If the content of flip-flop c is zero, then shift contents of P to the pushdown stack and jump to the instruction located in memory location $<B_3>$ $<B_2>$; otherwise, execute the next instruction in sequence. |
| CTc (Call subroutine if Condition True) | 01 | $1C_4C_3$ $<B_2>$ $<B_3>$ | 010 | If (c) = 1, (Stack) ← (P), (P) ← $<B_3>$ $<B_2>$. Otherwise, (P) = (P) + 3. If the content of flip-flop c is one, then shift contents of P to the pushdown stack and jump to the instruction located in memory location $<B_3>$ $<B_2>$; otherwise, execute the next instruction in sequence. |

In the above JUMP and CALL instructions $<B_2>$ contains the least significant half of the address and $<B_3>$ contains the most significant half of the address. Note that $D_6$ and $D_7$ of $<B_3>$ are "don't care" bits since the CPU uses fourteen bits of address.

RETURN INSTRUCTIONS - One Byte
(one cycle - PCI)
A return instruction may be used to exit from a subroutine; the stack is popped-up one level at a time.

| | | | | |
|---|---|---|---|---|
| RET | 00 | XXX | 111 | (P) ← (Stack). Return to the instruction in the memory location addressed by the last value shifted into the pushdown stack. The stack pops up one level. |
| RFc (Return Condition False) | 00 | $0C_4C_3$ | 011 | If (c) = 0, (P) ← (Stack); otherwise, (P) = (P) + 1. If the content of flip-flop c is zero, then return to the instruction in the memory location addressed by the last value inserted in the pushdown stack. The stack pops up one level. Otherwise, execute the next instruction in sequence. |
| RTc (Return Condition True) | 00 | $1C_4C_3$ | 011 | If (c) = 1, (P) ← (Stack); otherwise, (P) = (P) + 1. If the content of flip-flop c is one, then return to the instruction in the memory location addressed by the last value inserted in the pushdown stack. The stack pops up one level. Otherwise, execute the next instruction in sequence. |

RESTART INSTRUCTION - One Byte
(one cycle - PCI)
The restart instruction acts as a one byte call on eight specified locations of page 0, the first 256 instruction words.

| | | | | |
|---|---|---|---|---|
| RST | 00 | AAA | 101 | (Stack) ← (P), (P) ← (000000 00AAA000) Shift the contents of P to the pushdown stack The content, AAA, of the instruction register is shifted into bits 3 through 5 of the P-counter. All other bits of the P-counter are set to zero. As a one-word "call", eight eight-byte subroutines may be accessed in the lower 64 words of memory. |

INPUT/OUTPUT INSTRUCTIONS

One Byte
(two cycles - PCI/PCC)
Eight input devices may be referenced by the input instruction

| | | | | |
|---|---|---|---|---|
| INP | 01 | 00M | MM1 | (A) ← (input data lines). The content of register A is made available to external equipment at state T1 of the PCC cycle. The content of the instruction register is made available to external equipment at state T2 of the PCC cycle. New data for the accumulator is loaded at T3 of the PCC cycle. MMM denotes input device number. The content of the condition flip-flops, S, Z, P, C, is output on $D_0$, $D_1$, $D_2$, $D_3$ respectively at T4 on the PCC cycle. |

Twenty-four output devices may be referenced by the output instruction.

| | | | | |
|---|---|---|---|---|
| OUT | 01 | RRM | MM1 | (Output data lines) ← (A). The content of register A is made available to external equipment at state T1 and the content of the instruction register is made available to external equipment at state T2 of the PCC cycle. RRMMM denotes output device number (RR ≠ 00). |

MACHINE INSTRUCTION

HALT INSTRUCTION - One Byte
(one cycle - PCI)

| | | | | |
|---|---|---|---|---|
| HLT | 00 11 | 000 or 111 | 00X 111 | On receipt of the Halt Instruction, the activity of the processor is immediately suspended in the STOPPED state. The content of all registers and memory is unchanged. The P counter has been updated and the internal dynamic memories continue to be refreshed. |

Four additional instructions are provided to simplify the assembly process. These instructions are "pseudo operators" because they are not included in the basic instruction set. These four instructions provide for name address assignment, memory block address assignment, a double register load for the H and L registers, and termination of each pass of the assembly, respectively.

The instruction "PAM" will assemble as two instructions, "LHI" followed by an "LLI". Its operand field will be interpreted as two 3-digit octal values. The first and second values specify the LHI and LLI operand fields, respectively.

The instruction "ADR" is non-executable and may appear anywhere in a program except the first instruction. The address specified in the operand field will be assigned to the name specified in the instruction. With this instruction, names may be assigned to external subroutines and input/output units.

The instruction "LOC" is non-executable and must only appear after the last executable instruction. It is used to reserve blocks of memory locations directly after the assembled programs and to assign a name to the first location. The name field should contain the desired name and the operand field should contain two 3-digit octal numbers to indicate the length of the array. For example, the number 001000 would reserve 256 locations and the number 000377 would reserve 255 locations.

If the instruction "END" is encountered by the assembler, it will terminate the pass in process.

To this point in the description, it has been possible to discuss the medical diagnostic computer and its operation independently of the specific details of the computer program that is to be executed. In the following sections, the algorithm to be implemented and the specific computer program for implementing it will be described.

STORAGE ALLOCATIONS

As described above, the read only memory consists of 8 chips, each capable of storing 256 words. These chips are programable in that predetermined words can be loaded into the ROM by use of a special device (not part of the computer) known as a ROM-PROGRAMER. Once the desired predetermined words have been read into the ROM, they remain permanently fixed in the ROM regardless of how many times they are read out. The only way the words read into the ROM can be altered is by erasing them, which is accomplished by irradiating the ROM chip with ultraviolet light.

Although the computer of the preferred embodiment contains 8 of the 256 word chips, only 3 of the chips are used in implementing the Medical Diagnostic Computer. The chips actually used are referred to as Pages 000, 001 and 002.

Page 000 of the ROM is used to store the portion of the program that operates the cassette drive. Page 001 is used to store the portion of the program that operates the printer. Page 002 is used to store a portion of the program related to the printer. Thus, the ROM's are used only to store the relatively unchanging portions of the program that enable the Medical Diagnostic Computer to control the magnetic tape memory and the printer.

The random access memory, as described above, consists of 8 chips each capable of storing 1024 bits. Consequently, the total capacity of the RAM is 1024 words. The 8 chips are connected so as to provide for 4 RAM memories each of 256 words. The four RAM memories are referred to as Pages 010, 011, 012, and 013. During the course of a run, each of the pages 010, 011, and 012 may contain various portions of the program. That is, a portion of the program may be read into one of the pages of the RAM and after it has been executed, a different portion of the program may be read into the same RAM. As will be seen below, the program comprises a moderate number of subroutines, and none of the subroutines exceeds 256 words in length. Page 013 of the RAM is always reserved for inputs from the Keyboard.

Data is stored on the magnetic tape in related groups referred to as blocks. Initially, parts of the program have been stored in the three pages of ROM and on the first few blocks of the magnetic tape. The parts of the program on the magnetic tape are transferred at the start of each run into appropriate pages of the RAM. The remainder of the magnetic tape contains the medical disease files, that is, the numerical code numbers corresponding to the symptoms and findings which define various diseases. During the course of a run, the medical diagnostic computer compares the symptoms and findings corresponding to each of the diseases in the medical disease file with the symptoms and findings observed in the patient.

The disease definitions are entered into the magnetic tape in numerical form. The numerical codes for the various symptoms and findings are taken from the Medical Disease Forms such as those shown above in FIGS. 3, 4, and 5.

According to the present invention, specific diseases are defined by expressing the various combinations of symptoms and findings in conjunction with the use of the logic functions AND, NOT, OR, and EXLUSIVE OR. These logic functions have been assigned mnemonic codes and numerical codes as shown in Table 1.

In addition to the logic functions, Table 1 contains certain other code numbers, also referred to as functions, related to the format in which the disease-defining codes are written on the magnetic tape. The first symbol IDS (logic code 01) is placed at the end of a series of symptoms and findings as a spacer. The second symbol MLON (logic code 02) is a way of indicating that the symptom or finding following it may occur at one or more designated locations throughout the body. These locations are coded with the code numbers shown on the anatomic location diagrams, of which that shown in FIG. 5 is typical. The third symbol MLOF (logic code 03) is used to indicate the end of a list of location codes. Likewise, the symbol MLEN (logic code 05) is used to indicate the end of a list of symptoms and findings which might have been present at the previously listed locations.

After all the symptoms and findings defining a disease have been listed, the symbol EOS (logic code 11) is used to separate the listing of symptoms and findings from the listing of treatments. If more than one disease is present treatments for each disease are separated by the symbol ITS, (logic code "blank") and the end of a particular medical disease file is indicated by the symbol EOF (logic code 12). To clarify the use of the logic codes in setting up the medical disease files, and example has been given in FIG. 17.

FIG. 17 shows one page of Medical Disease File worksheets which facilitate coding of the information to be included in the Medical Disease File on the magnetic tape. The name of the disease, pulmonary consolidation, etc., is given on the first line of the page followed by a specific diagnosis number, in this case 000003. Thereafter, a storage location number, indicating the location on the magnetic tape at which the disease is to be stored is given; in this case, 062-0-013. As can be seen in FIG. 17, a logic code such as OR preceeds each of the symptoms defining a disease. After the logic code, the symptom is written and the numerical code numbers corresponding to the symptoms are listed serially. Thus, in the example shown in FIG. 17, some degree of fever and some degree of rapid breathing, and some degree of difficult breathing must be present. In addition, certain breath sounds must be present in at least one location in the thorax. This is indicated by first listing the logic code MLON, then listing the site locations, then the logic code MLOF, next, the logic code OR, and finally the breath sounds. Thereafter, the logic code EOS is used to indicate that there are no further symptoms and findings used in defining the chosen disease. Next, the treatments are listed, including numberical codes. The numerical codes for the treatments are obtained from a standard list (not shown).

After all the treatments have been listed, the code number corresponding to the diagnosis, namely 000003 is given, as shown on FIG. 17. This is followed by the intertreatment separator logic code ITS, which is followed by the interdisease separator IDS.

The medical disease file is written on the magnetic tape prior to the insertion of patient information. According to the present invention, it is contemplated that the magnetic tape containing the medical disease file would be prepared, distributed, and controlled by the health authorities in the country where used. The magnetic tape can be replaced from time to time to keep it current with advances in medical science.

The medical disease file differs from the data files common in the art in that it contains both data and logical operation defining codes.

THE PROGRAM

The complete program for operation of the Medical Diagnostic Computer is shown in Tables 9 through 35, in source language. Each instruction has a mnemonic code of three letters, which may be preceded by a label and which may be followed by an operand and a comment. Only the mnemonic code and the operand are entered into the tape, the label and comment being added merely for explanation and convenience. The label portion, when present, is used to provide a shorthand name by which various sub-routines can be called in the program. The mnemonic codes are entered successively into an assembler which produces there-from a translation of the program into machine language, namely binary words.

From a strictly behavioristic point of view, if the machine language program is placed onto the tape along with the Medical Disease File, as described above, the computer will issue treatment instructions when operated in accordance with the Medical Disease Forms and Diagnosis and Treatment Manual as described above. That is to say, the operation of the system does not require that the user have a knowledge of computer programming or medicine. It has been discovered that if a tape coded with the instructions shown in the program of Tables 9 through 35, is inserted into the computer described above, the user will be able to obtain treatment instructions and a diagnosis by use of the Treatment and Diagnosis manual in accordance with the procedures described above. The complete computer program is presented here to provide a disclosure which is truly enabling.

As can be seen from a brief inspection of Tables 9 through 35, the program consists of a series of sub-routines, each labeled by a label which appears in the leftmost column of the Tables preceding the three-letter mnemonics.

Table 36 is a memory map in which the memory locations of the instructions are identified in octal notation. The leftmost column gives the table number. The next column gives the beginning memory location for that table. The next column gives the concluding memory location. The rightmost column gives the magnetic tape storage block number.

Certain of these sub-routines are not particularly novel in that they are mainly concerned with inputting, outputting and housekeeping operations. On the other hand, certain of the sub-routines are believed to involve patentable innovation. These innovative portions of the program will be described below in greater detail through the aid of the flow charts presented in FIGS. 18 through 28. These flow charts serve to illustrate and explain the program but it is the sequence of instructions that defines the program.

The innovative portions of the programs are called ANAL and SONE, acronyms for analysis and site-on. It is the ANAL and SONE sub-routines which together cause the central processor to compare the observed symptoms stored in the computer random access memory with the disease definitions which have been read into the random access memory from a segment of the magnetic tape.

The information from the magnetic tape contains, as described above, the numerically coded disease definitions and the logical functions denoting the relationship to be tested between the disease definitions and the observed symptoms.

The disease-defining symptom codes from the magnetic tapes are compared sequentially, one at a time, to the numerical codes representing the observed symptoms. If, none of the observed symptoms is the first disease-defining symptom, the conclusion is that the patient does not have the disease in question. On the other hand, if the disease-defining code is found among the observed symptoms, the next disease-defining symptom from the magnetic tape is compared to the observed symptom, and the analysis is repeated. If the END OF SYMPTOMS code is identified at some point in the process, then an entire disease has been determined to be present. The next group of data codes, is sent out to the printer to produce the output tape identifying the disease and its treatment.

Thereafter, another set of numerical codes defining a second disease may be read into the random access memory from the magnetic tape, and the comparison process repeated for the next disease.

The "C" register of the central processing unit contains the memory byte address (memory cell pointer) for the magnetic tape information in RAM 010. It always starts with 0, and the maximum is 256 base 10 or 377 base 8.

During the execution of the above-described algorithm, RAM page 010 is used to store information read-in from the magnetic tape. Information read-in from the keyboard is stored in RAM page 013. The portions of the program comprising the SONE and ANAL routines are stored in RAM pages 011 and 012 respectively.

Table 2 is a schematic diagram showing the arrangement of the data on RAM page 013, which has been entered through the keyboard. The RAM page contains 85 3-byte cells of memory. Each cell is divided into 3 bytes yielding a total of 255 bytes altogether. As shown in Table 2, certain keyboard entries correspond to certain values stored in the memory cells. For example, a keyboard input of 000000 would be represented by the values 000 000 000 in the RAM. Likewise, a keyboard entry of 999999 would be stored in the RAM as 231 231 231.

Logical function codes used in defining diseases and stored on the magnetic tape are inserted into the RAM. The first two bytes each equal to 273. The third byte only is instrumental in identifying which of the function codes is stored, while the 273 entries stored in the first and second bytes serve to identify the item stored as being a logical function. As can be seen, a blank space is indicated by 377 377 377.

During the execution of the program, certain portions of the RAM are reserved and used for the storage of indicators. These indicators each are referred to by a label, and the purpose of each is described after the label used to reference it as follows:

RESUL is used to store the fact that the site operation is on or off during a particular iteration.

SONAD is used to store the address of the first site data to be combined with disease-defining symptom codes from the magnetic tape to provide a two-part disease defining code, one part giving the site in the body and the other part giving the symptom.

RESL is used to store the result of intermediate comparisons between disease-defining items from the magnetic tape and the observed symptoms from the keyboard during multiple site operations.

FUNC is used to store the logical function code from the magnetic tape which governs the type of comparison to be made between the disease-defining codes and the codes defining the observed symptoms.

ORR is used to store the results of comparisons between the disease-defining codes and the observed symptom codes during the logical OR operation.

XRO is used to store the result of comparisons between disease-defining codes from the magnetic tape data and the observed symptoms from the keyboard data during the EXCLUSIVE OR logical operation.

The portions of the program which compare the disease defining codes with the observed symptom codes to determine a diagnosis and treatment instructions will be described in the following paragraphs.

That comparison is contained in portions of the program referred to as the ANAL (analysis) routine and the SONE (site operation on) routine. The ANAL routine is shown in Tables 3, 4, and 5, while the SONE routine is shown in Tables 6, 7, and 8. Flow-charts describing the ANAL routine are shown in FIGS. 18-24 inclusive, while flow-charts describing the SONE routine are shown in FIGS. 25-28 inclusive.

The ANAL and SONE routines are divided into a number of shorter sub-routines, typically consisting of less than a dozen instructions each, and these sub-routines are labeled by groups of letters placed in the leftmost column of the program beside the first instruction in the sub-routine. The same labels have been carried over to the flow-charts so that the correspondence between the program and the flow-chart is facilitated.

Figure 18:
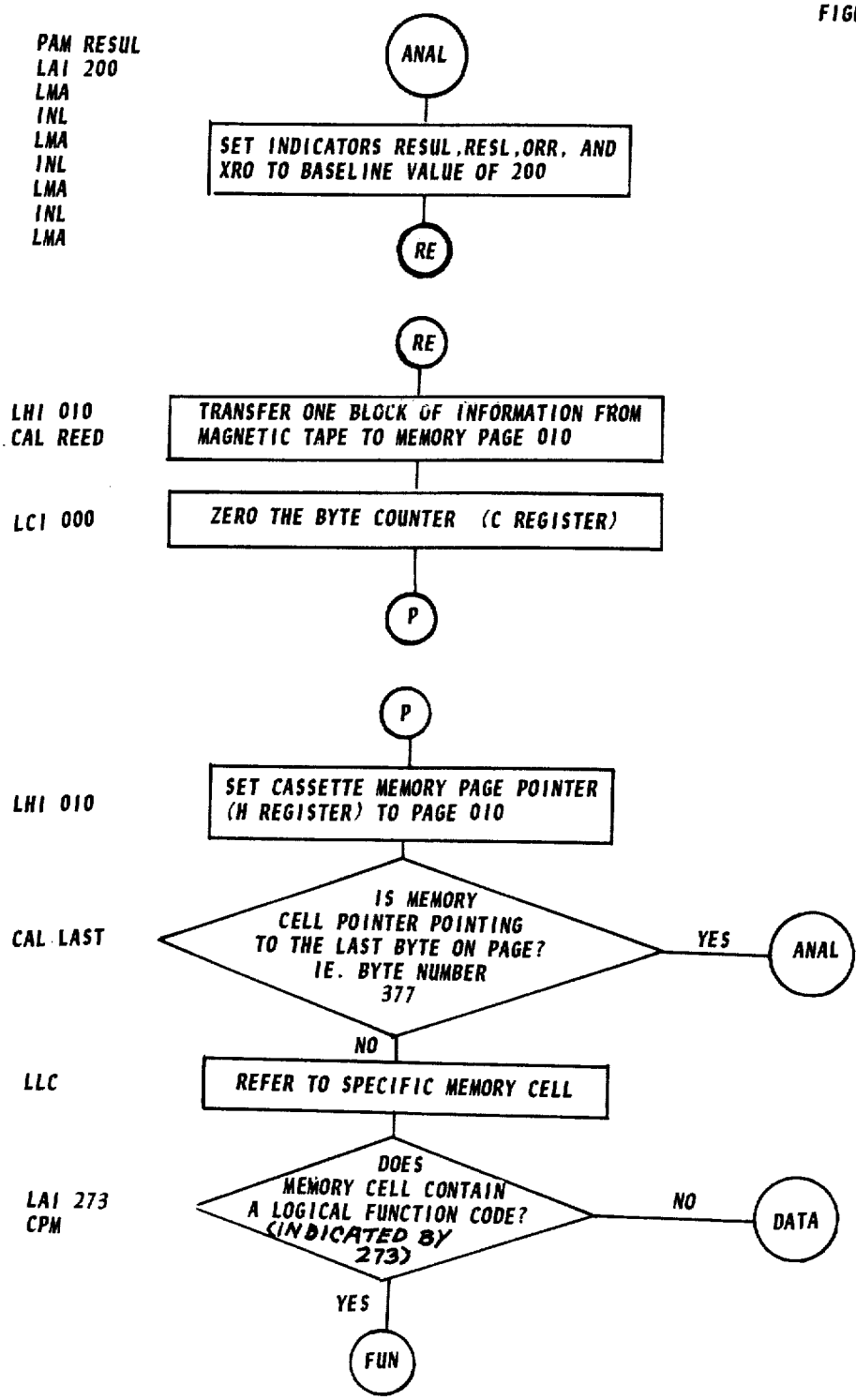
Figure 18:
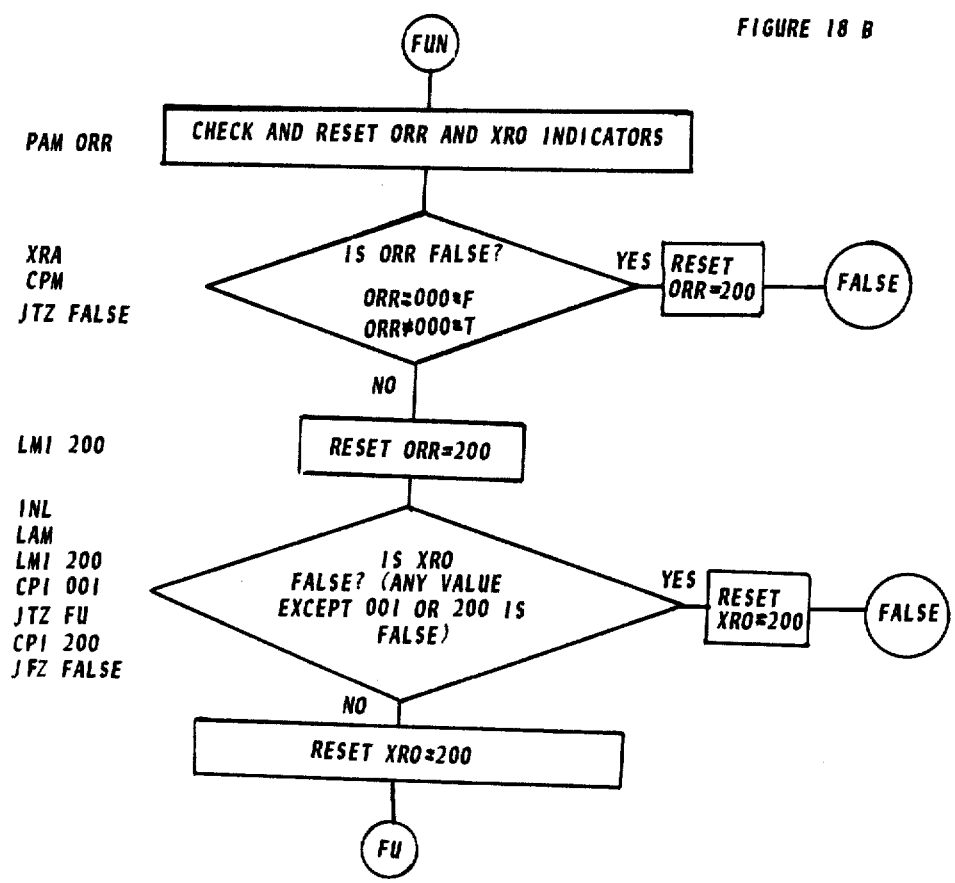

The first sub-routine is labeled ANAL as shown on the program in Table 3 and the flow-chart of FIG. 18.

The first sub-routine, ANAL comprises the first nine instructions which set the RESUL, RESL, ORR, XRO indicators described above to a base line value, namely 200 (Octal). Thereafter, a sub-routine labeled RE is entered which transfers one block of information from the magnetic tape to page 010 of the RAM. Once the block of data has been read-in from the magnetic tape to the RAM, the computer examines the data according to sub-routine P to determine whether the C register=377 ie: there is no more data to be checked in page 010 of RAM by calling the sub-routine LAST. If the C register ≠377 then the piece of information selected from page 010 was not the last byte; it is examined to determine whether it is a logical function code or whether it is a disease-defining code. If it is not a logical function code, the program branches to the sub-routine DATA, which will be described below. If the item being examined is a logical function code, the program continues with the FUN sub-routine.

The FUN sub-routine first points to the ORR indicator and zeros the A register. Thereafter, it compares the memory register with the accumulator, and if it is found that the number in the memory was 0 an indication of FALSE is given and the program jumps to the FALSE sub-routine described below; while if the number in memory is not 0, a TRUE indication is given. In either case the ORR is reset to=200. The program next points to the XRO indicator and performs a test to determine whether the XRO indicator was false. If the XRO indicator is false, the program jumps to the FALSE sub-routine to be described below. If the XRO indicator was not false, the program continues on to the next sub-routine (FU).

The result of these twelve instructions in the FUN subroutine is to determine whether any of the disease-defining codes were previously found among the entered codes corresponding to the observed symptoms. The ORR indicator accumulates the number of successful previous matches between the disease defining codes and the observed symptoms and findings. If no matches are indicated, the ORR indicator is regarded as false and the program branches to the sub-routine FALSE, resetting the ORR indicator in the process.

If it has been determined that the ORR has been satisfied (i.e. one or more of a group of findings has successfully been matched) the program continues to the FU sub-routine, resetting the ORR indicator in the process.

Figure 19:
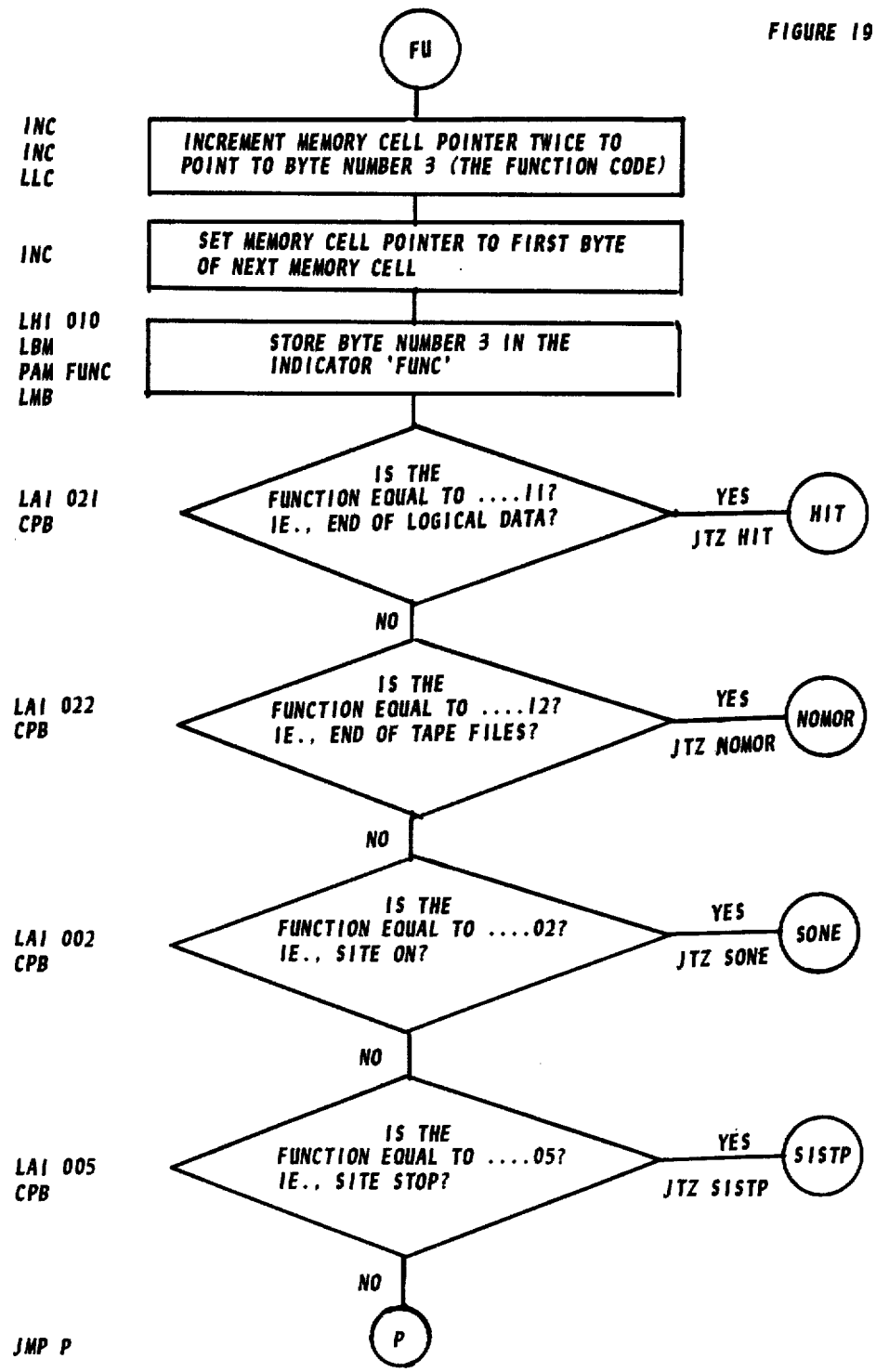

The XRO indicator accumulates the number of successful previous matches between the disease defining codes and the observed symptoms and findings. If more than one match has been indicated, the XRO indicator is regarded as false and the program branches to the sub-routine FALSE, resetting the XRO indicator in the process. If it has been determined that the EXCLUSIVE OR (XRO) test has been satisfied, (i.e. not more than one of a group of findings has successfully been matched) the program continues to the FU sub-routine, resetting the XRO indicator in the process. The program discussed to this point is shown in the flow-chart of FIG. 18. The flow-chart for the sub-routine FU is shown in FIG. 19.

In the sub-routine FU, the memory cell pointer (register C) is incremented twice so that the third byte in the memory cell is referenced. It will be remembered that the third byte is used for storing the logic codes which are also shown in Table 1 above. The third byte is then stored in the indicator FUNC memory space, the memory cell pointer is set to the first byte of the next memory cell, and a series of tests are next performed to determine which of the logic function codes is present. A test is performed to determine if the logic function is number 11, END OF SYMPTOMS AND FINDINGS.

If code 11 is present, the program branches to the HIT sub-routine, indicating that a valid match between a group of disease codes and the entered symptom codes has been found.

If the logic function code was not 11, a test is performed to determine whether it was logic code 12, signifying the END OF MEDICAL DISEASE FILE. The program branches on an affirmative answer to the sub-routine NOMOR which restores the computer to an initial condition, for analyzing the next patient.

If, however, the logic code was not 12, a test is performed to determine whether the logic code was 02, MULTIPLE LOCATION ON. If an affirmative answer is determined, the program branches to sub-routine SONE. If the logic code was not 02, a further test is performed to determine whether the logic code is 05, MULTIPLE LOCATION END OF SYMPTOMS AND FINDINGS. The program branches on an affirmative answer to the sub-routine denoted by the label SISTP. If however, a negative answer is determined, the program jumps to the sub-routine P described above and shown on FIG. 18, this latter jump resulting in an iteration of most of the above instructions using the data or logic function stored in the next memory cell in the RAM where it had been reading from the magnetic tape. This concludes the FU sub-routine shown in FIG. 19 and concludes the list of instructions shown in Table 3.

Figure 20A:
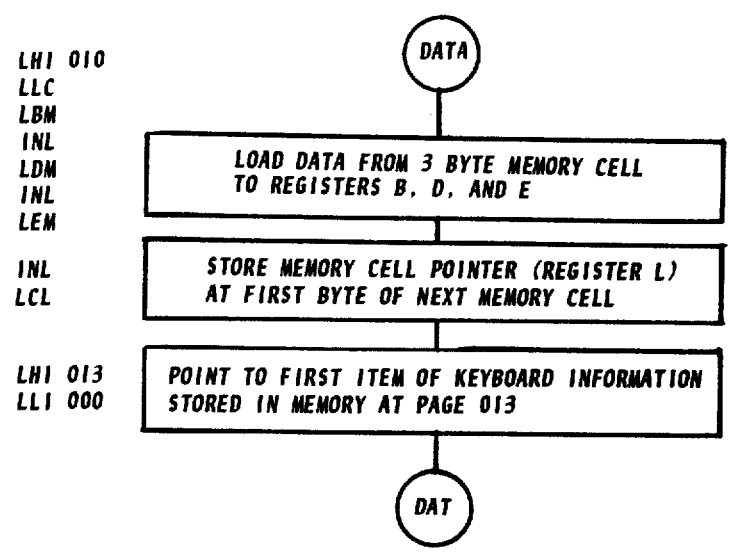
Figure 21:
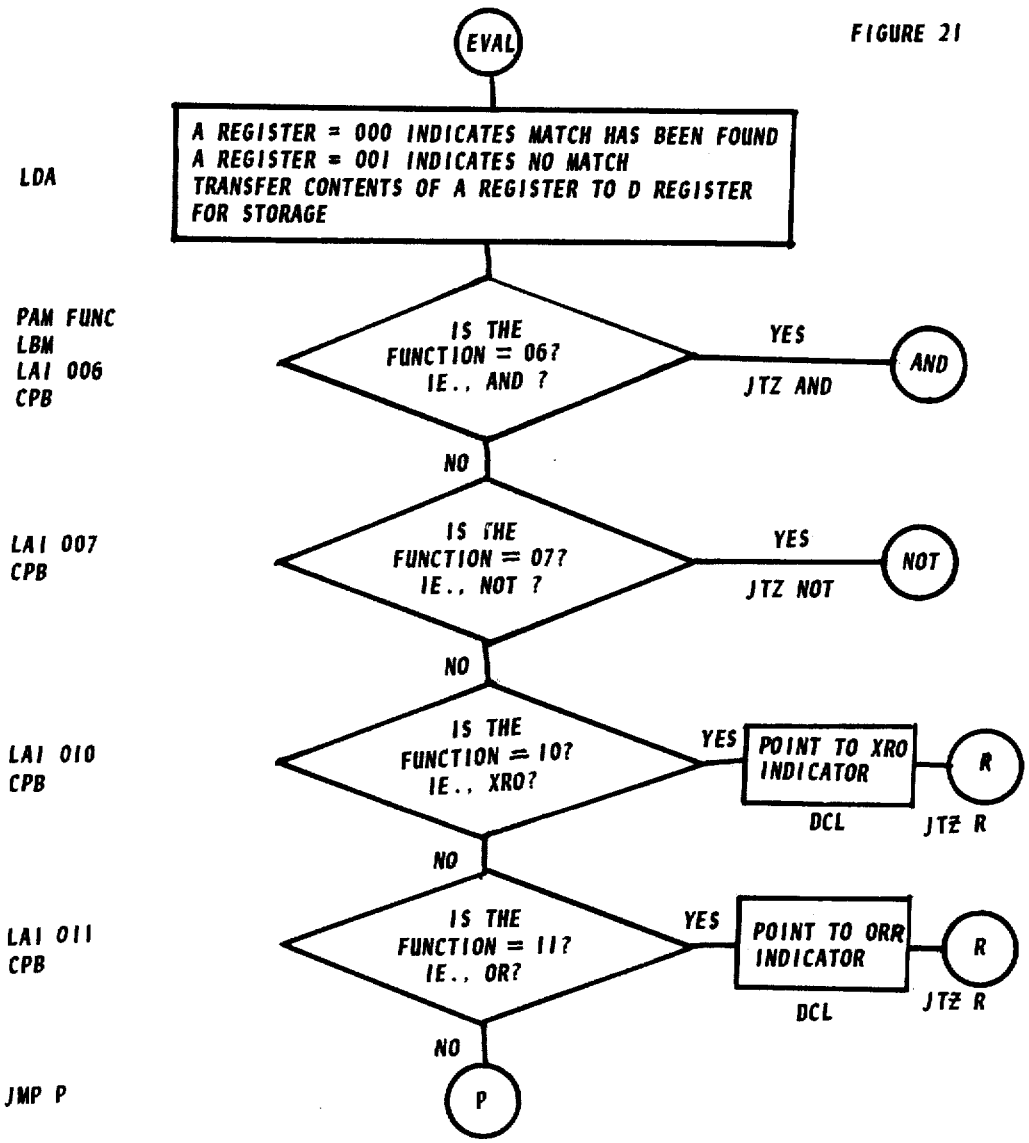

Turning now to the continuation of the program shown in Table 4 with references to the flow-chart of FIG. 20, the DATA sub-routine will now be described. First, three bytes of data stored in the RAM are read into registers B, D and E of the central processor unit, the memory cell pointer, pointing at the first byte of the next memory cell, being reserved. Next, the byte pointer for the keyboard information located in RAM 013 memory is examined. A test is then performed to determine whether the byte address of keyboard information is the last byte of memory page 013. If the byte address is the last one on the page, the A register is set at 001; which indicates that no match had been obtained between the disease-defining codes and the observed symptoms; in this case, the program branches to the sub-routine EVAL, to be described below.

If the byte address is not the last byte on the page of memory, the A register is set at 001 as a baseline, a comparison is made wherein the disease-defining code stored in the B, D, and E registers of the central processor unit is compared to the keyboard item in the memory. If they are the same, the program sets the A register to 000 indicating a match has been found and branches to the sub-routine EVAL. If they are not the same, the next item of keyboard-entered data is taken up and compared with the disease-defining code stored in the central processor unit registers B, D and E. It is seen from the instructions that the comparison is made in three successive tests, one for each of the B, D and E registers in which the disease-defining symptom codes are stored. The instruction JMP DAT reverts the program to the entry point of DAT thereby closing an iterative loop to permit successive items of keyboard information to be compared with a selected disease-defining symptom code.

Exit from the DATA sub-routine is to the EVAL sub-routine, the instruction JMP EVAL being unconditional.

As described above, if a match is found, the A register will read 000 and if no match was found the A register will read 001. The significance of a match is determined by the logic function code from Table 1 above, applicable to the disease-defining symptom being compared. For this reason, it is necessary to know what the logic function code was. This is accomplished by the sub-routine EVAL shown in Table 4, which will now be described with reference to the flow-chart of FIG. 21.

The EVAL sub-routine basically consists of loading the unidentified logic function code into register B and then loading various known logic function codes into the accumulator for comparison with the unidentified code in register B. First, it is determined whether the inidentified logic function code is code 06,AND,of Table 1 above. If it is, the program branches to the sub-routine labeled AND. If not, a test is performed to determine whether the function is 07,NOT. If "yes" the program branches to the sub-routine NOT. If "no", the content of the index register L is decremented to cause the memory cell pointer to point to the XRO indicator. The program then continues with a test for determining whether the unidentified logic code is 010,XRO. If "yes", the program enters the subroutine R.

If it is determined that the unidentified logic code function is not 010, the memory cell pointer is directed to the ORR indicator. A test is performed to determine if it is logic code 11,ORR. If it is, the program continues by entering the sub-routine R. Since these tests exhaust the logic function codes available, a negative answer to the last question leads to the conclusion that the unidentified logic function code was an invalidly code item. In this eventuality, the program unconditionally jumps to the sub-routine P above. That completes the EVAL sub-routine whose instructions are listed serially in Table 19 and described in the flow chart of FIG. 21.

Figure 22:
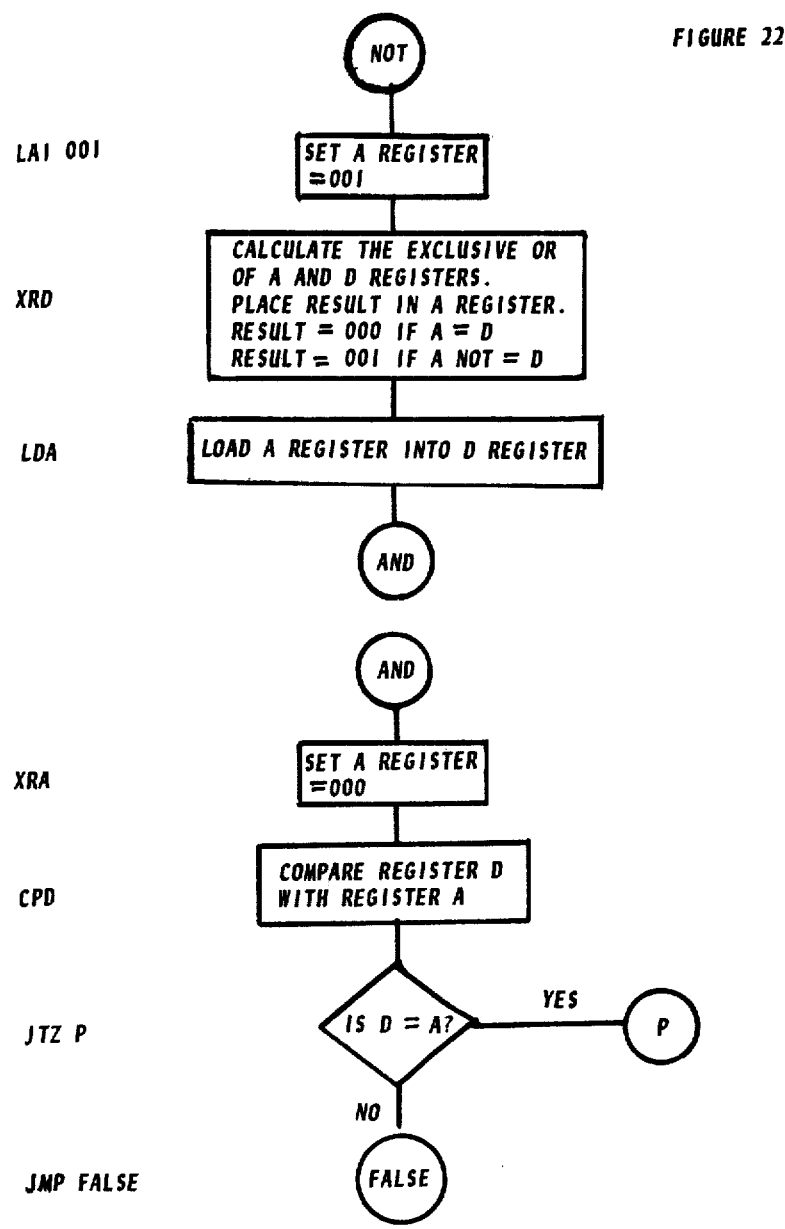

Turning now to Table 5 and FIG. 22, the NOT and the AND sub-routines are shown. The NOT sub-routine is used to implement the possibility that a specific symptom is required to be absent in order for a particular disease to be defined. This is accomplished by loading 001 into the accumulator and then calculating the EXCLUSIVE OR of register D with the accumulator, and storing the result in the accumulator which is thereafter loaded into the D register. Next the accumulator is zeroed by the first instruction XRA of the AND sub-routine and then the D register is compared to the accumulator. Since the accumulator has been zeroed, the comparison will be true if the D register, at the time it is compared, contains 000, in which case the program jumps to sub-routine P shown above, while if register D is not equal to 000, the program jumps unconditionally to the sub-routine labeled FALSE.

As seen above, in the sub-routine labeled EVAL, depending on which logical function code was present, the EVAL sub-routine could jump to either the NOT sub-routine or the AND sub-routine. From the above discussion of the DAT and the EVAL sub-routines, it is clear that the contents of register D would be either 000 if a match between the disease defining codes and the observed symptoms had been found, and the contents of the D register would be 001 if no match had been found, in accordance with the first instruction LDA of sub-routine EVAL. Thus, in the AND sub-routine, when the zeroed accumulator is compared with the D register, the comparison will be true if there was a match (000 condition), and will not be true if a no match (001 condition) had been found.

The purpose of the NOT sub-routine is to reverse the contents of the D register in the event the logic function code was 07, NOT. In such case the D register will, when compared to the zeroed accumulator in the AND sub-routine, contain 001 if there is a match and 000 if there is no match. This reversal is accomplished through the EXCLUSIVE OR instruction in the NOT sub-routine. The result of the EXCLUSIVE OR instruction is a 000 if the D register is the same as the accumulator, namely 001, indicating no match. The result of the EXCLUSIVE OR instruction is a 001 if the content of the D register is different from the content of the accumulator, indicating a match. The result of the EXCLUSIVE OR instruction is immediately placed into the accumulator and then loaded into the D register by the third instruction in the NOT sub-routine, prior to use in the AND sub-routine.

Figure 23:
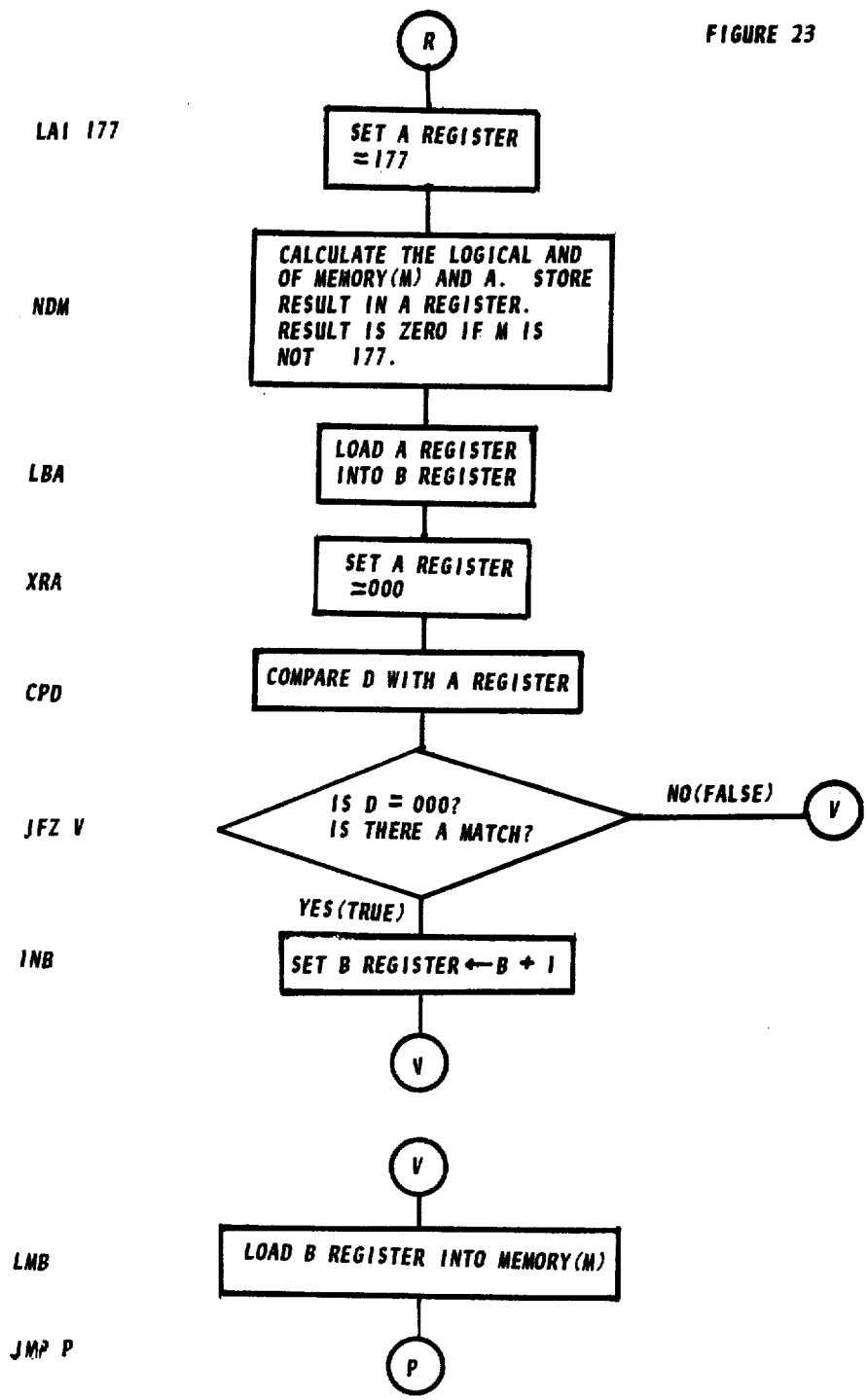

The R sub-routine follows the AND sub-routine, and is shown in the flow-chart of FIG. 23. The first two instructions in sub-routine R mask out the seventh bit in either the ORR or the XRO indicators which sets the indicators to the "on" position. The B register is incremented each time a match is found and the new contents of the B register are stored in memory at a location previously defined depending on whether the logic function was ORR or XRO. After the ORR and XRO indicators have been updated, if required, the program jumps to sub-routine P above to pickup the next disease defining code to continue the analysis.

Figure 24:
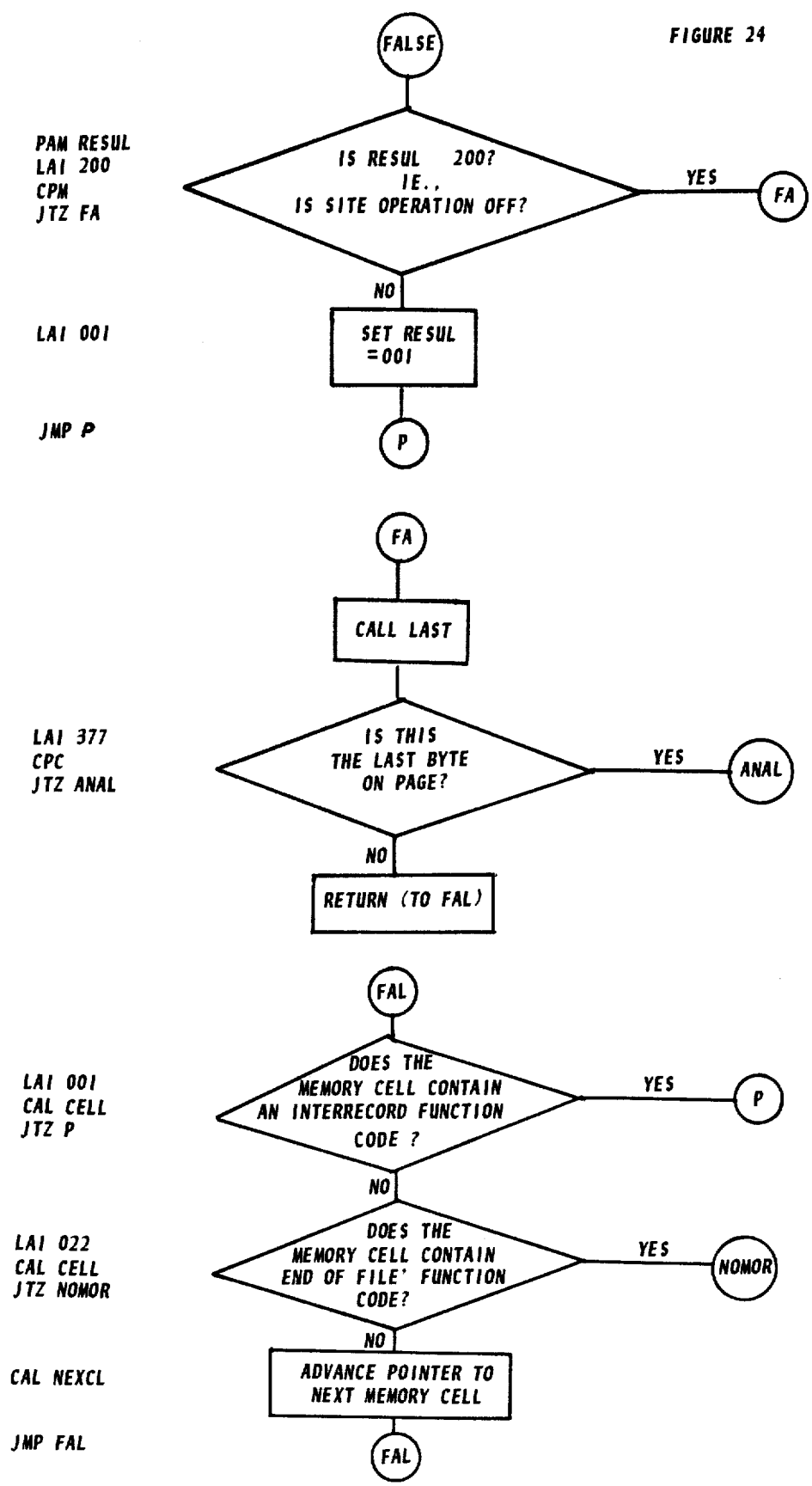

The final sub-routine in the ANAL portion of the program is the FALSE sub-routine, shown in FIG. 24. This sub-routine, which was seen above, was entered from the FUN and the AND sub-routine is merely a short routine used to check whether the site operation indicator is off. If site operation is "off" the computer is instructed to look for the inter-record function, while if the site operation is "on", the computer is instructed to attempt more permutations of sites with disease-defining symptoms. The remaining instructions shown in Table 5 are of two types: The ADR and the LOC instructions. These are special assembler instructions which are not executed by the microcomputer. The ADR instructions assigns memory addresses to the sub-routine named in the label, while the LOC instructions reserve one memory location directly after the entire sub-routine named FALSE.

FIG. 24 shows the FALSE sub-routine as well as the FA and the FAL sub-routines which follow the SONE portion of the program and which are shown in Table 8 in the form of instructions. These are all utility sub-routines which instruct the computer to (1) repeat the analysis with a new block of data from tape if memory cell pointer is at the last byte on the page; (2) or analyze the next disease code if the current memory cell is an inter-record function code; (3) or reset the entire system for the next entire run if the current memory cell is the end of the file function code.

Turning now to Table 6, the first five sub-routines shown there, preceding SONE sub-routine, are utility sub-routines used to instruct the computer what to do under special circumstances.

For example, the LAST? sub-routine simply checks to determine whether a particular byte is the last one on a page of memory. On each page of memory there are 256 bytes of memory numbered from 0 through 255. In octal notation, the decimal 255 equals 377.

The LAST? sub-routine is used in the following NEXCL sub-routine. The NEXCL sub-routine advances the memory pointer by three. The LAST? sub-routine is used to preclude advancing the memory cell pointer beyond the limit of the last byte on the page.

The sub-routine CELL? is used to determine whether a particular memory cell contains a function or data. Starting with memory cell byte 1, the computer increments to point to the third byte and then compares it with the function in question, whose reference numerical code is stored in the accumulator. The sub-routine returns immediately if the function is not found, but if it is found, the further question of whether the memory cell byte 1 contains the numerals 273 (in octal) is asked. The octal number 273 is used to indicate certain formatting codes. The use of this sub-routine in connection with FAL sub-routine above has already been described.

The SOF? and SOFF sub-routines instruct the computer to find a particular memory cell containing logic code 03, which from Table 1 above indicates that the site operation is off (not being used). The SOF? and SOFF sub-routines are simply used to determine which memory cell contains the logic code for indicating the end of the list of sites.

Figure 25:
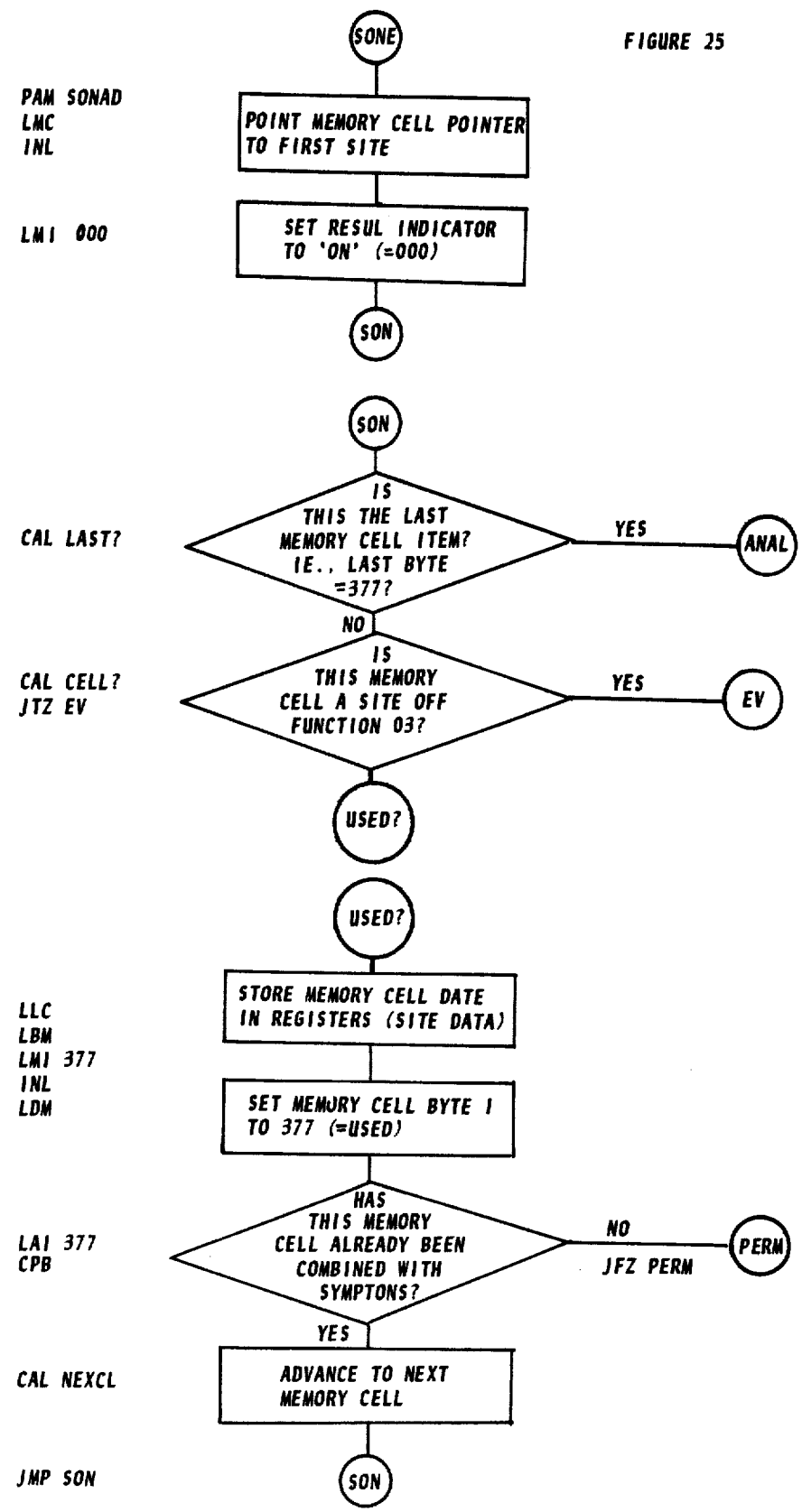

The SONE, SON and USED? sub-routines will be discussed in connection with the flow-chart of FIG. 25.

The SONE sub-routine sets the memory cell pointer to the first site and then sets the RESUL indicator to 000, which indicates that the computer is to operate in the site-on mode. In that mode, the disease-defining symptoms are combined with the various locations in which they occur to produce all possible combinations of symptoms and their locations. These combinations are then compared with the observed combinations to determine whether a match is present.

The analysis continues with the SON sub-routine which first determines whether the item in the memory cell was the last byte on the page. If it was, the program jumps to the sub-routine ANAL. If not, a determination is made whether the memory cell contains a site-off function, denoted by the logic code 03. If a site-off function is present, the program branches to the sub-routine EV. If a site-off function is not present, the routine continues by determining whether this particularly memory cell has already been combined with the symptoms. If not, the memory cell data is stored in registers and a notation is made in the memory cell to the effect that its data has been used. Thereafter, the computer advances through the PERM sub-routine. In the event the memory cell has already been used, the computer is instructed to advance to the next memory cell and then to repeat the above questions by entering the SON sub-routine.

Figure 26:
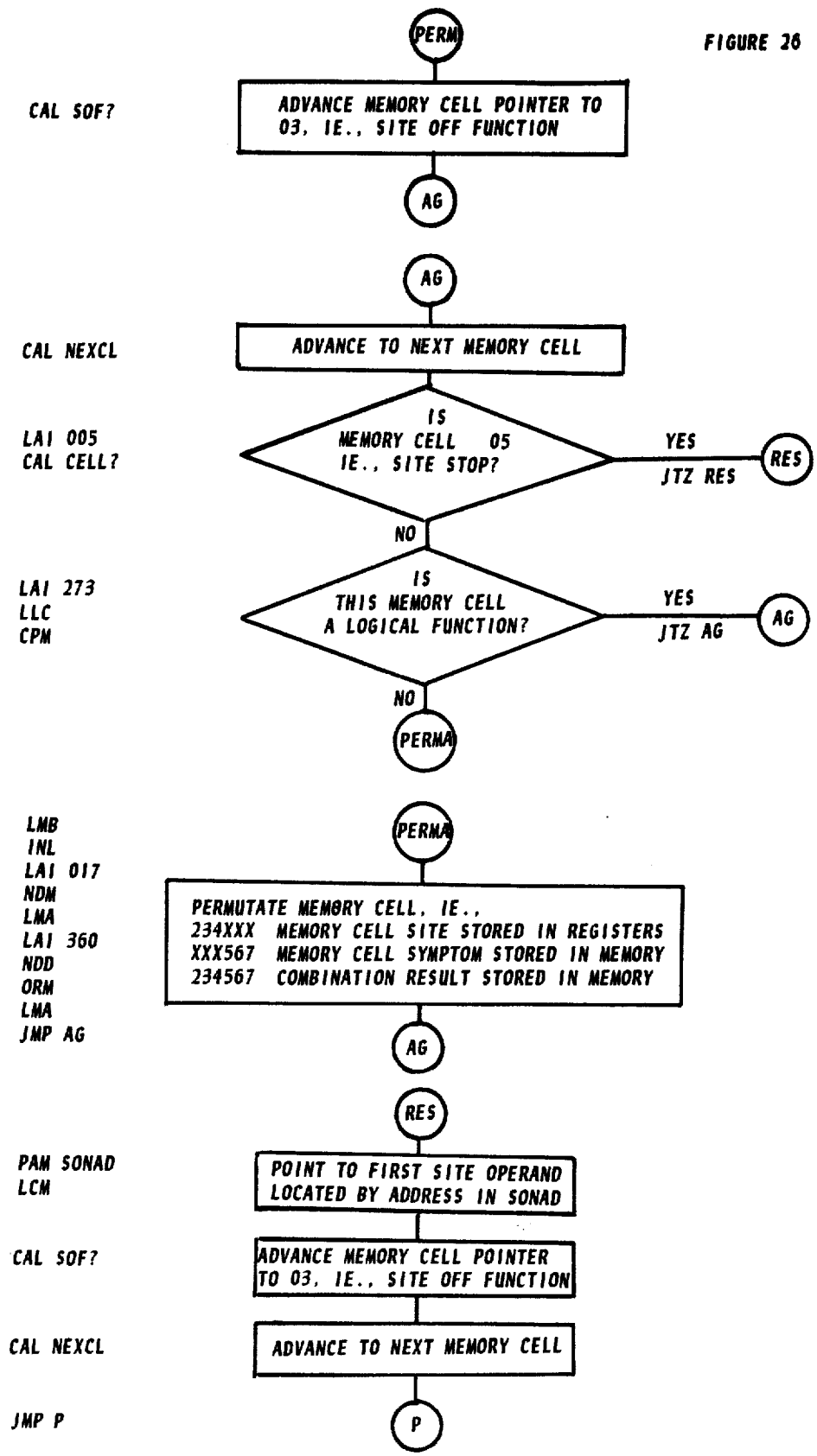

In the flow-chart of FIG. 26 the sub-routines PERM, AG, PERMA, and RES are shown. The instructions for these sub-routines are listed in Table 7. The PERM sub-routine merely advances the memory cell pointer to 03, the site-off function. In the AG sub-routine the contents of the next memory cells are examined and a test is made to determine whether the next memory cell contains a 05, ie., a site-stop function. If it does, the program branches to RES sub-routine. If not, another test is made to determine whether the memory cell contains a logical function. Logical functions contain the octal numerals 273 in the first byte. If the memory cell is a logical function the program loops back to the input of the AG sub-routine and another memory cell is selected. If not, the program advances to the PERMA sub-routine.

The PERMA sub-routine is the one which combines the sites with the symptoms.

The PERMA sub-routine forms a composite number whose first three left-most decimal digits represent the site while the right-most three decimal digits represent the symptom. This is accomplished as follows. Byte 1 of the site memory cell replaces and is stored in byte 1 of the symptom memory cell. The upper four bits of byte 2 of the symptom memory is masked out. The lower four bits of byte 2 of the site memory cell are masked out. Byte 2 of the site memory cell and byte 2 of the symptom memory cell are combined and this new byte is stored in byte 2 of the symptom memory cell. Byte 3 of the symptom memory cell is not changed. After the 3 byte combination memory cell data has been formed, the program jumps unconditionally to the AG sub-routine.

The RES sub-routine is a housekeeping routine which advances the memory cell pointer prior to the analysis carried out in the P sub-routine.

Figure 27:
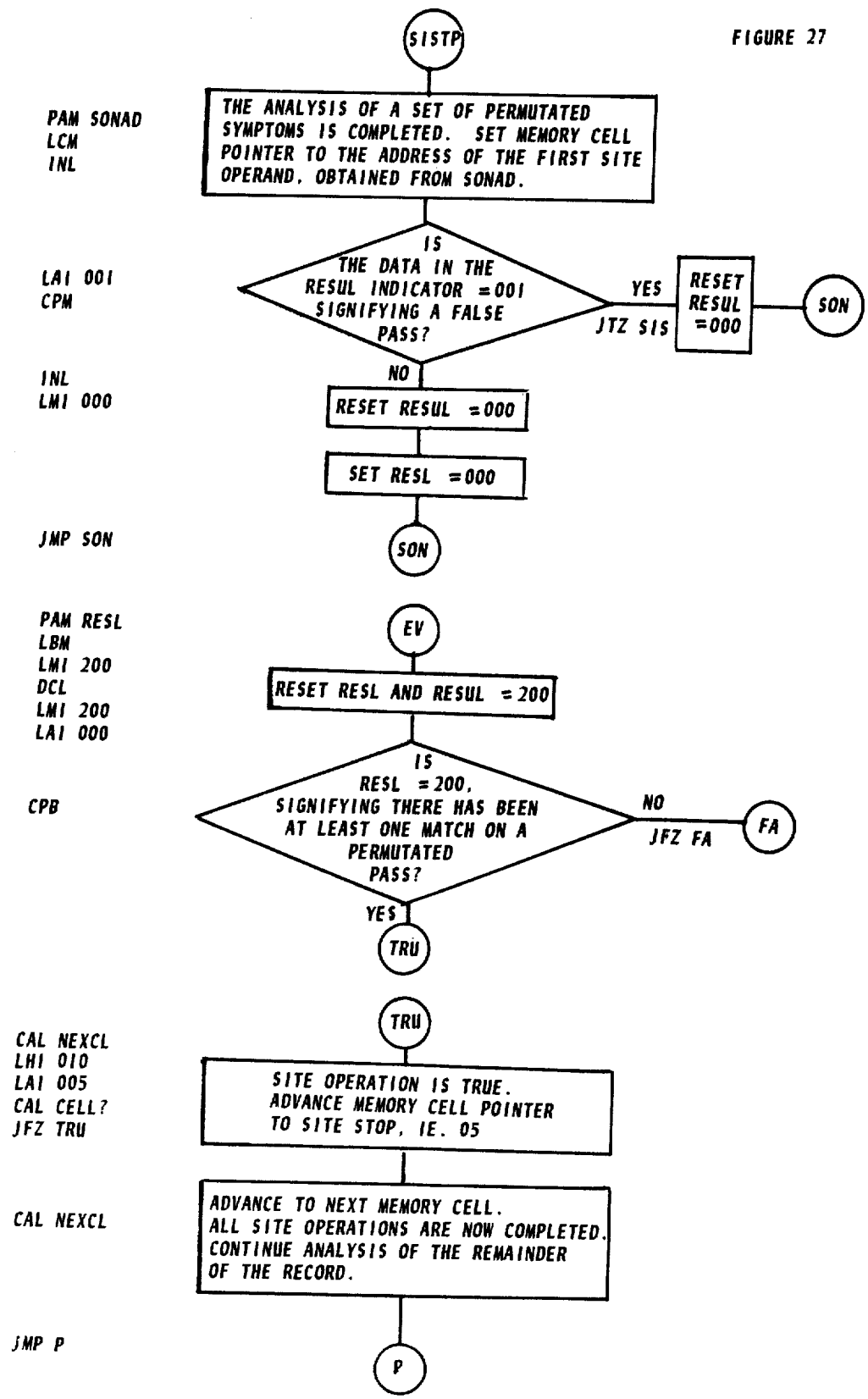

A flow-chart showing the SISTP, SIS, EV and TRU sub-routines is shown in FIG. 27. The SISTP sub-routine is entered after the analysis of a permutated set of symptoms has been completed. A test is then made to determine whether there has been a false pass, meaning that no match was found, and after the test the RESUL indicator is set to 0, and the RESL indicator is also set to 0 in case there had been a match.

The EV sub-routine also is quite simple, resetting the RESL and RESUL indicators both to 200. Thereafter, a test is made to determine whether at least one match has been found on a site-symptom pass. If not, the program branches to the sub-routine FA while if a match was obtained, the program continues with the TRU sub-routine. In that sub-routine, the memory cell pointer is advanced to site-stop, i.e., 05.

The remaining instructions are shown in Table 8, and they deal with storing and printing the result of the analysis. A flow-chart illustrating these instructions is shown in FIG. 28. When it has been determined that a valid match has been found, the HIT sub-routine is entered. This routine saves the value of the memory cell pointer and tests to determine whether the contents of the memory cell includes 001, the logic code inter-disease separator. If the inter-disease separator is present, it means that at least one additional set of disease-defining symptoms must be tested, in which case the program branches to the sub-routine P for further analysis.

If the inter-disease separator code is not present, the program continues by preparing to print the results. First, the input/output printer buffer is cleared and then the memory cell on page 010 of the RAM is transferred to I/O buffer at page 012. Next, the print routine is called from its storage place in ROM 001. After the printout, the memory cell pointer is restored and advanced to the next memory cell. This latter operation is performed through the sub-routine NEXCL. The routine jumps back to HIT.

Thus, all of the sub-routines making up the ANAL and SONE portions of the program of the Medical Diagnosis Computer have been described both in terms of the instructions comprising the sub-routine and in terms of flow-charts showing the successive steps in the computation.

TABLE 1

LOGIC CODE TABLE

| LOGIC CODE | SYMBOL | DESCRIPTION |
|---|---|---|
| 01 | IDS | INTER DISEASE SEPARATOR |
| 02 | MLON | MULTIPLE LOCATION ON |
| 03 | MLOF | MULTIPLE LOCATION OFF |
| 05 | MLEN | MULTIPLE LOCATION END OF SYMPTOMS AND FINDINGS |
| 06 | AND | THE FOLLOWING DISEASE CODES MUST BE PRESENT |
| 07 | NOT | THE FOLLOWING DISEASE CODES MUST BE ABSENT |
| 08 | XOR | ONLY ONE OF THE FOLLOWING DISEASE CODES MUST BE PRESENT |
| 09 | ORR | ONE OR MORE OF THE FOLLOWING DISEASE CODES MAY BE PRESENT |
| 11 | EOS | END OF SYMPTOMS AND FINDINGS |
| 12 | EOF | END OF MEDICAL DISEASE FILE |
| blank blank (BL) | ITS | INTER TREATMENT SEPARATOR |

TABLE 2

ARRANGEMENT OF DATA ON RAM PAGE 013 EXEMPLIFYING KEYBOARD INPUT AND MEMORY CODING

| KEYBOARD INPUT - DECIMAL | RAM PAGE 013 MEMORY CELLS - OCTAL | | | FIRST BYTE OF EACH MEMORY CELL - OCTAL ADDRESS |
|---|---|---|---|---|
| | BYTE 1 | BYTE 2 | BYTE 3 | |
| 000000 | 000 | 000 | 000 | 000 |
| 999999 | 231 | 231 | 231 | |
| DEPRESS FUNCTION KEY + 00 | 273 | 273 | 000 | |
| DEPRESS FUNCTION KEY + 99 | 273 | 273 | 231 | |
| DEPRESS FUNCTION KEY + NO DIGITS | 273 | 273 | 377 | |
| NO ENTRY | 377 | 377 | 377 | nnn 374 (LAST CELL) |

```
ANAL   PAM RESUL           SET INDICATORS TO 200
       LAI 200
       LIA
       INL       RESL
       LIA
       INL       ORR
       LIA
       INL       XRO
       LIA
PE     LHI 010             ADVANCE TAPE 1 BLOCK
       CAL FEED            HLT IF READ ERROR. PRINT 0
       LCI 000             MEM CELL POINTER FOR P 010, CASET
P      LHI 010             CASET MEM CEL POINTER, P010
       CAL LAST?
       LLC
       LAI 273             IS MEM CELL   DATA OR FUNCTION?
       CPI
       JFZ DATA
                              ORR    XRO
  e                     000    F      F
  e                     001    T      T
  e                     002    T      F
  e                     INO    T      F
  e                     200    T      T
  e
FUN    PAM ORR             CHECK &RESET ORR&XRO FUNCTIONS
       XRA
       CPI                 000=FALSE      >0=TRUE
       LAI 200               RESET ORR MEM
       JTZ FALSE             IF A=R, JMP TO FALSE
       INL                 POINT TO XRO
       LAM
       LAI 200             RESET XRO MEM
       CPI 001               001 IS VALID
       JTZ FU
       CPI 200             200 = NON OPERATIVE FUNCTION
       JFZ FALSE           ANY VALUE EXCEPT 001 &200 ARE FALSE
FU     INC
       INC                 SET C TO BYTE 3
       LLC                 POINT TO BYTE 3 M
       INC                 SET C TO NEXT MEM CELL
       LHI 010
       LBM                 LOAD MEM BYTE 3(FUNC) TO B
       PAM FUNC
       LMB                 STORE MEM BYTE 3 IN FUNC
       LAI 021             END OF LOGICAL DATA FUNCTION,....11
       CPB
       JTZ HIT             SUCESS!
       LAI 022             END OF FILES FUNCTION?  ....12
       CPB
       JTZ NOMOR           GO TO END OF FILE ROUTINE
       LAI 002             SON, SITE ON, FUNCTION? ....02
       CPB
       JTZ SONE
       LAI 005             SISTP, SITE STOP, FUNCTION? ....05
       CPB
       JTZ SISTP
       JMP P               LOOK AT NEXT MEM CELL FOR DATA
                           OR ANOTHER SUBSEQUENT FUNCTION
  e
```

```
DATA    LHI 010         P 010 MEM CELL TO REG B, D, E
        LLC
        LBM
        INL
        LDM
        INL
        LEM
        INL
        LCL             SAVE P 010 NEXT MEM CELL POINTER
        LHI 013
        LLI 000         KEYBOARD INPUT DATA PAGE 013
DAT     LAI 377         ARE WE AT THE LAST BYTE YET?
        CPL
        LAI 001         SET UP NO MATCH VALUE JUST IN CASE.
        JTZ EVAL        IF AT LAST BYTE, THEN NO MATCH
        LAB             IS THE MEM CELL CASET IN MEM CELL KETBRD?
        CPM
        JFZ FAIL1
        INL
        LAD
        CPM
        JFZ FAIL2
        INL
        LAE
        CPM
        JFZ FAIL3
        XRA             A=000       THIS IS A MATCH
        JMP EVAL
FAIL1   INL
FAIL2   INL
FAIL3   INL             POINT TO NEXT MEM CELL
        JMP DAT         KEEP CHECKING KEYBRD INPUT FOR MATCH
•
•
EVAL    LDA             A=000 FOR MATCH    =001 FOR NO MATCH
        PAM FUNC        WHAT IS THE OPERAND
        LBM
        LAI 006         AND?
        CPB
        JTZ AND
        LAI 007         NOT?
        CPB
        JTZ NOT
        LAI 010         XROR?
        DCL             POINT TO XRO
        CPB
        JTZ R
        LAI 011         OR?
        DCL             POINT TO ORR
        CPB
        JTZ R
        JMP P           INVALID FUNCTION. IGNORE DATA.
•                       GO LOOK AT NEXT CASET MEM CELL•
NOT     LAI 001         COMPLIMENT BIT 0 OF REG D
        XRD
        LDA             NOW TREAT NOT FUNCTION AS AN AND FUNCTION
AND     XRA
        CPD
        JTZ P           AND: MATCH FOUND-RECORD VALIDATED
•                       NOT: NO MATCH FOUND-RECORD VALIDATED•
        JMP FALSE       AND: NO MATCH FOUND-RECORD INVALIDATED
•                       NOT: MATCH FOUND-RECORD INVALIDATED•
```

```
R       LAI  177
        NDM            MASK OUT BIT 7
        LBA
        XPA
        CPD
        JFZ  V         IF A=000=A MATCH, FALL THRU TO NEXT INST
        INB
V       LMB            STORE FUNCTION RESULT FOR LATER REVIEW
        JMP  P         JMP TO P. CHECK NEXT CASET MEM CEL

FALSE   PAM  RESUL     IS SITE OPERATION ON?
        LAI  200
        CPM
        JTZ  FA        IF SITE OP OFF, LOOK FOR INTERREC. FUNC.
        LMI  001       SET RESUL=001=FALSE PERMUTATION
        JMP  P         ATTEMPT MORE PERMUTATIONS

FA      ADR  011342
SONE    ADR  011047
SISTP   ADR  011177
HIT     ADR  011266
NOMOR   ADR  000000    SAME AS BEGIN
REED    ADR  000016
LAST?   ADR  011000
NEXCL   ADR  011007
CELL?   ADR  011016

SONAD   LOC  000001
RESUL   LOC  000001
RESL    LOC  000001
ORR     LOC  000001
XRO     LOC  000001
FINC    LOC  000001

END
LAST?   LAI  377       IS THIS LAST BYTE 377, ON PAGE?
        CPC
        JTZ  ANAL
        RET

NEXCL   INC            ADVANCE ADRES POINTER 3 BYTES
        INC
        INC
        CAL  LAST?
        RET

CELL?   LHI  010
        LLC            FIND A SPECIFIC CELL FUNCTION
        INL            REG A =....FUNCTION; C=MEM CEL BYT 1;
        INL            REG H= 010. CAL ROUTINE PROVIDES A,C,H
        CPM            IS MEMCELL BYTE 3= ....FUNCTION?
        RFZ
        DCL
        DCL
        LAI  273
        CPM            IS MEMCEL BYTE 1=273
        RET            FUNCT CELL FOUND-=TZ. NOT FOUND=FZ

SOF?    LAI  003       ....SOF=....03=003; FIND SOF.
```

```
SOFF    CAL CELL?       ADVANCE TO SOF CELL
        RTZ
        CAL NEXCL
        JMP SOF?

SONE    PAM SONAD
        LMC             STORE SON+1 MEM CEL IN SONAD
        INL              POINT TO RESUL
        LMI 000         000=SITE SYSTEM IS NOW OPERATING
SON     LHI 010
        CAL LAST?
        LAI 003         ....SOF=....03=003
        CAL CELL?        IS CELL FUNC=SOF?
        JTZ EV          ALL PERMUTATIONS &COMPARES COMPLETED
USED?   LLC              MEM CELL IS AN OPERATOR
        LBM              STORE OPERATOR BYTE 1 IN B
        LMI 377         SET MEM BYTE 1 TO 377=USED
        INL
        LDM              STORE OPERATOR BYTE 2 IN D
        LAI 377
        CPB             IS THIS OPERATOR CELL ALREADY USED?
        JFZ PERM
        CAL NEXCL
        JMP SON
PERM    CAL SOF?         ADVANCE TO SOF MEM CEL
AG      CAL NEXCL        ADVANCE TO NEXT MEM CELL
        LAI 005          ....SITE STOP=....05=005
        CAL CELL?        IS THIS MEM CELL=SITESTOP FUNCTION?
        JTZ RES          IF YES, PERMUTATION PASS COMPLETED
        LAI 273          IS THIS MEM CELL A FUNCTION?
        LLC              EXAMINE MEM CEL BYTE 1
        CPM
        JTZ AG          IF MEM CEL IS A FUNCTION,LOOK AT NEXT CELL
PERMA   LMB             THIS MEM CELL NEEDS PERMUTATION
        INL             B &  D REG REMAIN CONSTANT
        LAI 017           00001111
        NDM             MASK OUT UPPER 4 BITS OF BYTE 2
        LMA               0000XXXX
        LAI 360           11110000
        NDD             MASK OUT LOW 4 BITS OF D. RESULT TO A
        ORM             ZZZZXXXX
        LMA             ZZZZXXXX   1/2 D + 1/2 M
        JMP AG
RES     PAM SONAD       RETRIEVE ADRES SON+1 MEM CELL
        LCM
        CAL SOF?         ADVANVE TO SOF CELL
        CAL NEXCL        POINT TO 1ST MEM CELL AFTER SOF
        JMP P
SISTP   PAM SONAD
        LCM              C=SON+1 MEM CELL
        INL              POINT TO RESUL
        LAI 001          IS RESUL=001=A FALSE PASS?
        CPM
        LMI 000         RESET RESUL TO 000
        JTZ SIS
        INL              POINT TO RESL
        LMI 000         SET RESL=000=TRUE, IF RESUL=000=TRUE
SIS     JMP SON
EV      PAM RESL        CHECK&RESET RESUL&RESL
        LEM
        LMI 200          RESET RESL=200
        DCL             POINT TO RESUL
        LMI 200          RESET RESUL=200
```

```
        LAI 000
        CPB
        JFZ FA          IF RESL=B=000, SITE OPERATION TRUE
TRU     CAL NEXCL       ADVANCE TO SITE STOP
        LHI 010
        LAI 005
        CAL CELL?
        JFZ TRU
        CAL NEXCL       ADVANCE TO 1 PAST SITE STOP
        JMP P           ALL SITE OPERATIONS ARE COMPLETED!!
HIT     PAM CEE         SAVE C REG
        LMC             STORE MEM CEL ADRES TO BE EXAMINED
        LAI 001         ....01=INTERREC FUNCTION
        CAL CELL?
        JTZ P           GO TO P IF INTERREC FUNCT.
CLRIO   PAM IO12        POINT TO IO 12
●
SONAD   ADR 012335
RESUL   ADR 012336
RESL    ADR 012337
P       ADR 012024
ANAL    ADR 012000
SINS    ADR 001235
●
        LBI 014         CLEAR IOBUF
ZE      LMI 017
        INL
        DCB
        JFZ ZE
        LEC
        CAL UNST        MEM CELL P10 TO IOBUF P 12
        CAL PRINT
        PAM CEE
        LCM             RESET C REG
        CAL NEXCL       ADVANCE TO NEXT MEM CELL
        JMP HIT
●
FA      CAL LAST?
        LHI 010
FAL     LAI 001
        CAL CELL?
        JTZ P
        LAI 022         ....12  END OF FILE
        CAL CELL?
        JTZ NOMOR
        CAL NEXCL
        JMP FAL
●
UNST    ADR 002324
PRINT   ADR 001210
NOMOR   ADR 000000
CEE     ADR 011375
IO12    ADR 012343
●
        END
BEGIN   LAI 377
        OUT 017         PRINTER DISABLED
        CAL INIT        INITIALIZE CASET
        LHI 010
        CAL REED        SYTSM PREP PROG. TO RAM 10, TAPE 000 000
        JMP PREP
REED    CAL READ        READ TAPE BLOCK. HLT IF ERROR
```

```
RERR? LAI 000         DIGIT IS 0
ER?   LBI 001         COL IS 1
ERR?  DCC                DECREMENT ERROR REGISTER
      RFS                RETURN IF NOT NEGATIVE
PROUT CAL SINGL        PRINT REG A NUM & REG B COL
      HLT              CRITICAL SYSTEM ERROR
@
INIT  LAI 001         CLEAR CASET CNTRLER, AC MOTOR ON, +5V OUT
      OUT 016
      XRA             REMOVE CLEAR, KEEP MOTOR ON
      OUT 016
DELAY LBA             20US×256=5000US  5000×256=1280000US
      LCI 177         000 ABOUT 6 SEC. 177 ABOUT 3 SEC
X     INB
      JFZ X
      INC
      JFZ X
      CAL ABORT       ABORT IS INTERNALLY SAFE WITH WAITD
      RET
@
CASOF LAI 010         SOFTWARE 1=0V AT OUTPUT LATCH
      OUT 016
      RET
@
PREP  ADR 010000
SINGL ADR 001363
@
READ  LCI 005
READB CAL WAITD
AD    LEI 140
      LAI 300
      OUT 016
      LAI 246
      OUT 015
      XPA
      OUT 015
READS INP 004
      NDI 040
      JFZ ABORT
      INP 003
      RLC
      JTC READS
READA XPA
      OUT 015
READP INP 003
      NDE
      LEA
READW INP 004
      NDI 040
      JFZ ABORT
      INP 004
      NDI 100
      JTZ READD
      INP 003
      RLC
      JTC READW
      INP 002
      LMA
      INL
      JMP READA
READD XRA
      OUT 016
      LAI 140
```

```
            CPE
            PTZ
            DCC
            JTZ  ABORT
            CAL  WAITD
            CAL  BAKUP
            JMP  READB
WAITD  INP  004
            RLC
            JTC  WAITD
            LLI  000
            RET
BAKUP  LAI  100
            OUT  016
B1       INP  004
            NDI  100
            JTZ  B1
B2       INP  004
            NDI  100
            JFZ  B2
            XRA
            OUT  016
            RET
ABORT  XRA
            LCA
            OUT  016
            CAL  WAITD
            LAI  002
            OUT  016
ABORW  INP  004
            RLC
            JFC  ABORW
            XRA
            OUT  016
            CAL  WAITD
            RET
WRITE  LCI  005
WRITB  CAL  WAITD
            LFI  040
            LAI  200
            OUT  016
            XRA
            OUT  015
            LAI  246
            OUT  015
            OUT  014
WRITW  INP  004
            RRC
            JFC  WRITW
            LAI  240
            OUT  016
WRITL  INP  003
            NDE
            LEA
            INP  003
            RRC
            JTC  WRITL
            LAM
            OUT  014
            INL
            JFZ  WRITL
```

```
WRITD   INP  003
        NDE
        LEA
        INP  003
        NDI  002
        JFZ  WRITD
        LAI  200
        OUT  016
WRITF   INP  003
        NDE
        LEA
        INP  004
        NDI  100
        JFZ  WRITF
        INP  004
        NDI  040
        JFZ  ABORT
        XRA
        OUT  016
        LAI  040
        CPE
        RTZ
        DCC
        JTZ  ABORT
        CAL  WAITD
        CAL  BAKUP
        JMP  WRITB
        END
DRIVE   LAI  377       ALL OUTPUTS LOW=OFF=LOGICAL ONES
        OUT  017       H&L FROM CALL ROUTINE.LOW ORDER MATRX BYTE
        LAI  343       MOTOR RUN & FF CLEAR=HIGH=ONES=ON
        OUT  017
        LDA            STATUS WORD, REG D. BIT#4=SYNC STATUS
        LBI  100       TIMING COUNTER, INITIALLY TOO BIG
        LCI  204       COLUMN PULSE COUNTER.204(8)=132(10)
        LEI  004       MEMORY SHIFT COUNTER
        JMP  DATA      SET DATA UP FOR FIRST TIME THRU
RUN     LAI  020
        NDD            MASK OUT ALL BUT BIT #4
        JTZ  DEL1      IF BIT 4=0, REG A=0, SYNC IS OFF, FCC=1
        LAC
        CPI  000
        JTZ  FIN       PRINTING FINSHED IF C.P. =0
        RRC
        JFC  DATA      IF CP ODD, FFC=1, ODD=NO PRINT CYCLE
NP      LAI  200       NO PRINT CYCLE. C.P. IS ODD. C=1
        ORD            MASK IN BIT #7 TO D
        OUT  017       DISABLE DATA LINE
        LDA            LOAD BACK TO STATUS WORD
DEL1    LAI  004       NOOP TIME DELAY 1
NPX     SUI  001
        JFZ  NPX
        JMP  CPON?
DATA    LAI  174
        NDD            MASK OUT BITS 0,1,7 FROM D
        LDA            STORE RESULT IN D
        LAI  377
        XRM            COMPLEMENT MEMORY
        NDI  003       MASK OUT UPPER 6 BITS OF MEMORY
        XRD            COMBINE D WITH ACCUM.
        OUT  017       OUTPUT DATA ENABLE, HRP, HRQ
        LDA            RELOAD STATUS WRD WITH NEW HRP&Q BITS
        LAM            SHIFT MEMORY 2 BITS
```

```
        RRC
        RRC
        LAA           HRP&Q DATA SET UP IN M FOR NEXT TIME
        DCE
        JFZ  D        IF E=0, MEMORY BYTE IS USED UP
        DCL           POINT TO NEXT MEM. BYTE
        LEI  004      RESET SHIFT COUNTER
        JMP  CPON?
        LAA           NOOP TIME DELAY 2
        LAA
        LAA
CPON?   INB           INCREMENT TIMING COUNTER
        INP  007
        RRC
        JTC  CPON?    LOOP UNTIL CP GOES ON=ZERO
SYNC?   NDI  100      IF BIT 7 INPUT(BIT 6 IN ACC)=0, SYNC IS ON
        JFZ  K        IF RESULT IN A REG=0, SYNC IS ON, FFC=1
        LAI  020
        ORD           MASK IN BIT 4. BIT=1, SYNC IS ON
        LDA           STORE STSTUS WORD
        DCC           DCRMNT COLUM PULSE COUNTER
K       LAI  005      MOTOR TIMING KONSTANT
MOTR1   CPB             RUM MOTOR SPEED CNTRL K 1
        JFC  TOFF       TIME CNTR B=<KONST A.  MOTOR TOO FAST
TON     LAI  373        MOTOR NOT TOO FAST. TURN IT ON
        NDD             MASK MOTOR ON BIT OUT OF D. BIT=0=ON
        LDA             STORE NEW STSUS WORD
        OUT  017        TURN ON MOTOR. HRP&Q OUTPUT SAME AS BEFORE
        JMP  RESET
TOFF    LAI  004
        ORD           MASK MOTOR ON BIT INTO STATUS WORD
        LDA           STORE NEW STATUS WORD
        OUT  017      TURN OFF MOTOR. HRP&Q SAME AS BEFORE
        LAA           NOOP TIME DELAY X
RESET   LBI  000      RSSET TIMING COUNTER
R       INB           INCREMENT TIMING COUNTER
        INP  007
        RRC
        JFC  R        LOOP UNTIL CP GOES OFF=1
        JMP  RUN
FIN     LAI  373      KEEP MOTOR ON
        OUT  017
X       INP  007
        RLC
        RLC
        JFC  X        WAIT FOR PRINT READY OFF, BIT 6=1
        LAI  377      CLEAR OUTPUT AND STOP MOTOR
        OUT  017
        RET
@
@
@
THE PRINT ROUTINE CLRS THE PRINT MATRIX@
AND THE PERFORMS THE SEQUENCING ROUTINE AS FOLLOWS.@
THE SEQUENCER SUBROUTINE RECIEVES DATA FROM THE @
IO BUFFER STARTING AT THE LOW ORDER END, IO12, LEFT END, AND@
TRANSFERS IT ONE BYTE AT A TIME TO THE CONVR@
ROUTINE (TO CHANGE BINARY CODED HEXADECIMAL TO @
BIT POSITIONAL) , AND THE TO THE FILL ROUTINE(@
(TO FILL MATRIX FOR PRINTER). IT DOES THIS 12 TIMES@
ONCE FOR EACH COLUMN INCLUDINDG SYMBOLS@
AFTER 12 TIMES, THE DRIVER IS EXECUTED FOR PRINTING@
AND THEN THE CONTROL PASSES BACK TO THE SEQUENCER@
```

AND THEN BACK TO THE ROTINES WHICH CALLED THE PRINT●
ROUTINE.. ALL REG ARE USED BY THE PRINT ROUTINE.●
●
●
PRINT CAL CLMAT
SEQN  LDI 013         013(8)=11(10)
      PAM IO12        BEGINNING OF IO BUFFER FOR DATA
      LEL
AGAIN LLE
      LAM
      LBD
      CAL CONVR
      INE
      DCD
      JFS AGAIN       BRANCH TO AGAIN IF B IS STIL POSITIVE
SING  PAM MATRX
      CAL DRIVE
      RET
●
●
●
THE CLMAT ROUTINE CLEARS THE 17(10) BYTE MATRIX●
USED TO STORE BIT POSITIONAL DATA REQUIRED TO●
EXECUTE THE DRIVE ROUTINE FOR THE LINE PRINTER●
●
●
●
CLMAT PAM MAT
      LCI 021         17(10)
      LDI 000
CLIR  LMD
      INL
      DCC
      JFZ CLIR
      RET
●
●
●
●
THE CONVR ROUTINE LOOKS AT BINARY CODED●
HEXADECIMAL DATA RECIEVED IN THE A REGISTER●
REPRESENTING THE VALE U OF A SINGLE DIGIT●
AND THE BINARY CODED VALUE OF THE DIGITS COL. IN REG B●
INORDER TO COMPUTE THE BIT POSITIOAL VALUE TO BE●
TRANSFERED TO THE FILL ROUTINE IN THE A REGISTER.●
FOR COL 12-2, 000(8)-011(8),PRINTS 0(10)-9(10)●
FOR COL 1,      "       "      " THE FULL RANGE OF SYMBOLS●
FOR COL 12-2,013(8) PRINTS   DOTS .....●
FOR COL 1         "      "        E SYMBOLS●
ALL OTHER OCTAL VALUES IN THE A REGISTER CUASE BLANKS●
●
●
CONVR CPI 014         14(8)=C(16)=12(10)=BLANKS
      RFC             RETURN IF A=>R
      CPI 012         12(8)=A(16)=10(10)=BLANK
      RTZ             RETURN IF A=R
      CPI 000
      JTZ ZERO
VALID LCA             A REG = 1(8) TO 11(8),OR 1(10) TO 9(10)
      LAM 013         11(10)
      SUC
MULT  LCA
      XRA

```
MU      ADI 014          14(8)=12(10) REPETITIVE ADDING
        DCC
        JFZ MU
        ADI 001
        JMP COL
ZERO    LAI 015          13(10)
COL     ADB
```
*
THE FILL ROUTINE TAKES THE BIT POSITIONAL VALUE@
RECIEVED FROM THE CONVR ROUTINE IN TH E A REG@
AND TURNS ON THE RESPETIVE BIT IN THE MATRIX.@
THE HIGHEST ADDRESS BYTE GETS #1 BIT, AND THE @
LOWEST ADRESS BYTE GETS THE #132 BIT.@
THE HIGHEST ORDER 4 BITS OF THE LOWEST ADRESS BYTE@
ARE NOT USED. THE MATRIX IS 17(10) BYTES LONG.@
@
@
@
@

```
FILL    PAM MATRX        MATRIX IS FILLED STARTING AT LOW
                         ORDER END@
CMP     CPI 010          IS CODE POSITION=<8?. IF YES, THEN
                         NO MORE BYTE SHIFTS ARE REQUIRED@
        JTZ SHFT         A=R
        JTC SHFT         A<R
        SUI 010          8(10)
        DCL              POINT TO NEXT BYTE
        JMP CMP
SHFT    LDA              BIT SHIFTING ROUTINE
        LAI 001
SH      DCB
        JTZ LODE         IF REG B=0, NO MORE BIT SHIFTS REQUIRED
        RLC
        JMP SH
LODE    ORM
        LMA
        RET
```
@
@
@
@
```
I012    ADR 012343
MATRX   ADR 012377
MAT     ADR 012357
```
@
@
@SINGL CAUSES A SINGLE GIGIT TO BE PRINTED. COL # IN B REG.
@DIGIT VALUE IN A REG. CONYTRL RETURNS TO CAL ROUTINE
```
SINGL   CAL CLMAT        REQUIRES COL# IN B, DIGIT# IN A
        CAL CONVR
        JMP SING
```
@
```
        END
```
@
UNSTR ROUTINE CAUSES A 3 BYTE MEMORY CELL TO BE EXPANDED@
TO A 6 BYTE HEX-DEC FORMAT RESIDING IN IO BUFFER.@
REQUIRES THE E REG TO COME WITH THE MEM CELL ADRES@
REG E C B H L D A ARE USED. ON EXIT E POINTS TO MEM CELL.@
@
```
UNSTR   LCE              C POINTS TO MEM CEL LOW ADRES ON P 010
        LBI 003          ITERATION CONSTANT
        LDI 343          I012 LOW ADRES. H=012
X       LLC              POINT TO MEM CELL
```

```
LHI 010
LAI 360
NDA           MASK OUT LOW 4 BITS, RESULT IN A REG
RRC           SHIFT UPPER 4 BITS DOWN TO LOW 4 BITS
RRC
RRC
RRC
LLD           POINT TO IOBUF FOR LOADING
LHI 012
LMA             LOAD EXPANDED DATA TO IO BUF
IND
LLC           POINT TO MEM CELL
LHI 010
LAI 017
NDA           MASK OUT UPPER 4 BITS OF MEM CEL BYTE
LLD           POINT THE NEXT IO BYTE
LHI 012
LMA           LOAD EXPANDED DATA TO IOBUF
IND           POINT TO NEXT IO BYTE FOR NEX ITERATION
INC           POINT TO NEXT MEM CELL BYTE
DCB
JFZ X         DIO IT AGAIN, MAX 3 TIMES
RET           E POINTS TO MEM CELL LOW ADRES. H=012

END
@PREP.......
@
PREP   LHI 011
       CAL REED      000 001 TO RAM 011, MODE? TO 011
       JMP MODE?
       JMP MODE?     EQUIV TO 3 NOOPS
@
REED   ADR 000016
MODE?  ADR 011000
@
@
RU     CAL SEP       MAKE FULL LINE OF DOTS&E
       CAL PRINT
       LBI 006         BOOT ANAL TO RAM 012
       LHI 012
       CAL ADVAN       000 006 TO RAM 012    ANAL
       LHI 011
       CAL REED        000 007 TO RAM 011, SOME
       LHI 014         ADVANCE TAPE. DUMMY RAM PAGE
       LBI 030         POINT TO NEXT TAPE. 040
       CAL ADVAN
       JMP ANAL
@
SEP    LBI 014       11 DOTS & E TO IOBUF
       PAM I012
       LAI 013       DOTS &E
AN     LMA
       INL
       DCB
       JFZ AN
       RET
@
ADVAN  CAL WAITD     CONTINUOUS READ
A      LCI 005
       CAL AD
       DCC
       LAI 001       #1=CONTIN. ADVAN READ ERROR
```

```
        JTS ER?        PRINT IN COL 1.  HLT IF ERROR.
        DCB
        JFZ A
        RET
●
ER?   ADR 000023
IO12  ADR 012343
WAITD ADR 000174
AD    ADR 000070
IOSYM ADR 012356
PRINT ADR 001210
BEGIN ADR 000000
IOCNT ADR 012342
ANAL  ADR 012000
●
●
        END
MODE? JMP R
R       ADR 011037
        END
R     LHI 010        RUN MODE
      CAL REED       000 002 TO RAM 010 TAPE FWRD 1 BLK
      CAL REED       000 003 TO RAM 010 CNTRL 1 RUN VER
      JMP AUTO1
REED  ADR 000016
AUTO1 ADR 011355
        END
●MODE?......AUTO1
AUTO1 LHI 012
      CAL REED       000 004 TO RAM 012, CNTRL2. HLT IF ERR?
      LHI 011        OVERLAY CNTRL3 TO RAM 011
      CAL REED       000 005 TO RAM 011, CNTRL3.
●NEXT INSTRUCTION OBTAINED FM PROGRAM CNTR. IT IS THE
●CAL ABORT FROM THE OVRLT ROUTINE IN CNTRL3 AT 011 367
●
REED  ADR 000016
●
        END
        INL
        DCB
        JFZ ZE
        LEC
        CAL UNST     MEM CELL P10 TO IOBUF P 12
        CAL PRINT
        PAM CEE
        LCM          RESET C REG
        CAL NEXCL    ADVANCE TO NEXT MEM CELL
        JMP HIT
●
FA    CAL LAST?
      LHI 010
FAL   LAI 001
      CAL CELL?
      JTZ P
      LAI 022        ....12  END OF FILE
      CAL CELL?
      JTZ NOMOR
      CAL NEXCL
      JMP FAL
●
UNST  ADR 002324
PRINT ADR 001210
```

```
NOMOR ADR 000000
CEE   ADR 011375
I012  ADR 012343
@
      END
@MASTER CONTROL SEGMENT FOR INPUT FROM KEYBOARD
@
MASTR CAL CLMEM       CLEAR INPUT DATA STORAGE MEMORY
INP   CAL CLIO        CLEAR I/O BUFFER
IN    CAL KEY         INPUT A KEY FROM KEYBOARD
      FALL THRU TO DECOD@
@
DECOD ROUTINE LOOKS AT KEYBOARD INPUT AND @
BRANCHES TO A NUMBER HANDLER, A CLEAR BUFFER FUNCTION@
, A ENTER THE KEYBORAD DATA LINE FOR PROCESSING.@
, DELETE A DATA LINE FUNCTION, AND A RUN SYSTEM@
FUNCTION. 2 XRTA INPUT KEY FUNCTIONS ARE STILL AVAILABLE@
@
DECOD LBI 012         12(8) = A(16) = 10(10)
      CPB             INPUT TO THIS ROUTINE IN A REG
      JTC NUMB        IF A REG =0-9, OR , <12(8), ITS A @
      JTZ ENTER       IF A REG =12(8) , ENTER FUNCTION KEY
      INB
      CPB
      JTZ CLEAR       CLEAR CURRENT INPUT ITEM, 13(8)
      INB
      CPB
      JTZ RUN         RUN FUNCTION KEY, 14(8)
      INB
      CPB
      JTZ LOOK-       LOOK-DELETE KEY, 15(8)
      INB
      CPB
      JTZ PGFUN       PAGE/FUNC NOT USED HER IN RUN VER, 16(8)
      JMP RESTR       RESTART FUNCTION KEY 17(8)
NUMB  CAL LDBUF       LOAD 1 DIGIT TO BUFFER.FROM REG A
      JMP IN
ENTER ADR 012000
CLEAR ADR 010003      SAME AS INP
RUN   ADR 012327
LOOK- ADR PAGE 010@
PGFUN ADR 010003      SAME AS INP
RESTR ADR 010000      SAME AS MASTR
@
KEY ROUTINE: INPUT KEY WITH 'N' KEY ROLLOVER@
REG A B C H L DESTROYED. RETURNS WITH BINARY@
CODED HEXADECIMAL IN A REG.@
TWO BYTES OF RAM CALLED MASK ARE REQUIRED@
@
KEY   PAM MASK
      INP 005
      LBA
      LAM
      LMB
      XRI 377
      NDB
      LBA
      INL
      INP 006
      LCA
      LAM
      LMC
```

```
        XRI 377
        NDC
        LCA
        LLI 020
LOOP    XRA
        LAB
        RLC
        LBA
        LAC
        PAL
        LCA
        DCL
        LAL
        RTC
        NDA
        JFZ LOOP
        JMP KEY
```
@
LOAD I/O BUFFER ROTINES PERMIT THE SEQUENTIAL LOADING@
OF A 11 BYTE BUFER FROM LEFT TO RIGHT. SYMB. LOADS SEPARATE.@
NAMELY,LOW ORDER ADRESS TO HIGH ORDER ADRESS.@
THE RIGHT JUSTIFIED COL.BYTE, IS FOR SYMBOLS.@
THE DATA COMES TO THESE ROUTINES IN HEXADECIMAL@
BINARY CODED FORMAT.@
CLIO, CLEAR I/O CAN BE USED USED TO CLEAR THE I/O BUUFER@
AS AN INDEPENDENT ROUTINE AT ANY TIME.@
OVRFL, OVERFLOW OF THE BUFFER , AUTOMATIVALLY CLEARS THE @
I/O BUFFER, PLACES THE SYMB*- IN THE BUFFER,PRINTS OUT THE SYM@

SMBOL, AND RETURNS TO CALLING PROGRAM@
THE OVERLOW PROGRAM CONSIDERS THE OVERFLOW CONDITION@
TO COME ALWAYS FROM EXTERNAL KEYBOARD USE. THEREFORE@
IT TRANSFERS CONTROL BACK TO INP ROUTINE@
@
```
LDBUF   LCA             STORE HEXDEC DATA IN C
        LAI 012         12(8)=10(10). A IS 1 LESS THAN ALLOWED BYTES

CAL OVRFL       HAS 11 BYTES BEEN LOADED ALREADY?
        LBM             LOAD IOCNT,ADRESSED BY OVRFL, TO B REG
        INB
        LMB             STORE NEW BYTE POINTER
        LAL             LOW ADRESS TO A
        ADB             ADD NEW BYTE POINTER COUNT TO A
        LLA             PLACE LOE ARESS OGBUFFER BYTE IN L
        LMC             LOAD NEW DATA TO BUUFER
        RET
```
@
CLIO ROUTINE- CLEARS IO BUFFER@
000 GOES INTO IOCNT. 017 INTO ALL OTHER BUFFER POSITIONS@
017 = BLANKS TO PRINT CONVR ROUTINE. 000=ZEROS.@
@
```
CLIO    PAM IOCNT       CLEAR IO BUFFER
        LMI 000         IOCNT ZEROED
        INL
        LBI 014         12(10) POSITIONS CLEARED WITH 017
ZE      LMI 017
        INL
        DCB
        JFZ ZE
        RET
```
@
```
OVRFL   PAM IOCNT       BUFFER BYTE POINTER
        CPM             SET A= ALLOWED# DIGITS BEFORE ENTRY
```

```
            RFC           RETURN IF A=>R.  IF R>A, FALL THRU
            CAL CLIO         CLEAR IO BUFFER
            LAI 004       OVERFLOW SYMBOL, UNDERLINED DIAMOND
S           PAM IOSYM
            LMA           LOAD HEX-DEC VALUE TO IOSYM POSITION
SPL         CAL SPLIT
PR          CAL PRINT
            JMP INP       CONTROL RETURNED TO KEYBOARD INPUT
@
DOTS        LAI 013       REQUIRES # OF DOTS IN B REGISTER
            LMA           REQUIRES H&L FROM CALLING ROTINE
            INL
            DCB
            JFZ DOTS
            RET
@
@
MASK   ADR 012340          2 BYTES RESERVED, 340&341
IOCNT  ADR 012342
IO12   ADR 012343
IO11   ADR 012344
IO10   ADR 012345
IO9    ADR 012346
IO8    ADR 012347
IO7    ADR 012350
IO6    ADR 012351
IO5    ADR 012352
IO4    ADR 012353
IO3    ADR 012354
IO2    ADR 012355
IOSYM  ADR 012356
MAT    ADR 012357
MATRX  ADR 012377          HIGH ADRESS OF 17(10) BYTE MATRIX
PRINT  ADR 001210
CLIEI  ADR 012023
ADIN   ADR 012041
SPLIT  ADR 012260
@
THE ADOUT ROUTINE CAUSES THE LOW ORGER ADRESS@
STORED IN L GREGISTER TO BE CONVERTED TO SEGMENTED HEXADECIMAL@

FORMAT SUITABLE FOR USE BY THE IOBUFFER AND PRINT ROUTINES@
REGISTERS A E H & L AGARE USED. THE L REGISTER IS THE SAME@
ON EXIT FROM THIS ROUTINE. THIS ROUTINE CONVERTS@
OCTAL DATA PRESENTED TO IT IN THE L REG.@
@
ADOUT  LEL           STORE LOW ADRESS IN E
       PAM IO2       HANDLE LOWEST 3 BITS FOR IO2
       LAE
       NDI 007
       LMA
       DCL           HANDLE MIDDLE 3 BITS FOR IO3
       LAE
       RRC
       RRC
       RRC
       NDI 007
       LMA
       DCL           HANDLE TOP 2 BITS FOR IO4
       LAE
       RLC
       RLC
```

```
       NDI 003
       LMA
       LLE            RESTORE L REGISTER. H=012
       RET
●
●
● UNSTR ROUTINE CAUSES A 3 BYTE MEMORY CELL TO BE EXPANDED●
● TO A 6 BYTE HEX-DEC FORMAT RESIDING IN IO BUFFER.●
● REQUIRES THE E REG TO COME WITH THE MEM CELL ADRES●
● REG E C B H L D A ARE USED. ON EXIT E POINTS TO MEM CELL.●
●
UNSTR  LCE            C POINTS TO MEM CELL LOW ARESS. ON P 13
       LBI 003        ITERATION CONSTANT
       LDI 343        IO12 LOW ADRES. H=012
X      LLC            POINT TO MEM CELL
       LHI 013
       LAI 360
       NDM            MASK OUT LOW 4 BITS, RESULT IN A REG
       RRC            SHIFT UPPER 4 BITS DOWN TO LOW 4 BITS
       RRC
       RRC
       RRC
       LLD            POINT TO IOBUF FOR LOADING
       DCH            H=012
       LMA            LOAD EXPANDED DATA TO IO BUF
       IND
       LLC            POINT TO MEM CELL
       INH            H=013
       LAI 017
       NDM            MASK OUT UPPER 4 BITS OF MEM CEL BYTE
       LLD            POINT THE NEXT IO BYTE
       DCH            H=012
       LMA            LOAD EXPANDED DATA TO IOBUF
       IND            POINT TO NEXT IO BYTE FOR NEX ITERATION
       INC            POINT TO NEXT MEM CELL BYTE
       DCB
       JFZ X          DIO IT AGAIN, MAX 3 TIMES
       RET            E POINTS TO MEM CELL LOW ADRES. H=012
●
● LOOK- FINDS VALID MEM CEL ADRES. DATA TO IO BUF &PRINTED.
● IF LOOK- KEY PUSHED AGAIN,MEM CEL ZEROED(DELETED).
● DATA,ADRES,&-,PRINTED. IF PGFUN PUSHED,PAGE 13 PRINTS.
● CNTRL TO INP. ANY OTHER KEY PUSHED DEFAULTS TO INP.
●
LOOK-  LAI 003        LIMIT INPUT GIGITS TO 3
       CAL OVRFL
       CAL ADIN       LOCATES VALID DESIRED ADRES
       CAL UNSTR      UNSTORE& EXPAND CONDENSED DATA TO IOBUF
       JMP LOK
LOK    ADR 011000     ITERATION CONST FOR RESETING MEM CELL
ZMEM   LBI 003        MEM CELL POINT FM UNSTR, SAME ON EXIT DELET
       LLE
       LHI 013
       LAI 377
J      LMA
       INL
       DCB
       JFZ J          DO IT AGAIN, MAX 3 TIMES
       LAI 006        MINUS SYMBOL -
       JMP S          SYMB TO IO,SPLIT,PRINT,JMP INP
       END
```

@ENTER ROUTINE CAUSES 6 DIGITS OF DATA TO BE STORED
@IN MEMORY IF STORAGE ROOM IS AVAILABE.
@
```
ENTER   LAI  006         LIMIT INPUT TO 6 DIGITS
        CAL  OVRFL
ENT     CAL  FNEMP       FIND AN EMPTY MEM CELL ADRES
        CAL  ADOUT       PLACE ADRES IN I05,4,3
        CAL  STOR        STORE 6 DIGITS INPUT DATA
        LAI  005         + SYMB FOR IO BUF
        JMP  S           SYMB TO IO, SPLIT,PRINT,JMP INP
```
@
@
@CLEAR MEMORY PLACES 377 IN EACH BYTE OF EACH 3 BYTE CELL
@
```
CLMEM   LBI  377         ABSOLUTE # OF BYTES RESERVED
        PAM  MEMFR       BEGINNING ADRES OF MEM
MOR     LMI  377
        INL
        DCB
        JFZ  MOR
        RET
```
@
@
ADIN FINDS A DESIRED MEMORY CELL. ONLY VALID CELLS CAN@
BE LOCATED WITH TIHS ROUTINE. IMPROPER REQUEST WILL RESULT@
IN AN ERROR SYMBOL (E). IF MEMORY CELL LOCATED ITS OCYTAL@
LOW ORDER ADRES WILL BE LEFT IN THE E REG.@
USES ALL ADRESSES@
@
```
ADIN,   PAM  MEMFR
        LEL              MEMORY CELL POINTER
P       PAM  I012        IO BUFFER ADRES INP POINTER
        LCL
        PAM  I04         IO BUFFER ADRES OUT POINTER
        LDL
        LBI  003         ITERATION CONSTANT
        LLE
        CAL  ADOUT       L ON ENTRY SAME L&E ON EXIT
Q       LLC
        LAM              1ST GIGIT OF INPUT TO A
        LLD
        CPM              COMPARE IO INP BYTE TO IO OUT BYTE
        JFZ  NEXCL       LOOK AT NEXT MEMORY CELL IF D&C ARE NOT =
        INC              NEXT INP IO BYTE
        IND              NEXT OUT IO BYTE POINTER
        DCB
        JFZ  Q           NOT ZERO YET. DO IT AGAIN
        RET              DESIRED MEM CEL LOW ADRES IN E.  H=013
NEXCL   LLE              TEMP STOR OF CURRENT MEM CEL ADRES
        LAI  003
        ADE
        LEA              STOREE NEXT MEM CEL POINTER
        LAL              CURRENT MEM CELL ADRES TO A
        PAM  MEMLT
        CPL              LAST LOW ORDER ADRES VS CURR LOW ADRES
        JFZ  P           JMP TO P, THERE ARE MORE CELLS TO LOOK AT
ER      LLI  353         POINT TI I04
        LHI  012
        LBI  003         ITERATE DOTS 3 TIMES
        CAL  DOTS
        LAI  013         E SYMBOL FOR ERROR--ILLEGAL ADRESS INPUT
        JMP  S           SYMB TO IO,SPLIT,PRINT,JMP INP
```

```
@
@FNEMP SCANS DATA STORAGE MEMORY TO LOCATE AN EMPTY
@CELL TO LOAD 6 DIGITS OF INPUT DATA
@MEMLT POINTS TO ADRESS POSITION OF LAST 24 BIT MEMORY CELL@
@
FNEMP  PAM  MEMLT       FIND EMPTY MEMORY LOCATION
       LCL
       PAM  MEMFR       POINTS TO FIRST MEMORY CELL
       LDL              D REG WILL POINT TO 1ST BYTE OF EACH CELL
TRIAD  LBI  003
       LLD
       LAI  377         377 INDICATES BYTE NOT FILLED
EX     CPM
       JFZ  NEX3X       GO TO NEXT TRIPLET
       DCB
       JTZ  FOUND       WE HAVE AN EMPTY TRIPLET MEM CELL
       INL
       JMP  EX          KEEP LOOKING AT MORE TRIP. MEM. CELLS
NEX3X  LAD
       CPC
       JTZ  FULL        MEMORY IS FILLRD
       ADI  003
       LDA
       JMP  TRIAD
FOUND  LLD
       RET              H=013   L=FOUND LOW ADRES IN P 013
FULL   CAL  CLIO
       LAI  007         X SYMBOL
       JMP  S           SYMB TO IO, SPLIT, PRINT, JMP INP
@
@STOR TAKES TWO BYTES OF IO DATA IN HEX-DEC FORMAY
@AND CONDENSES IT TO 1 BYTE IN MEM STORAGE. THIS REPEATS
@3 TIMES. RECIEVES MEM CELL ADRES FROM CALLING ROUTINE
@REQUIRES L=MEM CEL LOW ADRES
STOR   LEI  003
       LBL              STORE MEMORY CELL POINTER
       LCI  343         POINTS TO IO12 LOW ADRES
AGAN   LLC              POINT TO IO BUF
       LHI  012
       LAM              X000AAAA
       NDI  017         0000AAAA
       RLC
       RLC
       RLC
       RLC
       LDA              AAAA0000
       INL
       LAM              X000BBBB
       NDI  017         0000BBBB
       XRD              AAAABBBB  CONDENSED 2 BYTES IO IN A REG
       INL
       LCL              STORE IOBUFER POINTER FOR NEXT BYTE
       LLB              POINT TO MEMORY CELL FOR LOADING
       INH              H=013
       LMA              STORE 2 BYTES IO INTO MEMORY CELL
       INB              INCREMENT POINTER FOR NEXT MEMORY CELL
       DCE              THIS ROUTINE IS PERFORMED 3 TIMES
       JFZ  AGAN
       RET              H=013
@
@
@SPLIT CAUSES A DOT TO BE PLACED BETWEEN 3RD &4TH INPUT
@DIGIT IN ORDER TO IMPROVE READABILITY PRINTED OUTPUT
@
```

```
SPLIT   LLI 346         ADR I09   H SET BY CAL ROUT.
        LAM               STORE I09
        LMI 013         LOAD I09 WITH DOT
        INL               ADR I08
        LBM               STORE I08
        LMA               LOAD I08 WITH I09
        INL             ADR I07
        LAM             STORE I07
        LMB             LOAD I07 WITH I08
        INL             ADR I06
        LMA             LOAD I06 WITH I07
        RET
@
REED    ADR 000016
RU      ADR 010013
DOTS    ADR 010217
OVRFL   ADR 010166
ADOUT   ADR 010230
S       ADR 010201
MEMFR   ADR 013000
MEMLT   ADR 013374
I012    ADR 012343
I04     ADR 012353
CLIO    ADR 010145
@
@FUNC ALLOWS A 2 DIGIT NUMBER TO BE PACED IN BYTE
@ THREE OF THE MEMORY CELL AND DOTS IN THE FIRST TWO
@ OF THE MEMORY CELL, NAMELY OCTAL 273, 273. THE CLEAR,
@ ENTER, AND DELETE FUNCTIONS OPERATE IN THE SAME WAY
@ AS FOR HANDLING REGULAR NUMERIC DATA ENTRIES.
@ THE FUNC ROUTINE OPERATES IN EDIT MODE ONLY
@
FUNC    LAI 002         LIMIT ENTYRY TO 2 DIGITS
        CAL OVRFL
        LLI 343         POINT TO I012, 343.  CALL ROUT. SETS H=12
        LAM
        INL         I011 342
        LBM
        LLI 347     I08 347
        LMA
        INL         I07 350
        LMB
        LBI 004
        LLI 343     I012 343
        CAL DOTS
        JMP ENT         LATE ENTRY TO ENTER ROUTINE
@
RUN     LHI 010
        CAL REED        000 000 TO RAM 010   RU
        JMP RU
        END
@CNTRL3.......
@LOK PERMITS LOOKING AT A ADRESSED ITEM. DELETION IS
@ACCOPLISHED BY DEPRESSING THE DELETE KEY AGAIN.
@DELETION CAN BE SKIPPED BY PUSHING ANY KEY EXCEPT
@THE FULL PAGE -FUNCTION KEY.
@THE FULL PAGE-FUNCTION KEY CAUSES DISPLAY OF ALL
@VALID DATA ITEMS ON PAGE. BLANK HOLES ARE NOT VALID.
@
LOK     PAM HOLDE       HOLD E IN TEMP STOR
        LME
        LHI 012
```

```
        CAL SPLIT
        CAL PRINT
        CAL KEY
        CPI 016         FULL PAGE-FUNCTION
        JTZ PAGEE       LOOK AT ENTIRE PAGE OF INPUT
        CPI 015         IS DEPETE KEY PUSHED TWICE?
        JFZ INP         DEFAULT TO INP IF NOT 015
ZM      PAM HOLDE
        LEM
        JMP ZMEM
●
PAGEE   LEI 000
REPET   CAL CLIO        H=12
        LHI 013
        LLE
        LAI 377
        CPM             IS MEM CELL DATA=377=EMPTY?
        JTZ SKIP
        CAL ADOUT       INTERNAL HANDLES H. E=L ON EXIT
        CAL UNSTR       INTERNAL HANDLES H. E=L ON EXIT
        LHI 012
        CAL SPLIT       E NOT ALTERED
        PAM HOLDE       H=12
        LME
        CAL PRINT       PRINT IOBUFFER. USES ALL REG
        PAM HOLDE
        LEM
SKIP    INE             ADVANCE POINTER TO NEXT MEM CELL
        INE
        INE
        LAI 377         IS L(E) ADRES AT LAST BYTE ON PAGE?
        CPE
        JTZ INP
        JMP REPET
●
●
PRINT   ADR 001210
KEY     ADR 010057
INP     ADR 010003
ZMEM    ADR 010342
CLIO    ADR 010145
ADOUT   ADR 010230
UNSTR   ADR 010262
SPLIT   ADR 012260
●
HOLDE   LOC 000001
●CNTRL3...... OVRLY
OVRLY   CAL ABORT       CNTRL FM PROG. CNTR. FM AUTO!
        CAL CASOF       TURN AC MOTOR OFF
        JMP MASTR       GO TO KEYBOARD CNTRL
●●
ABORT   ADR 000226
CASOF   ADR 000057
MASTR   ADR 010000
●
        END
●
ANAL    PAM RESUL       SET INDICATORS TO 200
        LAI 200
        LMA
        INL             RESL
        LMA
```

```
        INL     ORR
        LMA
        INL     XRO
        LMA
RE      LHI 010         ADVANCE TAPE 1 BLOCK
        CAL REED        HLT IF READ ERROR. PRINT 0
        LCI 000         MEM CELL POINTER FOR P 010, CASET
P       LHI 010         CASET MEM CEL POINTER, P010
        CAL LAST?
        LLC
        LAI 273         IS MEM CELL    DATA OR FUNCTION?
        CPM
        JFZ DATA
e                           ORR    XRO
e                   000     F      F
e                   001     T      T
e                   002     T      F
e                   INN     T      F
e                   200     T      T
e
FUN     PAM ORR         CHECK &RESET ORR&XRO FUNCTIONS
        XRA
        CPM             000=FALSE    >0=TRUE
        LMI 200         RESET ORR MEM
        JTZ FALSE       IF A=R, JMP TO FALSE
        INL             POINT TO XRO
        LAM
        LMI 200         RESET XRO MEM
        CPI 001         001 IS VALID
        JTZ FU
        CPI 200         200 = NON OPERATIVE FUNCTION
        JFZ FALSE       ANY VALUE EXCEPT 001 &200 ARE FALSE
FU      INC
        INC             SET C TO BYTE 3
        LLC             POINT TO BYTE 3 M
        INC             SET C TO NEXT MEM CELL
        LHI 010
        LBM             LOAD MEM BYTE 3(FUNC) TO B
        PAM FUNC
        LMB             STORE MEM BYTE 3 IN FUNC
        LAI 021         END OF LOGICAL DATA FUNCTION,....11
        CPB
        JTZ HIT         SUCESS!
        LAI 022         END OF FILES FUNCTION?   ....12
        CPB
        JTZ NOMOR       GO TO END OF FILE ROUTINE
        LAI 002         SON, SITE ON, FUNCTION? ....02
        CPB
        JTZ SONE
        LAI 005         SISTP, SITE STOP, FUNCTION? ....05
        CPB
        JTZ SISTP
        JMP P           LOOK AT NEXT MEM CELL FOR DATA
e                       OR ANOTHER SUBSEQUENT FUNCTION.
e
e
DATA    LHI 010         P 010 MEM CELL TO REG B, D, E
        LLC
        LBM
        INL
        LDM
        INL
```

```
        LEM
        INL
        LCL          SAVE P 010 NEXT MEM CELL POINTER
        LHI 013
        LLI 000      KEYBOARD INPUT DATA PAGE 013
DAT     LAI 377      ARE WE AT THE LAST BYTE YET?
        CPL
        LAI 001      SET UP NO MATCH VALUE JUST IN CASE.
        JTZ EVAL     IF AT LAST BYTE, THEN NO MATCH
        LAB          IS THE MEM CELL CASET IN MEM CELL KETBRD?
        CPM
        JFZ FAIL1
        INL
        LAD
        CPM
        JFZ FAIL2
        INL
        LAE
        CPM
        JFZ FAIL3
        XRA          A=000     THIS IS A MATCH
        JMP EVAL
FAIL1   INL
FAIL2   INL
FAIL3   INL          POINT TO NEXT MEM CELL
        JMP DAT      KEEP CHECKING KEYBRD INPUT FOR MATCH
@
@
EVAL    LDA          A=000 FOR MATCH    =001 FOR NO MATCH
        PAM FUNC     WHAT IS THE OPERAND
        LBM
        LAI 006         AND?
        CPB
        JTZ AND
        LAI 007         NOT?
        CPB
        JTZ NOT
        LAI 010         XROR?
        DCL          POINT TO XRO
        CPB
        JTZ R
        LAI 011         OR?
        DCL          POINT TO ORR
        CPB
        JTZ R
        JMP P        INVALID FUNCTION. IGNORE DATA.
@                    GO LOOK AT NEXT CASET MEM CELL@
@
NOT     LAI 001      COMPLIMENT BIT 0 OF REG D
        XRD
        LDA          NOW TREAT NOT FUNCTION AS AN AND FUNCTION
AND     XRA
        CPD
        JTZ P        AND: MATCH FOUND-RECORD VALIDATED
                     NOT: NO MATCH FOUND-RECORD VALIDATED@
        JMP FALSE    AND: NO MATCH FOUND-RECORD INVALIDATED
@                    NOT: MATCH FOUND-RECORD INVALIDATED@
@
R       LAI 177
        NDM          MASK OUT BIT 7
        LBA
        XRA
```

```
           CPD
           JFZ  V        IF A=000=A MATCH, FALL THRU TO NEXT INST
           INB
V          LMB           STORE FUNCTION RESULT FOR LATER REVIEW
           JMP  P        JMP TO P. CHECK NEXT CASET MEM CEL
@
@
FALSE PAM  RESUL         IS SITE OPERATION ON?
      LAI  200
      CPM
      JTZ  FA            IF SITE OP OFF, LOOK FOR INTERREC. FUNC.
      LMI  001           SET RESUL=001=FALSE PERMUTATION
      JMP  P             ATTEMPT MORE PERMUTATIONS
@
FA    ADR  011342
SONE  ADR  011047
SISTP ADR  011177
HIT   ADR  011266
NOMOR ADR  000000        SAME AS BEGIN
REED  ADR  000016
LAST? ADR  011000
NEXCL ADR  011007
CELL? ADR  011016
@
SONAD LOC  000001
RESUL LOC  000001
RESL  LOC  000001
ORR   LOC  000001
XRU   LOC  000001
FUNC  LOC  000001
@
@
      END
@
LAST? LAI  377           IS THIS LAST BYTE, 377, ON PAGE?
      CPC
      JTZ  ANAL
      RET
@
NEXCL INC                ADVANCE ADRES POINTER 3 BYTES
      INC
      INC
      CAL  LAST?
      RET
@
CELL? LHI  010
      LLC               FIND A SPECIFIC CELL FUNCTION
      INL               REG A =....FUNCTION; C=MEM CEL BYT 1;
      INL               REG H= 010. CAL ROUTINE PROVIDES A,C,H
      CPM               IS MEMCELL BYTE 3= ....FUNCTION?
      RFZ
      DCL
      DCL
      LAI  273
      CPM               IS MEMCEL BYTE 1=273
      RET               FUNCT CELL FOUND-=TZ. NOT FOUND=FZ
@
SOF?  LAI  003           ....SOF=....03=003; FIND SOF.
SOFF  CAL  CELL?         ADVANCE TO SOF CELL
      RTZ
      CAL  NEXCL
      JMP  SOF?
```

```
SONE    PAM SONAD
        LMC             STORE SON+1 MEM CEL IN SONAD
        INL               POINT TO RESUL
        LMI 000         000=SITE SYSTEM IS NOW OPERATING
SON     LHI 010
        CAL LAST?
        LAI 003         ....SOF=....03=003
        CAL CELL?       .IS CELL FUNC=SOF?
        JTZ EV          ALL PERMUTATIONS &COMPARES COMPLETED
USED?   LLC             MEM CELL IS AN OPERATOR
        LBM             STORE OPERATOR BYTE 1 IN B
        LMI 377         SET MEM BYTE 1 TO 377=USED
        INL
        LDM             STORE OPERATOR BYTE 2 IN D
        LAI 377
        CPB             IS THIS OPERATOR CELL ALREADY USED?
        JFZ PERM
        CAL NEXCL
        JMP SON
PERM    CAL SOF?        ADVANCE TO SOF MEM CEL
AG      CAL NEXCL       ADVANCE TO NEXT MEM CELL
        LAI 005         ....SITE STOP=....05=005
        CAL CELL?       IS THIS MEM CELL=SITESTOP FUNCTION?
        JTZ RES         IF YES, PERMUTATION PASS COMPLETED
        LAI 273         IS THIS MEM CELL A FUNCTION?
        LLC             EXAMINE MEM CEL BYTE 1
        CPM
        JTZ AG          IF MEM CEL IS A FUNCTION,LOOK AT NEXT CELL
PERMA   LMB             THIS MEM CELL NEEDS PERMUTATION
        INL             B &  D REG REMAIN CONSTANT
        LAI 017           00001111
        NDM             MASK OUT UPPER 4 BITS OF BYTE 2
        LMA               0000XXXX
        LAI 360           11110000
        NDD             MASK OUT LOW 4 BITS OF D. RESULT TO A
        ORM             ZZZZXXXX
        LMA             ZZZZXXXX   1/2 D + 1/2 M
        JMP AG
RES     PAM SONAD       RETRIEVE ADRES SON+1 MEM CELL
        LCM
        CAL SOF?        ADVANVE TO SOF CELL
        CAL NEXCL       POINT TO 1ST MEM CELL AFTER SOF
        JMP P
SISTP   PAM SONAD
        LCM             C=SON+1 MEM CELL
        INL               POINT TO RESUL
        LAI 001         IS RESUL=001=A FALSE PASS?
        CPM
        LMI 000         RESET RESUL TO 000
        JTZ SIS
        INL             POINT TO RESL
        LMI 000          SET RESL=000=TRUE, IFRESUL=000=TRUE
SIS     JMP SON
EV      PAM RESL         CHECK&RESET RESUL&RESL
        LBM
        LMI 200          RESET RESL=200
        DCL             POINT TO RESUL
        LMI 200           RESET RESUL=200
        LAI 000
        CPB
        JFZ FA          IF RESL=B=000, SITE OPERATION TRUE
TRU     CAL NEXCL       ADVANCE TO SITE STOP
```

```
        LHI 010
        LAI 005
        CAL CELL?
        JFZ TRU
        CAL NEXCL    ADVANCE TO 1 PAST SITE STOP
        JMP P        ALL SITE OPERATIONS ARE COMPLETED!!
HIT     PAM CEE          SAVE C REG
        LMC          STORE MEM CEL ADRES TO BE EXAMINED
        LAI 001           ....01=INTERREC FUNCTION
        CAL CELL?
        JTZ P        GO TO P IF INTERREC FUNCT.
CLRIO   PAM IO12         POINT TO IO 12
@
SONAD   ADR 012335
RESUL   ADR 012336
RESL    ADR 012337
P       ADR 012024
ANAL    ADR 012000
SING    ADR 001235
@
        LBI 014      CLEAR IOBUF
ZE      LHI 017
```

TABLE 36
COMPUTER PROGRAM MEMORY LOCATION TABLE

| COMPUTER PROGRAM INSTRUCTIONS LISTED IN TABLE NUMBER | MEMORY LOCATIONS FROM | MEMORY LOCATIONS TO | MAGNETIC TAPE STORAGE BLOCK NUMBER |
|---|---|---|---|
| 9-11 | 000:000 | 000:375 | |
| 12-15 | 001:000 | 001:373 | |
| 16 | 002:324 | 002:370 | |
| 17 | 010:000 | 010:110 | 000:000 |
| 18 | 011:000 | 011:002 | 000:001 |
| | 011:037 | 011:051 | 000:001 |
| | 011:355 | 011:366 | 000:001 |
| 19-23 | 010:000 | 010:363 | 000:003 |
| 24-27 | 012:000 | 012:336 | 000:004 |
| 28-29 | 011:000 | 011:123 | 000:005 |
| | 011:367 | 011:377 | 000:005 |
| 30-32 | 012:000 | 012:334 | 000:006 |
| 33-35 | 011:000 | 011:374 | 000:007 |

The foregoing detailed description is illustrative of one embodiment of the invention, and it is to be understood that additional embodiments thereof will be obvious to those skilled in the art. The embodiments described herein together with those additional embodiments are considered to be within the scope of invention.

What is claimed is:

1. The method of operating a programmed automatic electronic computer to designate appropriate medical treatment for a patient who has been examined to determine each medical finding out of a predetermined set of medical findings which is present in the patient, the computer being adapted to have loaded therein and to read a readily interchangeable mass memory unit, said computer also including an entry unit and an output display system, said method comprising the steps of:

(a) loading the computer with a preprepared, readily interchangeable mass memory unit having stored therein signals representing the definitions of a plurality of disease entities, each disease entity definition including signals representing a plurality of corresponding selected disease codes, each corresponding selected disease code representing one out of the predetermined set of possible medical findings with respect to any patient's condition, and also including signals representing a plurality of logic codes which, together with the selected disease codes, designate a corresponding logical combination of the selected individual disease codes which defines the disease entity, said mass memory unit also having stored therein, for each disease entity definition, corresponding signals representing at least one corresponding treatment code representing an appropriate medical treatment to be given to any patient whose medical condition satisfies the disease entity definition;

(b) for each one of the predetermined set of medical findings found in the patient being treated, operating the entry unit of the computer to enter and to store in the computer electrical signals representing the corresponding disease code, whereby the stored patient disease codes represent the medical condition of the patient being treated;

(c) operating the computer to read the contents of the mass memory unit and to respond to the logic code signals and selected disease code signals of each disease entity definition to perform a corresponding logical testing of the stored patient disease codes to test and indicate if they satisfy the corresponding logical combination of selected disease codes of the disease entity and, for each of the disease entity definitions whose logical combination of selected disease codes is satisfied by the stored patient disease codes, display indicia representative of the corresponding treatment codes;

whereby the displayed indicia are representative of the treatment codes for all of the satisfied disease entity definitions.

2. A programmed computing apparatus usable by a paramedic with limited medical training to designate appropriate medical treatment for a patient to be treated who has been examined by the paramedic to determine each medical finding, out of a predetermined set of possible medical findings, which is present in the patient to be treated, said computing apparatus comprising:

(a) a programmed digital computer adapted to have loaded therein and to read from a readily interchangeable mass magnetic memory unit;

(b) said computer including a preprepared, readily interchangeable mass magnetic memory unit loaded into the computer, said unit having stored therein magnetic signals representing the definitions of a plurality of disease entities, each disease entity definition including signals representing a plurality of corresponding selected disease codes, each corresponding selected disease code representing one out of the predetermined set of possible medical findings with respect to any patient's condition, and also including signals representing a plurality of logic codes which, together with the selected disease codes, designate a corresponding logical combination of the selected individual disease codes which defines the disease entity, said mass magnetic memory unit also having stored therein, for each disease entity definition, corresponding signals representing at least one corresponding treatment code representing an appropriate medical treatment to be given to any patient whose medical condition satisfies the disease entity definition;

(c) said computer including an entry means operable by the paramedic to enter and to store in the computer electrical signals representing the corresponding disease code for each one of the predetermined set of medical findings present in the patient, the stored patient disease codes representing the medical condition of the patient being treated;

(d) said computer futher including logical testing and display means actuable for automatically reading the contents of the mass magnetic memory unit and responding to the logic code signals and selected disease code signals of each disease entity definition to perform a corresponding logical testing of the stored patient disease codes to test and indicate if they satisfy the corresponding logical combination of selected disease codes of the disease entity and, for each of the disease entity definitions whose logical combination of selected disease codes is satisfied by the stored patient disease codes, displaying indicia representative of the corresponding treatment codes;

whereby the displayed indicia are representative of the treatment codes for all of the satisfied disease entity definitions.

3. A programmed computing apparatus usable by a paramedic with limited medical training to designate appropriate medical treatment for a patient to be treated who has been examined by the paramedic to determine each medical finding, out of a predetermined set of possible medical findings, which is present in the patient to be treated, said computing apparatus comprising:

a programmed electronic digital computer for generating electrical signals representing the definitions of a plurality of disease entities, each disease entity definition including signals representing a plurality of corresponding selected disease codes, each corresponding selected disease code representing one out of the predetermined set of possible medical findings with respect to any patient's condition, and also including signals representing a plurality of logic codes which, together with the selected disease codes, designate a corresponding logical combination of the selected individual disease codes which defines the disease entity, said programmed electronic digital computer additionally providing for each disease entity definition, corresponding signals representing at least one corresponding treatment code representing an appropriate medical treatment to be given to any patient whose medical condition satisfies the disease entity definition;

said programmed electrical computer including an entry means operable by the paramedic to enter and to store in the computer electrical signals representing the corresponding disease code for each one of the predetermined set of medical findings present in the patient, the stored patient disease codes representing the medical condition of the patient to be treated;

said programmed electronic digital computer further including logical testing and display means responsive to the logic code signals and selected disease code signals to each disease entity definition for performing a corresponding logical testing of the stored patient disease codes to test and indicate if they satisfy the corresponding logical combination of selected disease codes of the disease entity and, for each of the disease entity definitions whose defined logical combination of selected individual disease codes is satisfied by the stored patient disease codes, displaying, responsive to said corresponding treatment code signals, indicia representative of the corresponding treatment codes representing the corresponding medical treatments to be given to the patient;

whereby the displayed indicia are representative of the treatment codes for all of the satisfied disease entity definitions.

4. The computing apparatus of claim 3 wherein for each satisfied disease entity definition said logical testing and display means of said computer additionally displays indicia representing the identification of the satisfied disease entity as a corresponding diagnosis, whereby indicia representative of both the corresponding treatment codes and diagnosis code are displayed for each satisfied disease entity definition.

5. The method of operating a programmed automatic electronic digital computer, including an entry unit and an output display system to designate appropriate medical treatment for a patient who has been examined to determine each medical finding out of a predetermined set of possible medical findings which is present in the patient, said method comprising the steps of:

(a) for each one of the predetermined set of medical findings found in the patient operating the entry unit of the computer to enter and to store in the computer electrical signals representing a corresponding disease code, whereby the stored patient disease codes represent the medical condition of the patient being treated;

(b) operating the computer in a preprogrammed mode of operation to perform the steps of:

(i) generating electrical signals representing the definitions of a plurality of disease entities, each disease entity definition including signals representing a plurality of corresponding selected disease codes, each corresponding selected disease code representing one out of the predetermined set of possible medical findings with respect to any patient's condition, and also including signals representing a plurality of logic codes which, together with the selected disease codes, designate a corresponding logical combination of the selected individual disease codes, which defines the disease entity;

(ii) generating for each disease entity definition, corresponding signals representing at least one corresponding treatment code representing an appropriate medical treatment to be given to any patient whose medical condition satisfies the disease entity definition; and (iii) responding to the logic code signals and selected disease code signals of each disease entity definition to perform a corresponding logical testing of the stored patient disease codes to test and indicate if they satisfy the corresponding logical combination of selected disease codes of the disease entity and, for each of the disease entity definitions whose defined logical combination of selected individual disease codes is satisfied by the stored patient disease codes, displaying indicia represented by said corresponding treatment code signals;

whereby the displayed indicia are representative of the treatment codes for all of the satisfied disease entity definitions.

* * * * *